US012788774B2

(12) United States Patent
Decker et al.

(10) Patent No.: US 12,788,774 B2
(45) Date of Patent: Nov. 10, 2026

(54) POTENTIATION OF DURABLE ANTITUMOR IMMUNITY BY MULTIFACTORIAL IMMUNE MODULATION

(71) Applicant: BAYLOR COLLEGE OF MEDICINE, Houston, TX (US)

(72) Inventors: William K. Decker, Houston, TX (US); Matthew M. Halpert, Houston, TX (US); Vanaja Konduri, Houston, TX (US)

(73) Assignee: BAYLOR COLLEGE OF MEDICINE, Houston, TX (US)

( * ) Notice: Subject to any disclaimer, the term of this patent is extended or adjusted under 35 U.S.C. 154(b) by 158 days.

(21) Appl. No.: 18/843,991

(22) PCT Filed: Mar. 17, 2023

(86) PCT No.: PCT/US2023/015506
§ 371 (c)(1),
(2) Date: Sep. 4, 2024

(87) PCT Pub. No.: WO2023/177870
PCT Pub. Date: Sep. 21, 2023

(65) Prior Publication Data

US 2025/0186486 A1 Jun. 12, 2025

Related U.S. Application Data

(60) Provisional application No. 63/321,205, filed on Mar. 18, 2022.

(51) Int. Cl.

| | |
|---|---|
| ***A61K 31/00*** | (2006.01) |
| ***A61K 9/00*** | (2006.01) |
| ***A61K 31/198*** | (2006.01) |
| ***A61K 31/352*** | (2006.01) |
| ***A61K 31/4245*** | (2006.01) |
| ***A61K 31/4709*** | (2006.01) |
| ***A61K 31/4745*** | (2006.01) |
| ***A61K 31/663*** | (2006.01) |
| ***A61K 31/7076*** | (2006.01) |
| ***A61K 31/7084*** | (2006.01) |
| ***A61K 31/713*** | (2006.01) |
| ***A61K 33/34*** | (2006.01) |
| ***A61K 38/19*** | (2006.01) |
| ***A61K 39/395*** | (2006.01) |
| ***A61P 35/00*** | (2006.01) |

(52) U.S. Cl.

CPC ............ *A61K 33/34* (2013.01); *A61K 9/0019* (2013.01); *A61K 31/198* (2013.01); *A61K 31/352* (2013.01); *A61K 31/4245* (2013.01); *A61K 31/4709* (2013.01); *A61K 31/4745* (2013.01); *A61K 31/663* (2013.01); *A61K 31/7076* (2013.01); *A61K 31/7084* (2013.01); *A61K 31/713* (2013.01); *A61K 38/191* (2013.01); *A61P 35/00* (2018.01)

(58) Field of Classification Search
None
See application file for complete search history.

(56) References Cited

U.S. PATENT DOCUMENTS

2014/0005255 A1 1/2014 Monaco et al.
2022/0040310 A1 * 2/2022 Wang .................... A61K 47/61

OTHER PUBLICATIONS

Batlle E, Massague J (2019) Transforming Growth Factor-beta Signaling in Immunity and Cancer. Immunity 50: 924-940.

Beatty GL, Gladney WL (2015) Immune escape mechanisms as a guide for cancer immunotherapy. Clin Cancer Res 21: 687-92.

Bhatnagar et al., Combination of Sting and TLR 7/8 Agonists as Vaccine Adjuvants for Cancer Immunotherapy, Cancers, 14:6091, 2022.

Bhola et al. (2013) TGF-beta inhibition enhances chemotherapy action against triple- negative breast cancer. J Clin Invest 123: 1348-58.

Brockstedt et al., (2002) Development of anti-tumor immunity against a non-immunogenic mammary carcinoma through in vivo somatic GM-CSF, IL-2, and HSVtk combination gene therapy. Mol Ther 6: 627-36.

Carroll et al., (2016) The Vaccine Adjuvant Chitosan Promotes Cellular Immunity via DNA Sensor cGAS-STING-Dependent Induction of Type I Interferons. Immunity 44: 597-608.

Chester C, Sanmamed MF, Wang J, Melero I (2018) Immunotherapy targeting 4-1BB: mechanistic rationale, clinical results, and future strategies. Blood 131: 49-57.

Cristescu et al. (2018) Pan-tumor genomic biomarkers for PD-1 checkpoint blockade-based immunotherapy. Science 362.

Decker WK, Safdar A (2009) Bioimmunoadjuvants for the treatment of neoplastic and infectious disease: Coley's legacy revisited. Cytokine Growth Factor Rev 20: 271-81.

Decker WK, Safdar A (2011) Cytokine adjuvants for vaccine therapy of neoplastic and infectious disease. Cytokine Growth Factor Rev 22: 177-87.

Feola et al., (2018) Oncolytic vaccines increase the response to PD-L1 blockade in immunogenic and poorly immunogenic tumors. Oncoimmunology 7: e1457596.

Galluzzi L, Buque A, Kepp O, Zitvogel L, Kroemer G (2017) Immunogenic cell death in cancer and infectious disease. Nat Rev Immunol 17: 97-111.

Garber K (2018) A new cancer immunotherapy suffers a setback. Science 360: 588.

Halpert et al., "Multifactoral Immune Modulation Potentiates Durable Remission in Multiple Models of Aggressive Malignancy", Faseb J., 38(10):323644, 2024.

(Continued)

*Primary Examiner* — Brian Gulledge
(74) *Attorney, Agent, or Firm* — pH IP Law

(57) ABSTRACT

Methods are provided for enhancing an immune response comprising providing an immunogenic composition comprising a cocktail of intracellular agonists, immune inhibition antagonists, and cytostatic/damage-inducing agents. Further provided herein are methods of treating a primary tumor and preventing metastasis.

25 Claims, 25 Drawing Sheets

(56) References Cited

OTHER PUBLICATIONS

Hamilton et al., (2014) Macrophages are more potent immune suppressors ex vivo than immature myeloid-derived suppressor cells induced by metastatic murine mammary carcinomas. J Immunol 192: 512-22.
Hervas-Stubbs et al., (2011) Direct effects of type I interferons on cells of the immune system. Clin Cancer Res 17: 2619-27.
Ilyas S, Yang JC (2015) Landscape of Tumor Antigens in T Cell Immunotherapy. J Immunol 195: 5117-22.
International Search Report and Written Opinion for PCT/US2023/015506 (Atty Dkt BACM.P0009WO) dated Jul. 11, 2023, 24 pages.
Jacobson et al., Historical and Current Adenosine Receptor Agonists in Preclinical and Clinical Development. Front. Cell. Neurosci., 2019.
Jafari et al., (2017) A3 Adenosine Receptor Agonist Inhibited Survival of Breast Cancer Stem Cells via GLI-1 and ERK1/2 Pathway. J Cell Biochem 118: 2909-2920.
Kawai T, Akira S (2009) The roles of TLRs, RLRs and NLRs in pathogen recognition. Int Immunol 21: 317-37.
Kerr et al., "The Next Generation of Immunotherapy for Cancer: Small olecules Could Make Big Waves", *The Journal of Immunology*, 202(1): 11-19, 2018.
Krieg AM (2007) Development of TLR9 agonists for cancer therapy. J Clin Invest 117: 1184-94.
Lee SW, Salek-Ardakani S, Mittler RS, Croft M (2009) Hypercostimulation through 4- 1BB distorts homeostasis of immune cells. J Immunol 182: 6753-62.
Liu L, Wang Y, Miao L, Liu Q, Musetti S, Li J, Huang L (2018) Combination Immunotherapy of MUC1 mRNA Nano-vaccine and CTLA-4 Blockade Effectively Inhibits Growth of Triple Negative Breast Cancer. Mol Ther 26: 45-55.
Mandal et al. (2019) Genetic diversity of tumors with mismatch repair deficiency influences anti-PD-1 immunotherapy response. Science 364: 485-491.
Meng et al., "poly (I:C) synergizes with proteasome inhibitors to induce apoptosis in cervical cancer cells", *Translational Oncology*, 18:101362, 2022.
Mitchell BS (2003) The proteasome -- an emerging therapeutic target in cancer. Engl J Med 348: 2597-8.
Rodon et al., (2015) First-in-human dose study of the novel transforming growth factor- beta receptor I kinase inhibitor LY2157299 monohydrate in patients with advanced cancer and glioma. Clin Cancer Res 21: 553-60.
Segal et al., (2017) Results from an Integrated Safety Analysis of Urelumab, an Agonist Anti-CD137 Monoclonal Antibody. Clin Cancer Res 23: 1929-1936.
Shi et al., (2013) Differential involvement of Th1 and Th17 in pathogenic autoimmune processes triggered by different TLR ligands. J Immunol 191: 415-23.
Shira et al., "adenosine receptor to treat cytokine release syndrome in cancer immunotherapy", *Drug Design, Development and Therapy*, 13:491-497, 2019.
Simpson et al., (2012) Macrophage migration inhibitory factor promotes tumor growth and metastasis by inducing myeloid-derived suppressor cells in the tumor microenvironment. J Immunol 189: 5533-40.
Sinha P, Clements VK, Bunt SK, Albelda SM, Ostrand-Rosenberg S (2007) Cross-talk between myeloid-derived suppressor cells and macrophages subverts tumor immunity toward a type 2 response. J Immunol 179: 977-83.
Sinha P, Clements VK, Ostrand-Rosenberg S (2005a) Interleukin-13-regulated M2. Macrophages in combination with myeloid suppressor cells block immune surveillance against metastasis. Cancer Res 65: 11743-51.
Sinha P, Clements VK, Ostrand-Rosenberg S (2005b) Reduction of myeloid-derived suppressor cells and induction of M1 macrophages facilitate the rejection of established metastatic disease. J Immunol 174: 636-45.
Skrott Z, Cvek B (2012) Diethyldithiocarbamate complex with copper: the mechanism of action in cancer cells. Mini Rev Med Chem 12: 1184-9.
Spranger et al., (2010) Generation of Th1-polarizing dendritic cells using the TLR7/8 agonist CL075. J Immunol 185: 738-47.
Stetson DB, Medzhitov R (2006) Recognition of cytosolic DNA activates an IRF3-dependent innate immune response. Immunity 24: 93-103.
Sun L, Wu J, Du F, Chen X, Chen ZJ (2013) Cyclic GMP-AMP synthase is a cytosolic DNA sensor that activates the type I interferon pathway. Science 339: 786-91.
Vinay et al. (2015) Immune evasion in cancer: Mechanistic basis and therapeutic strategies. Semin Cancer Biol 35 Suppl: S185-S198.
Xagorari A, Chlichlia K (2008) Toll-like receptors and viruses: induction of innate antiviral immune responses. Open Microbiol J 2: 49-59.
Yatim et al., (2017) Dying cells actively regulate adaptive immune responses. Nat Rev Immunol 17: 262-275.
Zhang et al. (2019) Lactate Is a Natural Suppressor of RLR Signaling by Targeting MAVS. Cell 178: 176-189 e15.
Zhao et al., (2019) A conserved PLPLRT/SD motif of STING mediates the recruitment and activation of TBK1. Nature 569: 718-722.

* cited by examiner

Regimen 15

| | | |
|---|---|---|
| 2-Cl-IB-MECA | Adenosine A3 Receptor agonist | To delay and/or inhibit tumor cell replication AND activate immune cells |
| Copper(II) Diethyldithiocarbamate | Proteosome inhibitor | |
| RIG-I agonist | Stimulates RIG-I with dsRNA | |
| TLR7/8 Agonist (Resiquimod; R848) | Stimulates TLR7/8 with ssRNA | |
| DMXAA | STING agonist | |

Regmien 16

| | | |
|---|---|---|
| 2-Cl-IB-MECA | Adenosine A3 Receptor agonist | To delay and/or inhibit tumor cell replication AND activate immune cells |
| Copper(II) Diethyldithiocarbamate | Proteosome inhibitor | |
| DMXAA | Sting Agonist | |
| RIG-I agonist | Stimulates RIG-I with dsRNA | |
| TLR7/8 Agonist (Resiquimod; R848) | Stimulates TLR7/8 with ssRNA | |
| **Galunisertib** | **Selective TGF$\beta$R1 Inhibitor** | |

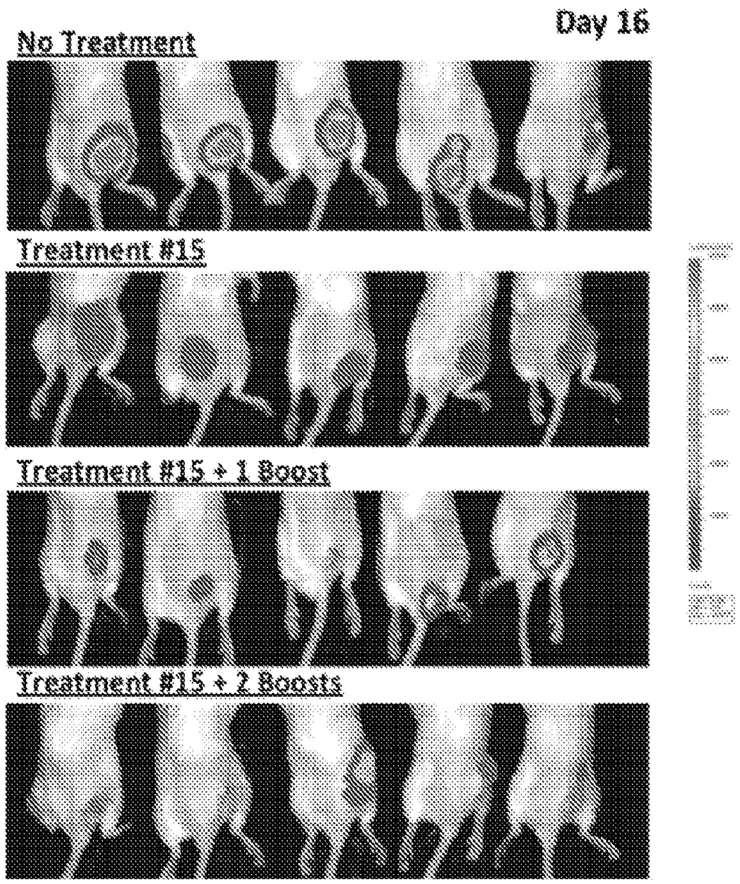

FIG. 2A

A)

| Treatment Designation | Agents | Fundamental Mechanism | General Goal |
|---|---|---|---|
| 1 | DMSO/PBS | Vehicle Control | Negative Control |
| 2 | Clodronate | Phagocyte (M2) depletion | Eliminate immunsuppressive M2 macrophages and MDSC |
| 3 | Epacadostat<br>N$^{\omega}$-Hydroxy-nor-L-arginine<br>L-NMMA | IDO1 inhibitor<br>Arginase inhibitor<br>iNOS inhibitor | Inhibit immunosuppressive MDSC and M2 Macrophages |
| 4 | Clodronate<br>Epacadostat<br>N$^{\omega}$-Hydroxy-nor-L-arginine<br>L-NMMA | Phagocyte (M2) depletion<br>IDO1 inhibitor<br>Arginase inhibitor<br>iNOS inhibitor | Eliminate immunosuppressive phagocytes and inhibit M2 and MDSC cells |

B)

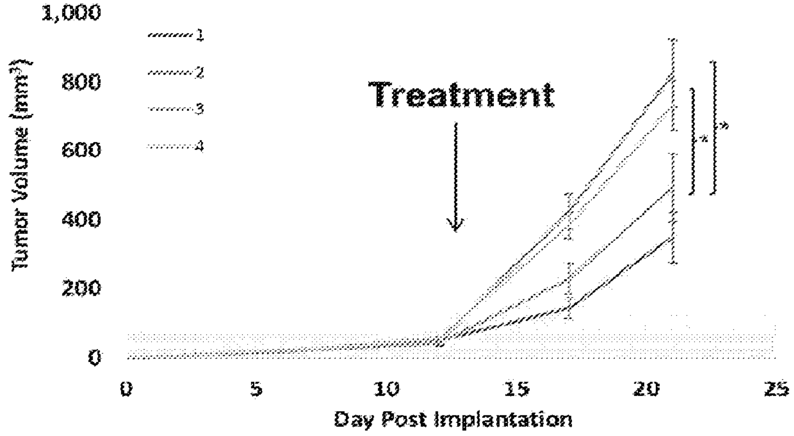

C)

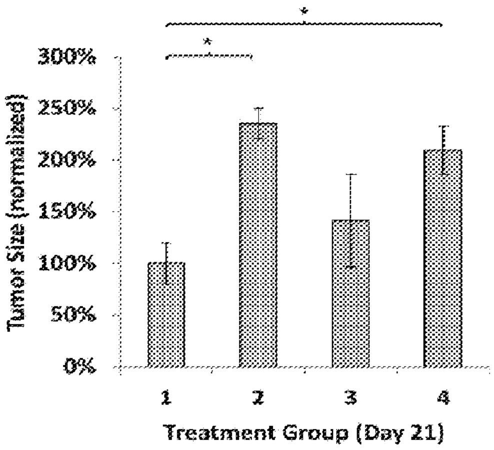

FIGS. 7A-7C

A)

| Treatment Designation | Agents | Fundamental Mechanism | General Goal |
|---|---|---|---|
| 1 | DMSO/PBS | Vehicle Control | Control |
| 5 | 4-1BB ligand | Stimulate 4-1BBR | Stimulate Local T cell Responses |
| 6 | RIG-I agonist<br>TLR7/8 Agonist (Resiquimod; R848)<br>DMXAA | Stimulates RIG-I with dsRNA<br>Stimulates TLR7/8 with ssRNA<br>STING agonist | Stimulate Local Innate Immune cells (e.g. pDC) |
| 7 | 4-1BB ligand<br>RIG-I agonist<br>TLR7/8 Agonist (Resiquimod; R848)<br>DMXAA | Stimulate 4-1BBR<br>Stimulates RIG-I with dsRNA<br>Stimulates TLR7/8 with ssRNA<br>STING agonist | Stimulate Local Innate cells and T cells |

B)

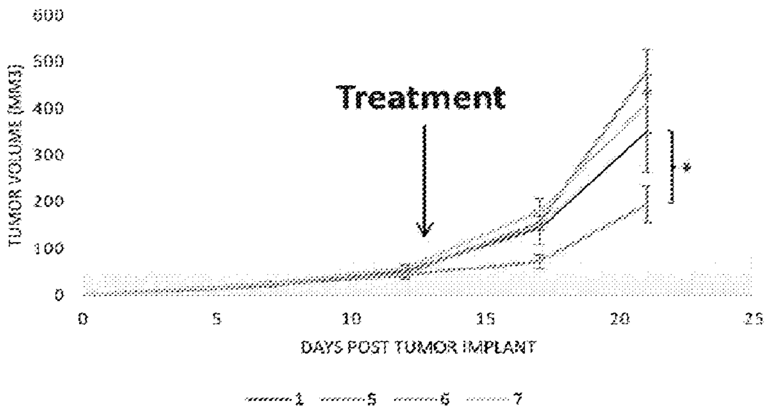

C)

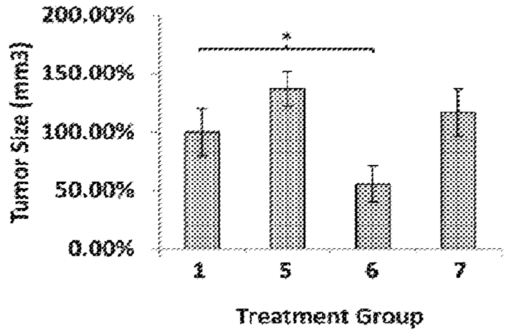

FIGS. 8A-8C

POTENTIATION OF DURABLE ANTITUMOR IMMUNITY BY MULTIFACTORIAL IMMUNE MODULATION

PRIORITY CLAIM

This application is a § 371 of International Application No. PCT/US2023/015506 filed Mar. 17, 2023 which claims the benefit of U.S. Provisional Patent Application No. 63/321,205, filed Mar. 18, 2022, both of which is incorporated herein by reference in their entirety.

FEDERAL GRANT SUPPORT

This invention was made with government support under Grant No. R01 AI127387 awarded by the National Institutes of Health. The government has certain rights in the invention.

BACKGROUND

1. Field

The present invention relates generally to the field of molecular biology, immunology and medicine. More particularly, it concerns methods and compositions for stimulating an anti-tumor immune response.

2. Description of Related Art

Triple negative breast cancer (TNBC) is a highly aggressive and malignant subtype of breast cancer that lacks expression of the estrogen receptor (ER) and the progesterone receptor (PR) and does not exhibit marked amplification or overexpression of human epidermal growth factor receptor 2 (HER2/ERBB2). In contrast to $ER^+$, $PR^+$, or $HER2^{HI}$ tumors, TNBCs currently lack a well-characterized molecular target for therapy and are associated with high rates of relapse and distant recurrence despite aggressive surgery and adjuvant chemotherapy. Diagnosis of TNBC is often delayed, and a majority of women present with advanced disease for which five-year survival is an abysmal 30%. Accordingly, though TNBCs comprise only 15% of US breast cancer diagnoses, they account for half of all deaths, an estimated 20,000 per year. Given the lack of effective adjuvant therapy for TNBC, there is an urgent, unmet medical need for the development of novel treatment regimens that can reduce the incidence of distant recurrence, preventing significant comorbidities and sparing life. (Hubalek, Czech et al., 2017, Marra, Viale et al., 2019, Waks & Winer, 2019)

The concept of immune surveillance in cancer was controversial for many decades until the advent of immune checkpoint inhibition established that tumor reactive T-cells both exist and may be rendered functionally relevant by blockade of signaling pathways associated with tolerance, exhaustion, and/or anergy. (Brahmer, Tykodi et al., 2012, Hodi, O'Day et al., 2010, Topalian, Hodi et al., 2012) For some oncologic indications, particularly those with high mutational burdens such as melanoma, smoking-signature NSCLC, or any dMMR/$MSI^+$ tumor type, the results can be dramatic as exemplified by the present day durable remission rate of almost 50% in stage IV melanoma following combinatorial therapy with inhibitors that block both the CTLA-4 and PD-1 signaling pathways. (Hellmann, Ciuleanu et al., 2018, Marcus, Lemery et al., 2019, Overman, Lonardi et al., 2018, Wolchok, Chiarion-Sileni et al., 2017)

Nonetheless, a majority of tumors still fail to respond to checkpoint inhibitor therapy, and even tumor types that can respond often do not if sufficient neoantigen reactive T-cells have not been spontaneously generated by the time therapy is initiated. To overcome this significant limitation and induce the generation of more tumor-reactive T-cells, many investigators have experimented with a variety of different immune agonist and antagonist compounds, both as single agents as well as in combination with checkpoint inhibition. One of the problems with this approach is that there exist a vast number of different agonist and antagonist pathways that interact with each other, with tumor, and with immune effector cells redundantly as well as in unknown and unpredictable ways. Thus, there is an unmet need for the development of novel treatment regimens for the treatment of TNBC as well as other aggressive cancers, such as pancreatic ductal adenocarcinoma (PDAC), melanoma, and head and neck cancer.

SUMMARY

In a first embodiment there is provided an immunogenic composition comprising at least 4 (e.g., at least 5, 6, or 7) of the following: a transforming growth factor beta (TGFβ) antagonist, a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist. In some aspects, the composition comprises (a) a transforming growth factor beta (TGFβ) antagonist or a 4-1BB agonist and (b) at least 3 (e.g., 4 or 5) of the following: a stimulator of interferon genes (STING) agonist, a Toll-like receptor 7/8 (TLR7/8) agonist, a RIG-I agonist, a proteasome inhibitor, and an adenosine A3 receptor agonist.

In a first embodiment there is provided an immunogenic composition comprising at least 4, at least 5, at least 6, or all 7 of the following: a transforming growth factor beta (TGFβ) antagonist, a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist. In some aspects, the composition comprises (a) a transforming growth factor beta (TGFβ) antagonist or a 4-1BB agonist and (b) at least 3, at least 4, or all 5 of the following: a stimulator of interferon genes (STING) agonist, a Toll-like receptor 7/8 (TLR7/8) agonist, a RIG-I agonist, a proteasome inhibitor, and an adenosine A3 receptor agonist.

In some aspects, the composition comprises a 4-1BB agonist, a stimulator of interferon genes (STING) agonist, a Toll-like receptor 7/8 (TLR7/8) agonist, a RIG-I agonist, and a proteasome inhibitor. In certain aspects, the composition comprises a transforming growth factor beta (TGFβ) antagonist, a stimulator of interferon genes (STING) agonist, a Toll-like receptor 7/8 (TLR7/8) agonist, a RIG-I agonist, and a proteasome inhibitor. In specific aspects, the composition comprises a 4-1BB agonist, a stimulator of interferon genes (STING) agonist, a Toll-like receptor 7/8 (TLR7/8) agonist, a RIG-I agonist, and an adenosine A3 receptor agonist. In particular aspects, the composition comprises a transforming growth factor beta (TGFβ) antagonist, a stimulator of interferon genes (STING) agonist, a Toll-like receptor 7/8 (TLR7/8) agonist, a RIG-I agonist, and an adenosine A3 receptor agonist. In some aspects, the composition comprises at least 5 of the following: a transforming growth factor beta (TGFβ) antagonist, a stimulator of interferon genes (STING) agonist, a Toll-like receptor 7/8 (TLR7/8) agonist, a RIG-I agonist, a proteasome inhibitor, and an adenosine A3 receptor agonist. In certain aspects, the composition comprises at least 5 of the following: a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist. In some aspects, the composition comprises a transforming growth factor beta (TGFβ) antagonist, a stimulator of interferon genes (STING) agonist, a Toll-like receptor 7/8 (TLR7/8) agonist, a RIG-I agonist, a proteasome inhibitor, and an adenosine A3 receptor agonist. In certain aspects, the composition comprises a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist.

In some aspects, the TGFβ antagonist is galunisertib (LY2157299), trabedersen, fresolimumab, LY2382770, lucanix, or PF-03446962. In certain aspects, the STING agonist is a cyclic dinucleotide or xanthenone analog. For example, the STING agonist is 2'3'-c-di-AM(PS)2 (Rp,Rp). In some aspects, the STING agonist is a cyclic dinucleotide selected from the group consisting of 3'3'-cGAMP, 2'3'-cGAMP, 2'2'-cGAMP, c-di-APM, c-di-GMP, c-di-IMP, and c-di-UMP. In certain aspects, the STING agonist is a xanthenone analog, such as 5,6-dimethylxanthenone-4-acetic acid (DMXAA). In certain aspects, the TLR7/8 agonist is resiquimod (R848), CL075, CL097, CL264, CL307, GS-9620, Poly(dT), imiquimod, gardiquimod, loxoribine or a ssRNA oligonucleotide. In certain aspects, the RIG-I agonist is 5'ppp-dsRNA, MDA5 ligand, a LGP2 ligand, a ssRNA, a dsRNA, Poly(dA:dT), or Poly(I:C). In some aspects, the proteasome inhibitor is Copper(II) Diethyldithiocarbamate, bortezomib, delanzomib, ixazomib, MG132, MG115, IPSI 001, fellutamide B, ALLN, leupeptin, epoxomicin, oprozomib, PR-957, carfilzomib, lactacystin, omuralide, salinosporamide A, salinosporamide B, a belactosine, a cinnabaramide, a polyphenol, TMC-95, or PS-519. In particular aspects, the adenosine A3 receptor agonist is 2-Chloro-N(6)-(3-iodobenzyl) adenosine-5'-N-methylcarboxamide (2-Cl-IB-MECA). IB-MECA (CF101), CP-608, 039, CP-532,903, MRS5698, MRS5980, LJ-529 33, or MRS4322. In some aspects, the 4-1BB agonist is a 4-1BB agonist antibody, recombinant 4-1BB ligand (4-1BBL), or 4-1BB apatamer. For example, the 4-1BB agonist antibody is utomilumab or urelumab.

In certain aspects, the composition does not comprise hydrogel. In other aspects, the composition does comprise a biomaterial, such as hydrogel or a polymer. In some aspects, the composition does not comprise an immune checkpoint inhibitor, cytokine, and/or antigen.

A further embodiment provides a pharmaceutical composition comprising the immunogenic composition of the present embodiments (e.g., an immunogenic composition comprising at least 4 (e.g., at least 5, 6, or 7) of the following: a transforming growth factor beta (TGFβ) antagonist, a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist) and an excipient.

A further embodiment provides a pharmaceutical composition comprising the immunogenic composition of the present embodiments (e.g., an immunogenic composition comprising at least 4, at least 5, at least 6, or all 7 of the following: a transforming growth factor beta (TGFβ) antagonist, a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist) and an excipient.

Another embodiment provides method of stimulating an anti-tumor immune response in a subject comprising administering to the subject an effective amount of at least 4 (e.g., at least 5, 6, or 7) of the following: a transforming growth factor beta (TGFβ) antagonist, a 4-11B agonist, a stimulator of interferon genes (STING) agonist, a Toll-like receptor 7/8 (TLR7/8) agonist, a RIG-I agonist, a proteasome inhibitor, and an adenosine A3 receptor agonist. In some aspects, the method comprises administering (a) a transforming growth factor beta (TGFβ) antagonist or a 4-1BB agonist and (b) at least 3 (e.g., 4 or 5) of the following: a stimulator of interferon genes (STING) agonist, a Toll-like receptor 7/8 (TLR7/8) agonist, a RIG-I agonist, a proteasome inhibitor, and an adenosine A3 receptor agonist.

Another embodiment provides method of stimulating an anti-tumor immune response in a subject comprising administering to the subject an effective amount of at least 4, at least 5, at least 6, or all 7 of the following: a transforming growth factor beta (TGFβ) antagonist, a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist. In some aspects, the method comprises administering (a) a transforming growth factor beta (TGFβ) antagonist or a 4-1BB agonist and (b) at least 3, at least 4, or all 5 of the following: a stimulator of interferon genes (STING) agonist, a Toll-like receptor 7/8 (TLR7/8) agonist, a RIG-I agonist, a proteasome inhibitor, and an adenosine A3 receptor agonist.

In some aspects, the subject is administered a 4-1BB agonist, a stimulator of interferon genes (STING) agonist, a Toll-like receptor 7/8 (TLR7/8) agonist, a RIG-I agonist, and a proteasome inhibitor. In certain aspects, the subject is administered a transforming growth factor beta (TGFβ) antagonist, a stimulator of interferon genes (STING) agonist, a Toll-like receptor 7/8 (TLR7/8) agonist, a RIG-I agonist, and a proteasome inhibitor. In certain aspects, the subject is administered a 4-1BB agonist, a stimulator of interferon genes (STING) agonist, a Toll-like receptor 7/8 (TLR7/8) agonist, a RIG-I agonist, and an adenosine A3 receptor agonist. In particular aspects, the subject is administered a transforming growth factor beta (TGFβ) antagonist, a stimulator of interferon genes (STING) agonist, a Toll-like receptor 7/8 (TLR7/8) agonist, a RIG-I agonist, and an adenosine A3 receptor agonist. In specific aspects, the subject is administered at least 5 of the following: a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist. In some aspects, the subject is administered at least 5 of the following: a transforming growth factor beta (TGFβ) antagonist, a stimulator of interferon genes (STING) agonist, a Toll-like receptor 7/8 (TLR7/8) agonist, a RIG-I agonist, a proteasome inhibitor, and an adenosine A3 receptor agonist. In some aspects, the subject is administered a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist. In certain aspects, the subject is administered a transforming growth factor beta (TGFβ) antagonist, a stimulator of interferon genes (STING) agonist, a Toll-like receptor 7/8 (TLR7/8) agonist, a RIG-I agonist, a proteasome inhibitor, and an adenosine A3 receptor agonist.

In some aspects, the TGFβ antagonist is galunisertib (LY2157299), trabedersen, fresolimumab, LY2382770, lucanix, or PF-03446962. In certain aspects, the STING agonist is a cyclic dinucleotide or xanthenone analog. For example, the STING agonist is 2'3'-c-di-AM(PS)2 (Rp,Rp). In some aspects, the STING agonist is a cyclic dinucleotide selected from the group consisting of 3'3'-cGAMP, 2'3'-cGAMP, 2'2'-cGAMP, c-di-APM, c-di-GMP, c-di-IMP, and c-di-UMP. In certain aspects, the STING agonist is a xanthenone analog, such as 5,6-dimethylxanthenone-4-acetic acid (DMXAA). In certain aspects, the TLR7/8 agonist is resiquimod (R848), CL075, CL097, CL264, CL307, GS-9620, Poly(dT), imiquimod, gardiquimod, loxoribine or a ssRNA oligonucleotide. In certain aspects, the RIG-I agonist is 5'ppp-dsRNA, MDA5 ligand, a LGP2 ligand, a ssRNA, a dsRNA, Poly(dA:dT), or Poly(I:C). In some aspects, the proteasome inhibitor is Copper(II) Diethyldithiocarbamate, bortezomib, delanzomib, ixazomib, MG132, MG115, IPSI 001, fellutamide B, ALLN, leupeptin, epoxomicin, oprozomib, PR-957, carfilzomib, lactacystin, omuralide, salinosporamide A, salinosporamide B, a belactosine, a cinnabaramide, a polyphenol, TMC-95, or PS-519. In particular aspects, the adenosine A3 receptor agonist is 2-Chloro-N(6)-(3-iodobenzyl) adenosine-5'-N-methylcarboxamide (2-Cl-IB-MECA). IB-MECA (CF101), CP-608, 039, CP-532,903, MRS5698, MRS5980, LJ-529 33, or MRS4322. In some aspects, the 4-1BB agonist is a 4-1BB agonist antibody, recombinant 4-1BB ligand (4-1BBL), or 4-1BB apatamer. For example, the 4-1BB agonist antibody is utomilumab or urelumab.

In some aspects, the subject is human. In certain aspects, the subject has cancer, such as triple negative breast cancer (TNBC), pancreatic ductal adenocarcinoma (PDAC), melanoma, or head and neck cancer.

In certain aspects, the administering is performed prior to surgical intervention. In some aspects, administering comprising intratumoral injection. In specific aspects, the intratumoral injection does not comprise a biomaterial, such as hydrogel or polymers.

In some aspects, the immunogenic composition is administered more than once. In certain aspects, the immunogenic composition is administered two or more times.

In certain aspects, administering the immunogenic composition results in an increase in circulating CD8+ T cells, M1 macrophages and/or tumor infiltrating dendritic cells. In specific aspects, the CD8+ T cells are CD8+ IFN-$\gamma^+$ cells. In particular aspects, administering the immunogenic composition results in a durable T cell memory response as measured by an increase in $CD44^+CD127^+$ T cells as compared to $CD44^+$ $CD127^+$ T cells prior to administration. In some aspects, the method does not comprise administering a cell therapy to said subject at the time the immunogenic composition is administered, such as not being administering within 1 day, 1 week, 2 weeks, 1 month, or 3 months of the immunogenic composition. In certain aspects, the method does not comprise administering an immune checkpoint inhibitor, cytokine, and/or antigen to said subject at the time the immunogenic composition is administered, such as not being administering within 1 day, 1 week, 2 weeks, 1 month, or 3 months of the immunogenic composition.

A further embodiment provides a method of treating a subject with cancer comprising administering to the subject an effective amount of at least 4 (e.g., at least 5, 6, or 7) of the following: a transforming growth factor beta (TGFβ) antagonist, a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist. In some aspects, the method comprises administering (a) a transforming growth factor beta (TGFβ) antagonist or a 4-11B agonist and (b) at least 3 (e.g., 4 or 5) of the following: a stimulator of interferon genes (STING) agonist, a Toll-like receptor 7/8 (TLR7/8) agonist, a RIG-I agonist, a proteasome inhibitor, and an adenosine A3 receptor agonist.

In some aspects, the subject is administered a 4-1BB agonist, a stimulator of interferon genes (STING) agonist, a Toll-like receptor 7/8 (TLR7/8) agonist, a RIG-I agonist, and a proteasome inhibitor. In certain aspects, the subject is administered a transforming growth factor beta (TGFβ) antagonist, a stimulator of interferon genes (STING) agonist, a Toll-like receptor 7/8 (TLR7/8) agonist, a RIG-I agonist, and a proteasome inhibitor. In certain aspects, the subject is administered a 4-1BB agonist, a stimulator of interferon genes (STING) agonist, a Toll-like receptor 7/8 (TLR7/8) agonist, a RIG-I agonist, and an adenosine A3 receptor agonist. In particular aspects, the subject is administered a transforming growth factor beta (TGFβ) antagonist, a stimulator of interferon genes (STING) agonist, a Toll-like receptor 7/8 (TLR7/8) agonist, a RIG-I agonist, and an adenosine A3 receptor agonist. In specific aspects, the subject is administered at least 5 of the following: a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist. In some aspects, the subject is administered at least 5 of the following: a transforming growth factor beta (TGFβ) antagonist, a stimulator of interferon genes (STING) agonist, a Toll-like receptor 7/8 (TLR7/8) agonist, a RIG-I agonist, a proteasome inhibitor, and an adenosine A3 receptor agonist. In some aspects, the subject is administered a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist. In certain aspects, the subject is administered a transforming growth factor beta (TGFβ) antagonist, a stimulator of interferon genes (STING) agonist, a Toll-like receptor 7/8 (TLR7/8) agonist, a RIG-I agonist, a proteasome inhibitor, and an adenosine A3 receptor agonist.

In some aspects, the TGFβ antagonist is galunisertib (LY2157299), trabedersen, fresolimumab, LY2382770, lucanix, or PF-03446962. In certain aspects, the STING agonist is a cyclic dinucleotide or xanthenone analog. For example, the STING agonist is 2'3'-c-di-AM(PS)2 (Rp,Rp). In some aspects, the STING agonist is a cyclic dinucleotide selected from the group consisting of 3'3'-cGAMP, 2'3'-cGAMP, 2'2'-cGAMP, c-di-APM, c-di-GMP, c-di-IMP, and c-di-UMP. In certain aspects, the STING agonist is a xanthenone analog, such as 5,6-dimethylxanthenone-4-acetic acid (DMXAA). In certain aspects, the TLR7/8 agonist is resiquimod (R848), CL075, CL097, CL264, CL307, GS-9620, Poly(dT), imiquimod, gardiquimod, loxoribine or a ssRNA oligonucleotide. In certain aspects, the RIG-I agonist is 5'ppp-dsRNA, MDA5 ligand, a LGP2 ligand, a ssRNA, a dsRNA, Poly(dA:dT), or Poly(I:C). In some aspects, the proteasome inhibitor is Copper(II) Diethyldithiocarbamate, bortezomib, delanzomib, ixazomib, MG132, MG115, IPSI 001, fellutamide B, ALLN, leupeptin, epoxomicin, oprozomib, PR-957, carfilzomib, lactacystin, omuralide, salinosporamide A, salinosporamide B, a belactosine, a cinnabaramide, a polyphenol, TMC-95, or PS-519. In particular aspects, the adenosine A3 receptor agonist is 2-Chloro-N(6)-(3-iodobenzyl) adenosine-5'-N-methylcarboxamide (2-Cl-IB-MECA), IB-MECA (CF101), CP-608, 039, CP-532,903, MRS5698, MRS5980, LJ-529 33, or MRS4322. In some aspects, the 4-1BB agonist is a 4-1BB agonist antibody, recombinant 4-1B13 ligand (4-1BBL), or 4-1BB apatamer. For example, the 4-1BB agonist antibody is utomilumab or urelumab.

In some aspects, the administering is performed prior to surgical intervention. In particular aspects, the subject has not undergone surgical resection of a tumor. In particular aspects, administering comprises injection of the immunogenic composition. In some aspects, the TGFβ antagonist (or 4-1BB agonist), STING agonist, TLR7/8 agonist, RIG-I agonist, proteasome inhibitor, and adenosine A3 receptor agonist are administered as one injection. In certain aspects, the TGFβ antagonist (or 4-1BB agonist), STING agonist, TLR7/8 agonist, RIG-I agonist, proteasome inhibitor, and adenosine A3 receptor agonist are administered as more than one injection. In certain aspects, the injection is an intratumoral injection.

In some aspects, the cancer is triple negative breast cancer (TNBC), PDAC, head and neck cancer, or melanoma. In certain aspects, the intratumoral injection does not comprise a biomaterial, such as hydrogel or a polymer. In some aspects, the intratumoral injection comprises a biomaterial, such as hydrogel or a polymer.

In certain aspects, administering is more than once. In some aspects, the administering is two or more times.

In some aspects, administering results in an increase in circulating CD8+ T cells, M1 macrophages and/or tumor infiltrating dendritic cells. In specific aspects, the CD8+ T cells are $CD8^{+}$ IFN-$\gamma^{+}$ cells. In particular aspects, administering results in a durable T cell memory response as measured by an increase in $CD44^{+}CD127^{+}$ T cells as compared to $CD44^{+}CD127^{+}$ T cells prior to administration. In certain aspects, the method does not comprise administering a cell therapy to said subject at the time the transforming growth factor beta (TGFβ) antagonist (or 4-1B13 agonist), stimulator of interferon genes (STING) agonist, Toll-like receptor 7/8 (TLR7/8) agonist, RIG-I agonist, proteasome inhibitor, and adenosine A3 receptor agonist are administered, such as not being administering within 1 day, 1 week, 2 weeks, 1 month, or 3 months of the immunogenic composition. In certain aspects, the method does not comprise administering an immune checkpoint inhibitor, cytokine, and/or antigen to said subject at the time the transforming growth factor beta (TGFβ) antagonist (or 4-1BB agonist), stimulator of interferon genes (STING) agonist, Toll-like receptor 7/8 (TLR7/8) agonist, RIG-I agonist, proteasome inhibitor, and adenosine A3 receptor agonist are administered, such as not being administering within 1 day, 1 week, 2 weeks, 1 month, or 3 months of the immunogenic composition.

In some aspects, the method further comprises administering an additional anti-cancer therapy. In certain aspects, the additional anti-cancer therapy comprises chemotherapy, radiotherapy, gene therapy, surgery, hormonal therapy, anti-angiogenic therapy or immunotherapy.

In certain aspects, the patient is a human. In some aspects, the patient has been previously administered an anti-cancer therapy.

A further embodiment provides a method of preventing tumor metastasis in a subject with cancer comprising administering to the subject an effective amount of at least 4 (e.g., at least 5, 6, or 7) of the following: a transforming growth factor beta (TGFβ) antagonist, a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist. In some aspects, the method comprises administering (a) a transforming growth factor beta (TGFβ) antagonist or a 4-1B13 agonist and (b) at least 3 (e.g., 4 or 5) of the following: a stimulator of interferon genes (STING) agonist, a Toll-like receptor 7/8 (TLR7/8) agonist, a RIG-I agonist, a proteasome inhibitor, and an adenosine A3 receptor agonist.

In some aspects, the subject is administered a 4-1BB agonist, a stimulator of interferon genes (STING) agonist, a Toll-like receptor 7/8 (TLR7/8) agonist, a RIG-I agonist, and a proteasome inhibitor. In certain aspects, the subject is administered a transforming growth factor beta (TGFβ) antagonist, a stimulator of interferon genes (STING) agonist, a Toll-like receptor 7/8 (TLR7/8) agonist, a RIG-I agonist, and a proteasome inhibitor. In certain aspects, the subject is administered a 4-1BB agonist, a stimulator of interferon genes (STING) agonist, a Toll-like receptor 7/8 (TLR7/8) agonist, a RIG-I agonist, and an adenosine A3 receptor agonist. In particular aspects, the subject is administered a transforming growth factor beta (TGFβ) antagonist, a stimulator of interferon genes (STING) agonist, a Toll-like receptor 7/8 (TLR7/8) agonist, a RIG-I agonist, and an adenosine A3 receptor agonist. In specific aspects, the subject is administered at least 5 of the following: a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist. In some aspects, the subject is administered at least 5 of the following: a transforming growth factor beta (TGFβ) antagonist, a stimulator of interferon genes (STING) agonist, a Toll-like receptor 7/8 (TLR7/8) agonist, a RIG-I agonist, a proteasome inhibitor, and an adenosine A3 receptor agonist. In some aspects, the subject is administered a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist. In certain aspects, the subject is administered a transforming growth factor beta (TGFβ) antagonist, a stimulator of interferon genes (STING) agonist, a Toll-like receptor 7/8 (TLR7/8) agonist, a RIG-I agonist, a proteasome inhibitor, and an adenosine A3 receptor agonist.

In some aspects, the TGFβ antagonist is galunisertib (LY2157299), trabedersen, fresolimumab, LY2382770, lucanix, or PF-03446962. In certain aspects, the STING agonist is a cyclic dinucleotide or xanthenone analog. For example, the STING agonist is 2'3'-c-di-AM(PS)2 (Rp,Rp). In some aspects, the STING agonist is a cyclic dinucleotide selected from the group consisting of 3'3'-cGAMP, 2'3'-cGAMP, 2'2'-cGAMP, c-di-APM, c-di-GMP, c-di-IMP, and c-di-UMP. In certain aspects, the STING agonist is a xanthenone analog, such as 5,6-dimethylxanthenone-4-acetic acid (DMXAA). In certain aspects, the TLR7/8 agonist is resiquimod (R848), CL075, CL097, CL264, CL307, GS-9620, Poly(dT), imiquimod, gardiquimod, loxoribine or a ssRNA oligonucleotide. In certain aspects, the RIG-I agonist is 5'ppp-dsRNA, MDA5 ligand, a LGP2 ligand, a ssRNA, a dsRNA, Poly(dA:dT), or Poly(I:C). In some aspects, the proteasome inhibitor is Copper(II) Diethyldithiocarbamate, bortezomib, delanzomib, ixazomib, MG132, MG115, IPSI 001, fellutamide B, ALLN, leupeptin, epoxomicin, oprozomib, PR-957, carfilzomib, lactacystin, omuralide, salinosporamide A, salinosporamide B, a belactosine, a cinnabaramide, a polyphenol, TMC-95, or PS-519. In particular aspects, the adenosine A3 receptor agonist is 2-Chloro-N(6)-(3-iodobenzyl) adenosine-5'-N-methylcarboxamide (2-Cl-IB-MECA). IB-MECA (CF101), CP-608, 039, CP-532,903, MRS5698, MRS5980, LJ-529 33, or MRS4322. In some aspects, the 4-1BB agonist is a 4-1BB agonist antibody, recombinant 4-1B13 ligand (4-1BBL), or 4-1BB apatamer. For example, the 4-1BB agonist antibody is utomilumab or urelumab.

In some aspects, the administering is performed prior to surgical intervention. In certain aspects, the subject has not undergone surgical resection of a tumor. In some aspects, administering comprises injection of the immunogenic composition. In particular aspects, the TGFβ antagonist (or 4-1BB agonist), STING agonist, TLR7/8 agonist, RIG-I agonist, proteasome inhibitor, and adenosine A3 receptor agonist are administered as one injection. In other aspects, the TGFβ antagonist (or 4-1BB agonist), STING agonist, TLR7/8 agonist, RIG-I agonist, proteasome inhibitor, and adenosine A3 receptor agonist are administered as more than one injection. In particular aspects, the injection is an intratumoral injection.

In some aspects, the cancer is triple negative breast cancer (TNBC), PDAC, head and neck cancer, or melanoma. In some aspects, the intratumoral injection does not comprise a biomaterial, such as hydrogel or a polymer. In other aspects, the intratumoral injection does comprise a biomaterial, such as hydrogel or a polymer.

In certain aspects, the administering is more than once. In other aspects, the administering is two or more times.

In some aspects, administering results in an increase in circulating CD8+ T cells, M1 macrophages and/or tumor infiltrating dendritic cells. In specific aspects, the CD8+ T cells are $CD8^+$ IFN-$\gamma^+$ cells. In certain aspects, administering results in a durable T cell memory response as measured by an increase in $CD44^+CD127^+$ T cells as compared to $CD44^+CD127^+$ T cells prior to administration.

In certain aspects, the method does not comprise administering a cell therapy to said subject at the time the transforming growth factor beta (TGFβ) antagonist (or 4-1BB agonist), stimulator of interferon genes (STING) agonist, Toll-like receptor 7/8 (TLR7/8) agonist, RIG-I agonist, proteasome inhibitor, and adenosine A3 receptor agonist are administered, such as not being administered within 1 day, 1 week, 2 weeks, 1 month, or 3 months of the immunogenic composition. In particular aspects, the method does not comprise administering an immune checkpoint inhibitor, cytokine, and/or antigen to said subject at the time the transforming growth factor beta (TGFβ) antagonist, stimulator of interferon genes (STING) agonist, Toll-like receptor 7/8 (TLR7/8) agonist, RIG-I agonist, proteasome inhibitor, and adenosine A3 receptor agonist are administered, such as not being administered within 1 day, 1 week, 2 weeks, 1 month, or 3 months of the immunogenic composition.

In some aspects, the method further comprises administering an additional anti-cancer therapy. For example, the additional anti-cancer therapy comprises chemotherapy, radiotherapy, gene therapy, surgery, hormonal therapy, anti-angiogenic therapy or immunotherapy.

In certain aspects, the patient is a human. In some aspects, the patient has been previously administered an anti-cancer therapy.

Another embodiment provides an immunogenic composition comprising at least 4 (e.g., at least 5, 6, or 7) of the following: a transforming growth factor beta (TGFβ) antagonist, a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist. In some aspects, the composition comprises (a) a transforming growth factor beta (TGFβ) antagonist or a 4-1BB agonist and (b) at least 3 (e.g., 4 or 5) of the following: a stimulator of interferon genes (STING) agonist, a Toll-like receptor 7/8 (TLR7/8) agonist, a RIG-I agonist, a proteasome inhibitor, and an adenosine A3 receptor agonist.

In some aspects, the composition comprises a 4-1BB agonist, a stimulator of interferon genes (STING) agonist, a Toll-like receptor 7/8 (TLR7/8) agonist, a RIG-I agonist, and a proteasome inhibitor. In certain aspects, the composition comprises a transforming growth factor beta (TGFβ) antagonist, a stimulator of interferon genes (STING) agonist, a Toll-like receptor 7/8 (TLR7/8) agonist, a RIG-I agonist, and a proteasome inhibitor. In specific aspects, the composition comprises a 4-1BB agonist, a stimulator of interferon genes (STING) agonist, a Toll-like receptor 7/8 (TLR7/8) agonist, a RIG-I agonist, and an adenosine A3 receptor agonist. In particular aspects, the composition comprises a transforming growth factor beta (TGFβ) antagonist, a stimulator of interferon genes (STING) agonist, a Toll-like receptor 7/8 (TLR7/8) agonist, a RIG-I agonist, and an adenosine A3 receptor agonist. In some aspects, the composition comprises at least 5 of the following: a transforming growth factor beta (TGFβ) antagonist, a stimulator of interferon genes (STING) agonist, a Toll-like receptor 7/8 (TLR7/8) agonist, a RIG-I agonist, a proteasome inhibitor, and an adenosine A3 receptor agonist. In certain aspects, the composition comprises at least 5 of the following: a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist. In some aspects, the composition comprises a transforming growth factor beta (TGFβ) antagonist, a stimulator of interferon genes (STING) agonist, a Toll-like receptor 7/8 (TLR7/8) agonist, a RIG-I agonist, a proteasome inhibitor, and an adenosine A3 receptor agonist. In certain aspects, the composition comprises a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist.

In some aspects, the TGFβ antagonist is galunisertib (LY2157299), trabedersen, fresolimumab, LY2382770, lucanix, or PF-03446962. In certain aspects, the STING agonist is a cyclic dinucleotide or xanthenone analog. For example, the STING agonist is 2'3'-c-di-AM(PS)2 (Rp,Rp). In some aspects, the STING agonist is a cyclic dinucleotide selected from the group consisting of 3'3'-cGAMP, 2'3'-cGAMP, 2'2'-cGAMP, c-di-APM, c-di-GMP, c-di-IMP, and c-di-UMP. In certain aspects, the STING agonist is a xanthenone analog, such as 5,6-dimethylxanthenone-4-acetic acid (DMXAA). In certain aspects, the TLR7/8 agonist is resiquimod (R848), CL075, CL097, CL264, CL307, GS-9620, Poly(dT), imiquimod, gardiquimod, loxoribine or a ssRNA oligonucleotide. In certain aspects, the RIG-I agonist is 5'ppp-dsRNA, MDA5 ligand, a LGP2 ligand, a ssRNA, a dsRNA, Poly(dA:dT), or Poly(I:C). In some aspects, the proteasome inhibitor is Copper(II) Diethyldithiocarbamate, bortezomib, delanzomib, ixazomib, MG132, MG115, IPSI 001, fellutamide B, ALLN, leupeptin, epoxomicin, oprozomib, PR-957, carfilzomib, lactacystin, omuralide, salinosporamide A, salinosporamide B, a belactosine, a cinnabaramide, a polyphenol, TMC-95, or PS-519. In particular aspects, the adenosine A3 receptor agonist is 2-Chloro-N(6)-(3-iodobenzyl) adenosine-5'-N-methylcarboxamide (2-Cl-IB-MECA), IB-MECA (CF101), CP-608,039, CP-532,903, MRS5698, MRS5980, LJ-529 33, or MRS4322. In some aspects, the 4-1BB agonist is a 4-1BB agonist antibody, recombinant 4-1BB ligand (4-1BBL), or 4-1BB apatamer. For example, the 4-1BB agonist antibody is utomilumab or urelumab.

In some aspects, the subject is a human. In certain aspects, the cancer is triple negative breast cancer (TNBC), PDAC, head and neck cancer, or melanoma.

In some aspects, the composition is administered prior to surgical intervention. In certain aspects, the composition is administered by intratumoral injection. In some aspects, the intratumoral injection does not comprise a biomaterial, such as hydrogel or a polymer. In other aspects, the intratumoral injection does comprise a biomaterial, such as hydrogel or a polymer.

In certain aspects, the immunogenic composition is administered more than once. In some aspects, the immunogenic composition is administered two or more times.

In some aspects, administering the immunogenic composition results in an increase in circulating CD8+ T cells, M1 macrophages and/or tumor infiltrating dendritic cells. In certain aspects, the CD8+ T cells are $CD8^+$ IFN-$\gamma^+$ cells. In some aspects, the composition results in a durable T cell memory response as measured by an increase in $CD44^+$ $CD127^+$ T cells as compared to $CD44^+CD127^+$ T cells prior to administration.

In some aspects, the TGFβ antagonist (or 4-1BB agonist), STING agonist, TLR7/8 agonist, RIG-I agonist, proteasome inhibitor, and adenosine A3 receptor agonist are administered as one injection. In other aspects, the TGFβ antagonist (or 4-1BB agonist), STING agonist, TLR7/8 agonist, RIG-I agonist, proteasome inhibitor, and adenosine A3 receptor agonist are administered as more than one injection In certain aspects, the intratumoral injection does not comprise a biomaterial, such as hydrogel or polymer. In other aspects, the intratumoral injection does comprise a biomaterial, such as hydrogel or polymer.

In some aspects, the immunogenic composition is administered more than once. In certain aspects, the composition administered two or more times. In particular aspects, the composition does not comprise a cell therapy. In specific aspects, the composition does not comprise an immune checkpoint inhibitor, cytokine, and/or antigen.

In some aspects, the composition further comprises an additional anti-cancer therapy, such as chemotherapy, radiotherapy, gene therapy, surgery, hormonal therapy, anti-angiogenic therapy or immunotherapy.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1B) Luciferase photon intensity was cross analyzed between groups using Living Image Software to approximate total tumor burden as determined by luciferase activity. (FIG. 1C) Day 24 post-treatment image of selected treatment groups inoculated with the parent 4T-1 $luc2^{neg}$ cell line. (FIG. 1D) Tumor growth of the parent 4T-1 $luc2^{neg}$ cell line as determined by bi-weekly caliper measurement over the course of 35 days. For each experiment shown, N=5 mice per group. Representative experiment of five shown. (FIG. 1E) On post-treatment day 47, only in treatment group #13 (red circle) were all animals still alive as indicated by Kaplan-Meir survival analysis. N=5 mice per group. Representative experiment of three shown. Error bars=+/−SEM. *$p<0.05$, **$p<0.01$ by one-way ANOVA with Tukey's post-hoc.

FIGS. 2A-2F: TGF-β receptor antagonism but not repeated dosing restores efficacy of optimized treatment regimen #13 following removal of 4-1BBL. Treatment group #15 (#13 without 4-1BBL) and treatment group #16 (#15+ TGF-βR antagonist galunisertib) were introduced as rational modifications. (FIG. 2A) Cohorts of female Balb/c mice were implanted s.c. with 500,000 4T1-luc2 cells and administered intratumoral injections of treatment #15 on day 7 only, on days 7 and 10, or on days 7, 10, and 14. On post-inoculation day 16, mice were imaged by IVIS. (FIG. 2B) Tumors and tumor growth were also measured biweekly by caliper and plotted. Increasing numbers of administrations contributed to growth delay but ultimately did not impart durable tumor control. (FIG. 2C) A single intratumoral injection of treatment #15 was compared to a single intratumoral injection of treatment #16 (#15+ TGF-βR antagonism), and tumors were measured biweekly by caliper. For each experiment, N=5 animals per group. One of three representative experiments shown. (FIG. 2D) Repeated dosing of treatment #16 was able to impart durable antitumor efficacy in a dose-responsive fashion. Cohorts of female Balb/c mice were implanted s.c. with 500,000 4-T1 TNBC cells and injected intratumorally with treatment #16 on days 9, 12, and 15. Each cohort received the indicated fraction of the 1.00× (100%) treatment #16 dose. (FIG. 2E) Kaplan-Meier survival analysis of D. For each experiment D/E, N=5 animals per group. One of three representative experiments shown. (FIG. 2F) 500,000 4T-1 luc-2+ cells were implanted orthotopically under the fourth nipple of the mammary fat pad. Animals were treated intratumorally with vehicle control, a concentration of galunersitib equal to that used in the optimized regimen, a concentration of galunersitib three times that used in the optimized regimen, or the full optimized regimen 16 itself. Error bars=+/−SEM. For B-D: *$p<0.05$, **$p<0.01$ by Student's two-tailed unpaired t-test with correction for multiple comparisons. For F: *$p<0.05$, **$p<0.01$ by one-way ANOVA with Tukey's post-hoc.

(FIG. 3A) Absolute circulating $CD8^+$ T-cells per $10^6$ total cells. (FIG. 3B) Fold increase in IFN-$\gamma^+$ $CD8^+$ T-cells in comparison to untreated control. (FIG. 3C) Percent circulating exhausted CD4+ T-cells (defined as CTLA-$4^+$, PD-$1^+$). (FIG. 3D) Fold decrease in circulating regulatory $CD4^+$ T-cells (defined as CTLA-$4^+$, $Foxp3^+$) in comparison to untreated control. For each experiment A-D, red lines=group average, N=5 mice per group. One of three representative experiments shown. Error bars=+/−SEM. *p<0.05, ***p<0.005 by one-way ANOVA with Tukey's post-hoc. For characterization of memory, circulating PBMC were collected on days 20 and 35 and analyzed by flow cytometry. (FIG. 3E) Comparison of circulating $CD8^+$ $CD44^+CD127^+$ cells between vehicle control and treatment number #16 on posttreatment days 20 and 35. (FIGS. 3F/G) Visualization of individual cohort members in vehicle control and treatment groups. (FIG. 3H) Comparison of circulating $CD4^+CD44^+CD127^+$ cells between vehicle control and treatment number #16 on posttreatment days 20 and 35. (FIGS. 3I/J) Visualization of individual cohort members in vehicle control and treatment groups. For each experiment shown, red lines=group average, N=5 mice per group. One of three representative experiments shown. For E-J: Error bars=+/−SEM. *p<0.05, **p<0.01 by Student's two-tailed unpaired t-test.

(FIG. 4A) An adoptive transfer experiment was carried out as depicted in the schematic diagram. Briefly, mice inoculated with palpable TNBC tumors were treated three times with regimen #16. Thirty days following the last treatment, total splenocytes were harvested and 100,000 total splenocytes were adoptively transferred into naïve recipients. A control cohort received 100,000 splenocytes derived from uninoculated/untreated animals. Three days after adoptive transfer, recipient mice were injected intraperitoneally with 500,000 4T-1-luc2 cells and (FIG. 4B) imaged by IVIS after an additional seven days. To characterize any demonstrable abscopal effect, cohorts of female Balb/c mice were implanted s.c. with 500,000 4T-1 parent ($luc2^{neg}$) cells and injected intratumorally with regimen #16 or vehicle control on days 13, 17, and 20. On day 11, 250,000 4T1-luc2 cells were implanted s.c. at a distal site and imaged by IVIS on days 13 and 23 but were not directly treated. (FIG. 4C) Growth of the primary tumors were assessed by caliper measurement. (FIG. 4D) Growth of the untreated satellite lesions was assessed by IVIS luminescence. (FIG. 4E) IVIS images of satellite tumor burdens following treatment of primary tumor with vehicle control or regimen #16 two days and 12 days after implantation. Representative of three experiments shown, N=5 mice per group. Error bars=+/−SEM. *p<0.05 by Student's two-tailed unpaired t-test.

(FIG. 5A) Cohorts of C57BL/6 mice were implanted s.c. with 100,000 MOC-2 HNSCC cells and administered intratumoral injections of regimen 16 or vehicle control on days 7, 10, and 14. Tumor volume was determined by biweekly caliper measurement. In subsequent experiments, animals were treated twice with either vehicle or regimen 16, following which tumors were excised, digested, and analyzed by flow cytometry to determine the impact of regimen 16 on the tumor microenvironment. (FIG. 5B) A massive influx of $CD8^+$ T-cells was observed among MOC-2 MHSCC tumors treated with regimen 16 (FIG. 5C). Representative CD4/CD8 flow plot of vehicle-treated MOC-2 tumor microenvironment. (FIG. 5D) Representative CD4/CD8 flow plot of regimen 16-treated MOC-2 tumor microenvironment. All major populations of MDSC were substantially diminished among regimen 16-treated tumors including (FIG. 5E). $Gr\text{-}1^+CD11b^+$, (FIG. 5F) $Ly6c^+$ $CD11b^+$, and (FIG. 5G) $Ly6c^+Gr\text{-}1^+$. (FIG. 5H) Tumor associated $F4/80^+CD11b^+$ macrophages were also practically eliminated among regimen 16 treated tumors. (FIG. 5I) Representative F4/80 CD11b flow plot of vehicle-treated MOC-2 tumor microenvironment. (FIG. 5J) Representative F4/80 CD11b flow plot of regimen 16-treated MOC-2 tumor microenvironment. (FIG. 5K) The optimized anti-tumor regimen also induced a three-fold reduction in the number of all $CD45^+$ cells co-expressing PD-L1. Representative of three experiments shown. N=5 mice per group. Error bars=+/−SEM for A and +/−SD for bar graphs. *p<0.05, p<0.01, *p<0.005 by Student's two-tailed unpaired t-test.

(FIG. 6A) Cohorts of 129X1/SvJ mice were implanted s.c. with single cell suspensions derived from Th-MYNC tumors and administered intratumoral injections of regimen 16 or vehicle control on days 7, 10, and 14. Tumor volume was determined by caliper measurement. Circulating $CD8^+$ cell content was characterized by flow analysis following retroorbital bleed. (FIG. 6B) Representative plot of vehicle-treated PBMC. (FIG. 6C) Representative plot of regimen 16-treated PBMC. In subsequent experiments, animals were treated twice with either vehicle or regimen 16, following which tumors were excised, digested, and analyzed by flow cytometry to determine the impact of regimen 16 on the tumor microenvironment. Analyses revealed myeloid cell populations in the process of conversion from tolerogenic to inflammatory phenotypes after treatment with regimen 16. (FIG. 6D) Representative $F4/80^+$ macrophage intracellular arginase analysis of vehicle-treated Th-MYCN tumor microenvironment. (FIG. 6E) Representative $F4/80^+$ macrophage intracellular arginase analysis of regimen 16-treated Th-MYCN tumor microenvironment. (FIG. 6F) Representative $CD11b^+$ macrophage intracellular arginase analysis of vehicle-treated Th-MYCN tumor microenvironment. (FIG. 6G) Representative $CD11b^+$ macrophage intracellular arginase analysis of regimen 16-treated Th-MYCN tumor microenvironment. (FIG. 6H) Representative $CD11c^+/PD\text{-}L1^+$ cell analysis of vehicle-treated Th-MYCN tumor microenvironment. (FIG. 6I) Representative CD11 $c^+/PD\text{-}L1^+$ cell analysis of regimen 16-treated Th-MYCN tumor microenvironment. (FIG. 6J) Representative $CD11c^+/CTLA\text{-}4^+$ cell analysis of vehicle-treated Th-MYCN tumor microenvironment. (FIG. 6K) Representative $CD11c^+/CTLA\text{-}4^+$ cell analysis of regimen 16-treated Th-MYCN tumor microenvironment. Representative of three experiments shown. N=3 mice per group. Error bars=+/−SEM. ****p<0.001 by Student's two-tailed unpaired t-test.

FIGS. 7A-7C: Antagonism of tumor immunoinhibitory mechanisms alone does not impart an anti-tumor effect. (FIG. 7A) Reagent combinations injected intratumorally on day 12. (FIG. 7B) 250,000 4T-1 TNBC cells were implanted s.c. on the hind quarters of female Balb/c mice and injected intratumorally on day 12 with one of the four combinations described in (A). Tumor volume was measured by caliper every 2-3 days. (FIG. 7C) Quantitation of day 21 results. For both B and C, n=5. One of three representative experiments shown. Error bars=+/−SEM. *p<0.05 by Student's two-tailed unpaired t-test with correction for multiple comparisons.

FIGS. 8A-8C: Combinatorial agonism of three major intracellular PRR pathways (TLR, RIG-I, STING) imparts a temporary anti-tumor effect. (FIG. 8A) Reagent combinations injected intratumorally on day 12. (FIG. 8B) 250,000 4T-1 TNBC cells were implanted s.c. on the hind quarters of female Balb/c mice and injected intratumorally on day 12 with one of the four combinations described in (A). Tumor volume was measured by caliper every 2-3 days. (FIG. 8C) Quantitation of day 21 results. For both B and C, n=5. One of three representative experiments shown. Error bars=+/−SEM. *$p<0.05$ by Student's two-tailed unpaired t-test with correction for multiple comparisons.

(FIG. 10A) Absolute tumor infiltrating CD8+ T-cells per $10_6$ total cells (left axis) and fold-change in tumor infiltrating CD8+ T-cells (right axis) (FIG. 10B) Absolute tumor infiltrating regulatory CD4+ T-cells (defined as CTLA-4+, Foxp3+) per 10,000 CD45+ cells. (FIG. 10C) Percent tumor infiltrating exhausted CD4+ T-cells (defined as CTLA-4+PD-1+ of total CD4+). For each experiment shown, red lines=group average, n=5 mice per group. One of four representative experiments shown. Error bars=+/−SEM. *$p<0.05$ by one-way ANOVA with Tukey's post-hoc.

(FIG. 11A) Tumor-infiltrating dendritic cells. (FIG. 11B) M1 macrophages. (FIG. 11C) Myeloid-derived suppressor cells (MDSC). For each experiment shown, n=5 mice per group. One of four representative experiments 47 shown. Error bars=+/−SEM. *$p<0.05$ by Student's two-tailed unpaired t-test.

DESCRIPTION OF ILLUSTRATIVE EMBODIMENTS

Figures 1A, 1B:
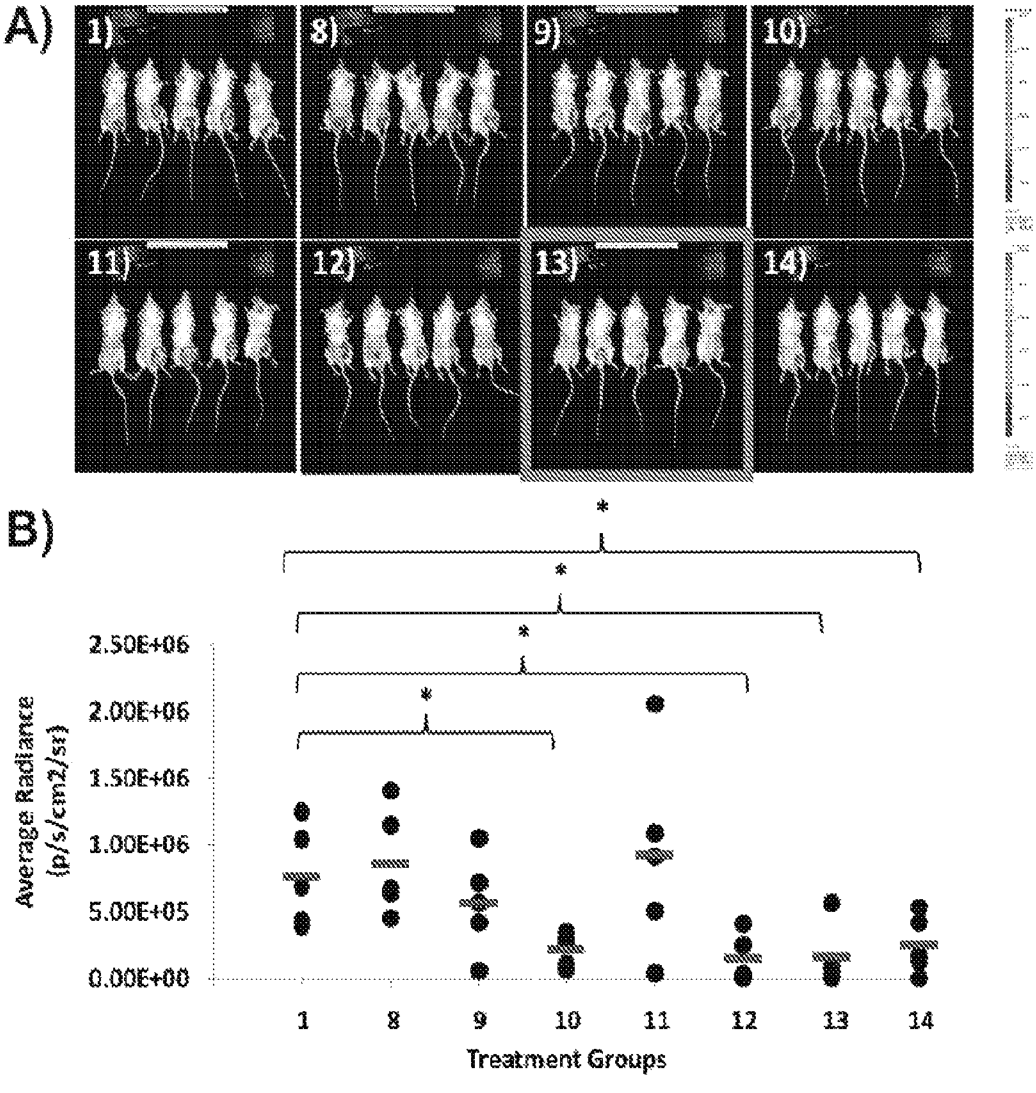
FIGS. 1A-1E: Empiric amalgams of immunomodulatory agents identifies an optimized combinatorial regimen for immunotherapy of TNBC. Cohorts of female Balb/c mice were subcutaneously implanted with 500,000 4T1-luc2 cells, and one of eight single intratumoral injections of a combinatorial immunotherapeutic treatment regimen listed in Table 1 was administered on day 7. (FIG. TA) On day 21, mice were imaged by IVIS (N=5 mice per treatment group).

To account for biological redundancy and unpredictability, the present studies sought to optimize a combinatorial approach to immunomodulation in cancer using both rational and empiric strategies. The results demonstrated that an optimized combination of intracellular pattern recognition receptor (PRR) agonists, immune inhibition antagonists, and cytostatic/damage-inducing agents could generate effective and durable anti-tumor responses in a TNBC model system generally considered to be non-immunogenic. (Brockstedt, Diagana et al., 2002, Feola, Capasso et al., 2018, Liu, Wang et al., 2018)

Tumors typically lack canonical danger signals required to activate adaptive immunity and further, also frequently employ a variety of immunomodulatory mechanisms that downregulate adaptive responses and contribute to escape from immune surveillance. Given the variety of different mechanisms involved in shielding tumors from immune recognition, it is unsurprising that single agent immunomodulatory approaches have been largely unsuccessful in generating durable antitumor responses.

Accordingly, in certain embodiments, methods and compositions are provided herein for a unique combination of immunomodulatory and cytostatic agents that recondition the tumor microenvironment and ameliorate or eliminate complex and/or poor-prognosis tumor types including the non-immunogenic 4T-1 model of TNBC, the aggressive MOC-2 model of HNSCC, and the high-risk MYCN-amplified model of neuroblastoma. A course of therapy optimized for TNBC generated a complete response rate of 50% and eliminated metastatic spread in all animals tested at the highest doses. Immune responses were transferable between therapeutic recipient and naïve donor through adoptive transfer, and a sizeable abscopal effect on distant, untreated lesions could be demonstrated experimentally. Similar results were observed in HNSCC and neuroblastoma models, with substantial remodeling of the tumor microenvironment documented in all model systems. The data indicated that the targeting of multiple pathways and mechanisms of action can result in substantial synergistic effects. These results were also shown in other cancers including PDAC and melanoma, thus, the present methods may be used for treating other non-immunogenic cancers.

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

The term "essentially" is to be understood that methods or compositions include only the specified steps or materials and those that do not materially affect the basic and novel characteristics of those methods and compositions.

As used herein, a composition that is "substantially free" of a specified substance or material contains≤30%, ≤20%, ≤15%, more preferably ≤10%, even more preferably ≤5%, or most preferably ≤1% of the substance or material.

The terms "substantially" or "approximately" as used herein may be applied to modify any quantitative comparison, value, measurement, or other representation that could permissibly vary without resulting in a change in the basic function to which it is related.

The term "about" means, in general, within a standard deviation of the stated value as determined using a standard analytical technique for measuring the stated value. The terms can also be used by referring to plus or minus 5% of the stated value.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

The term "substantially free of" is used to 98% of the listed components and less than 2% of the components to which composition or particle is substantially free of.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

All the compounds of the present disclosure may in some embodiments be used for the prevention and treatment of one or more diseases or disorders discussed herein or otherwise. In some embodiments, one or more of the compounds characterized or exemplified herein as an intermediate, a metabolite, and/or prodrug, may nevertheless also be useful for the prevention and treatment of one or more diseases or disorders. As such unless explicitly stated to the contrary, all the compounds of the present invention are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

"Prophylactically treating" includes: (1) reducing or mitigating the risk of developing the disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

The term "effective," as that term is used in the specification and/or claims, means adequate to accomplish a desired, expected, or intended result. "Effective amount," "therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

An "aggressive cancers" as referred to herein are cancers that grow and spread more aggressively and have challenges that make them more difficult to treat than common tumor types. Cancer cells can often become resistant to standard treatment options, and patients may therefore exhaust these options very quickly.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Non-limiting examples of such salts include acid addition salts formed with inorganic acids such as hydrochloric acid, hydrobromic acid, sulfuric acid, nitric acid, and phosphoric acid; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, and trimethylacetic acid. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Non-limiting examples of acceptable organic bases include ethanolamine, diethanolamine, triethanolamine, tromethamine, and N-methylglucamine. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts: Properties, and Use (P. H. Stahl & C. G. Wermuth eds., Verlag Helvetica Chimica Acta, 2002).

A "durable" antitumor response as used herein refers to a continuous response that can still prevent establishment of new tumors at least 3 months (e.g., at least 6 months, 12 months, 2 years, 3 years, 4 years, or 5 years or more) after formation or can still be adoptively transferred between subjects at least 3 months (e.g., at least 6 months, 12 months, 2 years, 3 years, 4 years, or 5 years or more) after formation.

II. IMMUNOMODULATORY AGENTS

Certain aspects of the embodiments concern immunomodulatory agents, including inhibitors and agonists of various pathways such as the TGFβ pathway and PRR pathways. In specific aspects, provided herein is a therapeutic cocktail comprising a combination of intracellular agonists, immune inhibition antagonists, and cytostatic/damage-inducing agents. The PRR agonists may comprise a STING agonist, a TLR7/8 agonist, and a RIG-I agonist. In particular aspects, the cocktail comprises a STING agonist, a TLR7/8 agonist, a RIG-I agonist, a proteasome inhibitor, and an adenosine A3 receptor agonist.

A. PRR Agonists a. STING Agonist

In some aspects, the present methods and compositions comprise a stimulator of interferon genes (STING) pathway activator, such as DDX41, STING, cGAS, IRF3, TBK1 or STAT6 or a fragment or variant thereof. STING is responsible for sensing of cytoplasmic DNA and induction of proinflammatory mediators. After binding of DNA in cytoplasm, STING activates signaling via TANK-binding kinase 1 (TBK-1)/IRF-3 axis which results in production of IFN-β. This pathway was shown to play an important role in sensing of DNA viruses as well as some autoimmune disorders. Recent data have identified STING pathway as absolutely necessary to induce spontaneous T cell priming against tumor antigens in vivo. Tumor DNA was detected within tumor-infiltrating DCs, which led to IFN-β production and T cell activation.

The present STING agonist may be selected from chemical activators of the STING pathway which are selected from cyclic dinucleotides and xanthenone analogs. Cyclic dinucleotides include but are not limited to 3'3'-cGAMP, 2'3'-cGAMP, 2'2'-cGAMP, c-di-APM, c-di-GMP, c-di-IMP, and c-di-UMP. Xanthenone analogs include but are not limited to the tumor-vascular disrupting agent 5,6-dimethylxanthenone-4-acetic acid (DMXAA; Vadimezan or ASA404). In some aspects, the STING agonist is 2'3'-c-di-AM(PS)2 (Rp,Rp), a bisphosphorothioate analog of c-di-AMP, Rp isomers (also referred to as ADU-S100 or MIW815) (CAS number: 1638750-95-4) (sodium salt).

b. TLR7/8 Agonist

In some aspects, the present methods and compositions comprise an agonist of immune stimulating toll like receptors (TLR), such as a TLR3. TLR7, TLR8 or TLR9 agonist, such as a TLR7 agonist and/or TLR8 agonist (TLR7/8). The TLR agonist may be BCG, a TLR7 agonist (e.g., poly01CLC, and imiquimod), a TLR8 agonist (e.g., resiquimod (R848), or a TLR9 agonist (e.g., CPG 7909). In some aspects, the TLR7 agonist is CL075, CL097, CL264, CL307, GS-9620, Poly(dT), imiquimod, gardiquimod, resiquimod (R848), loxoribine or a ssRNA oligonucleotide. Exemplary TLR-9 agonists include a CpG oligodeoxynucleotide (CpG ODN). Other TLR agonists are described for example in U.S. Patent Publication No. 2014/0005255; incorporated herein by reference.

c. RIG-I Agonist

In certain aspects, the present methods and composition comprise a retinoic acid inducible gene-1 (RIG-1)-like receptor ligand. In some aspects, the RIG-1-like receptor ligand is further defined as a RIG-1, MDA5, LGP2, or IPS-1 ligand.

A RIG-I-like receptor (RLR) ligand, which are known in the art, refers to activator of RIG-I, Mda5, as well as LGP2 signaling. These ligands include, but are not restricted to, single-stranded RNA, double-stranded RNA, and 5'-triphosphate RNA. RIG-I-like receptor ligand also refers to any modification introduced in an RNA molecule that can lead to binding and activation of RIG-I, Mda5, and LGP2 leading to RLR-like biological activity. In some aspects, the RLR ligand may be a modulator of common adaptor protein such as IPS-1, also known as MAVS, VISA or CARDIF. For example, the RIG-1-like receptor ligand is selected from the group consisting of a MDA5 ligand, a LGP2 ligand, a ssRNA, a dsRNA, 5'ppp-dsRNA, Poly(dA:dT), and Poly(I:C).

B. TGFβ Antagonists

Transforming growth factor beta (TGFβ) is a secreted protein that controls proliferation, cellular differentiation, and other functions in most cells. It is a type of cytokine which plays a role in immunity, cancer, bronchial asthma, lung fibrosis, heart disease, diabetes, and multiple sclerosis. TGF-γ̈ exists in at least three isoforms called TGF-β1, TGF-β2 and TGF-β3. The TGF-β family is part of a superfamily of proteins known as the transforming growth factor beta superfamily, which includes inhibins, activin, anti-millerian hormone, bone morphogenetic protein, decapentaplegic and Vg-1.

In some aspects, the TGFβ inhibitor is Galunisertib (LY2157299), trabedersen, fresolimumab, LY2382770, lucanix, or PF-03446962.

C. Proteasome Inhibitor

Proteasome is a protease complex that mediates a number of cellular mechanisms through the maintenance of optimal levels of intracellular proteins required for cell cycle progression, cell apoptosis, and normal cellular processes via ubiquitin-dependent or ubiquitin-independent degradation of proteins. Inhibition of proteasomes results in the induction of cell cycle arrest and apoptosis via modulation of several pathways including stabilization of p53, activation of C-Jun NH2-terminal kinase (JNK), and deactivation of nuclear factor kappa-B (NFκB) leading to activation of both intrinsic and extrinsic caspase cascades. Besides, inhibition of proteasome can result in the accumulation of unfolded proteins in endoplasmic reticulum (ER), subsequently activating the Unfolded Protein Response (UPR) pathway leading to apoptosis. The present proteasome inhibitor may be any proteasome inhibitor known in the art. In particular, it is one of the proteasome inhibitors described in more detail in the following paragraphs.

Proteasome inhibitors that may be used in the present methods and compositions include but are not limited to Copper(II) Diethyldithiocarbamate, (a) peptide boronates, such as bortezomib (also known as Velcade™ and PS341), delanzomib (also known as CEP-18770), ixazomib (also known as MLN9708) or ixazomib citrate; (b) peptide aldehydes, such as MG132 (Z-Leu-Leu-Leu-H), MG115 (Z-Leu-Leu-Nva-H), IPSI 001, fellutamide B, ALLN (Ac-Leu-Leu-Nle-H, also referred to as calpain inhibitor I), and leupeptin (Ac-Leu-Leu-Arg-al); (c) peptide vinyl sulfones, (d) epoxyketones, such as epoxomicin, oprozomib (also referred to as PR-047 or ONX 0912). PR-957 (also known as ONX 0914), and carfilzomib (also referred to as PR-171); and (e) β-lactones, such as lactacystin, omuralide, salinosporamide A (also known as NPI-0052 and marizomib), salinosporamide B, belactosines, cinnabaramides, polyphenols, TMC-95, and PS-519.

D. Adenosine A3 Receptor Agonist

Adenosine receptors (ARs) are G protein-coupled receptors (GPCRs) that sense an imbalance of demand and supply of energy/oxygen/nutrients. Extracellular adenosine concentrations rise in response to hypoxia and other stress, to act upon four subtypes of ARs (AIAR, A2AAR, A2BAR, and $A_3AR$). Agonists of the A1AR, A2AAR and $A_3AR$ have been the subject of preclinical and clinical evaluation (Jacobson et al., Front. Cell. Neurosci., 2019). Adenosine A(3) receptor (A3AR) is coupled to G proteins that are involved in a variety of intracellular signaling pathways and physiological functions. Exemplary $A_3AR$ agonists include but are not limited to 2-Chloro-N(6)-(3-iodobenzyl) adenosine-5'-N-methylcarboxamide (2-Cl-IB-MECA; CF102, Namodenoson), IB-MECA (CF101), CP-608,039, CP-532,903, MRS5698, MRS5980, LJ-529 33 (4'-thio-Cl-IB-MECA), and MRS4322.

E. 4-1BB Agonist

In some aspects, the present immunogenic composition comprises a co-stimulatory receptor 4-1BB agonist. 4-1BB belongs to the TNF receptor family, which includes multiple T cell co-stimulatory receptors which have been targeted with agonist antibodies including GITR, CD40, CD27, HVEM. LIGHT, APRIL, and TWEAK. Exemplary 4-1BB agonists include but are not limited to 4-1BB agonist antibodies (e.g., Utomilumab (PF-05082566) or urelumab (BMS-663513)), recombinant 4-1BBL (including but not limited to soluble, matrix-bound, scaffold bound forms), and 4-1BB aptamers.

III. METHODS OF USE

Further provided herein are methods for treating or delaying progression of cancer, such as preventing metastasis, in an individual comprising administering an immunogenic composition of the present embodiments to the individual. The composition may be administered as an intratumor injection.

Examples of cancers contemplated for treatment include lung cancer, head and neck cancer, breast cancer, brain cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, and bladder cancer. In particular aspects, the cancer is triple negative breast cancer.

The cancer may specifically be of the following histological type, though it is not limited to these: neoplasm, malignant; carcinoma; non-small cell lung cancer; renal cancer; renal cell carcinoma; clear cell renal cell carcinoma; lymphoma; blastoma; sarcoma; carcinoma, undifferentiated; meningioma; brain cancer; oropharyngeal cancer; nasopharyngeal cancer; biliary cancer; pheochromocytoma; pancreatic islet cell cancer; Li-Fraumeni tumor; thyroid cancer; parathyroid cancer; pituitary tumor; adrenal gland tumor; osteogenic sarcoma tumor; neuroendocrine tumor; breast cancer; lung cancer; head and neck cancer; prostate cancer; esophageal cancer; tracheal cancer; liver cancer; bladder cancer; stomach cancer; pancreatic cancer; ovarian cancer; uterine cancer; cervical cancer; testicular cancer; colon cancer; rectal cancer; skin cancer; giant and spindle cell carcinoma; small cell carcinoma; small cell lung cancer; papillary carcinoma; oral cancer; oropharyngeal cancer; nasopharyngeal cancer; respiratory cancer; urogenital cancer; squamous cell carcinoma; lymphoepithelial carcinoma; basal cell carcinoma; pilomatrix carcinoma; transitional cell carcinoma; papillary transitional cell carcinoma; adenocarcinoma; gastrointestinal cancer; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma with squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; lentigo maligna melanoma; acral lentiginous melanoma; nodular melanoma; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; an endocrine or neuroendocrine cancer or hematopoietic cancer; pinealoma, malignant; chordoma; central or peripheral nervous system tissue cancer; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; B-cell lymphoma; malignant lymphoma; Hodgkin's disease; Hodgkin's; low grade/follicular non-Hodgkin's lymphoma; paragranuloma; malignant lymphoma, small lymphocytic; malignant lymphoma, large cell, diffuse; malignant lymphoma, follicular; mycosis fungoides; mantle cell lymphoma; Waldenstrom's macroglobulinemia; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; chronic lymphocytic leukemia (CLL); acute lymphoblastic leukemia (ALL); Hairy cell leukemia; chronic myeloblastic leukemia; and/or hairy cell leukemia.

In some embodiments, the subject is a mammal. e.g., a primate, preferably a higher primate, e.g., a human (e.g., a patient having, or at risk of having, a disorder described herein). In one embodiment, the subject is in need of enhancing an immune response. In certain embodiments, the subject is, or is at risk of being, immunocompromised. For example, the subject is undergoing or has undergone a chemotherapeutic treatment and/or radiation therapy. Alternatively, or in combination, the subject is, or is at risk of being, immunocompromised as a result of an infection. In some aspects, the subject is a mammal. A mammal may include but is not limited to goat, cattle, swine, dog, cat, donkey, monkey, ape, a rodent such as a mouse, hamster, and rabbit.

A. Formulation and Administration

The present disclosure provides pharmaceutical compositions comprising immunomodulatory agents. Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals. One will generally desire to employ appropriate salts, buffers, and lipids to render delivery of the oligonucleotides to allow for uptake by target cells. Such methods and compositions are well known in the art, for example, as disclosed in U.S. Pat. Nos. 6,747,014 and 6,753,423, incorporated by reference herein. Compositions of the present disclosure comprise an effective amount of the oligonucleotide to cells, dissolved or dispersed in a pharmaceutically acceptable carrier or medium.

The active compositions of the present disclosure may include classic pharmaceutical preparations. Administration of these compositions according to the present disclosure will be via any common route so long as the target tissue is available via that route. Administration may be by intradermal, subcutaneous, intramuscular, intraperitoneal or intravenous injection, or introduction into the CNS, such as into spinal fluid. Such compositions would normally be administered as pharmaceutically acceptable compositions, described supra.

In particular aspects, the administration is by injection, such as intratumoral injection. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, lipids, nanoparticles, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the composition of the present disclosure may be incorporated with excipients. The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards. In some aspects, the dosage of each of the components in the immunogenic composition may be between 1× and 100× of the dose shown in Table 2. For example, the dose for the proteasome inhibitor (e.g., Copper(II) diethyldithiocarbamate) may be 120 μg to 12 mg, the adenosine A3 receptor agonist (e.g., 2-Cl-IB-MECA) may be 28 μg to 2.8 mg, the STING agonist (e.g., 2'3'-c-di-AM(PS))2 (Rp, Rp)) may be 0.50 g to 0.05 mg, the RIG-I agonist (e.g., Iyovec) may be 0.53 μg to 0.053 mg, the TLR7/8 agonist (e.g., resiquimod, R848) may be 21 g to 2.1 mg, and the TGFβ inhibitor (e.g., galuniesertib) may be 42 g to 4.2 mg, or any range derivable therein.

B. Combination Therapies

In order to increase the effectiveness of the present immunogenic compositions, it may be desirable to combine these compositions with other agents effective in the treatment of the disease of interest. In some aspects, the subject may be administered an immune checkpoint inhibitor or a vaccine. In some aspects, the subject is administered a radiotherapy or chemotherapy. In some aspects, the subject is administered targeted kinase inhibitors, such as BRAF inhibitors.

As a non-limiting example, the treatment of cancer may be implemented with an immunogenic composition of the present embodiments along with other anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the anti-cancer peptide or nanoparticle complex and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the immunogenic composition and the other includes the second agent(s).

Treatment with an immunogenic composition may precede or follow the other agent treatment by intervals ranging from minutes to weeks. In embodiments where the other agent and immunogenic composition are applied separately to the subject, one would generally ensure that a significant period of time did not expire between the time of each delivery, such that the agent and the immunogenic composition would still be able to exert an advantageously combined effect on the cell. In such instances, it is contemplated that one may contact the cell with both modalities within about 12-24 hours of each other and, more preferably, within about 6-12 hours of each other. In some situations, it may be desirable to extend the time period for treatment significantly where several days (e.g., 2, 3, 4, 5, 6 or 7 days) to several weeks (e.g., 1, 2, 3, 4, 5, 6, 7 or 8 weeks) lapse between the respective administrations.

Various combinations may be employed, where the immunogenic composition is "A" and the secondary agent, such as radiotherapy, chemotherapy or anti-inflammatory agent, is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

In certain embodiments, administration of immunogenic composition of the present embodiments to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described hyperproliferative cell therapy.

a. Chemotherapy

Cancer therapies also include a variety of combination therapies. In some aspects a immunogenic composition of the embodiments is administered (or formulated) in conjunction with a chemotherapeutic agent. For example, in some aspects the chemotherapeutic agent is a protein kinase inhibitor such as a EGFR, VEGFR, AKT, Erb1, Erb2, ErbB, Syk, Bcr-Abl, JAK, Src, GSK-3, PI3K, Ras, Raf, MAPK, MAPKK, mTOR, c-Kit, eph receptor or BRAF inhibitors. Nonlimiting examples of protein kinase inhibitors include Afatinib, Axitinib, Bevacizumab, Bosutinib, Cetuximab, Crizotinib, Dasatinib, Erlotinib, Fostamatinib, Gefitinib, Imatinib, Lapatinib, Lenvatinib, Mubritinib, Nilotinib, Panitumumab, Pazopanib, Pegaptanib, Ranibizumab, Ruxolitinib, Saracatinib, Sorafenib, Sunitinib, Trastuzumab, Vandetanib, AP23451, Vemurafenib, MK-2206, GSK690693, A-443654, VQD-002, Miltefosine, Perifosine, CAL101, PX-866, LY294002, rapamycin, temsirolimus, everolimus, ridaforolimus, Alvocidib, Genistein, Selumetinib, AZD-6244, Vatalanib, P1446A-05, AG-024322, ZD1839, P276-00, GW572016 or a mixture thereof.

Yet further combination chemotherapies include, for example, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBT-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammalI and calicheamicin omegaI1; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylomithine (DMFO); retinoids such as retinoic acid; capecitabine; carboplatin, procarbazine, plicomycin, gemcitabien, navelbine, farnesyl-protein tansferase inhibitors, transplatinum, and pharmaceutically acceptable salts, acids or derivatives of any of the above. In certain embodiments, the compositions provided herein may be used in combination with gefitinib. In other embodiments, the present embodiments may be practiced in combination with Gleevac (e.g., from about 400 to about 800 mg/day of Gleevac may be administered to a patient). In certain embodiments, one or more chemotherapeutic may be used in combination with the compositions provided herein.

b. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic composition and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

c. Gene Therapy

In yet another embodiment, the secondary treatment is a gene therapy in which a therapeutic polynucleotide is administered before, after, or at the same time as the therapeutic composition. Viral vectors for the expression of a gene product are well known in the art, and include such eukaryotic expression systems as adenoviruses, adeno-associated viruses, retroviruses, herpesviruses, lentiviruses, poxviruses including vaccinia viruses, and papiloma viruses, including SV40. Alternatively, the administration of expression constructs can be accomplished with lipid based vectors such as liposomes or DOTAP:cholesterol vesicles. All of these methods are well known in the art (see, e.g. Sambrook et al., 1989; Ausubel et al., 1998; Ausubel, 1996).

d. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatments provided herein, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present embodiments may be used in conjunction with removal of superficial cancers, precancers, or incidental amounts of normal tissue. In some aspects, tumor resection is performed after an immunogenic composition of the embodiments is administered. In some aspects, the tumor resection is performed 2, 3, 4, or 5 weeks after the tumor is treated with the present immunogenic composition.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Multifactorial Immune Modulation for Antitumor Immunity

Empiric generation of an optimized anti-tumor multimodal therapy. The literature describes an exhaustive number of signaling pathways and mechanisms, the agonism or antagonism of which may modulate the immune system and impact the growth of various tumors; however, administration of many compounds that have been reported to eliminate or inhibit important elements of tumor-associated immune suppression including clodronate (M2 macrophage depletion), epacadostat (indoleamine 2,3-dioxygenase inhibition), No-hydroxy-nor-L-arginine (selective arginase inhibition), and L-NG-monomethyl arginine acetate (L-NMMA, nitric oxide synthase inhibition) exhibited no beneficial impact on tumor growth when injected intratumorally in a 4T-1 model of TNBC (designated as regimens 2-4 in FIG. 7A-C). Moreover, combinations that contained clodronate resulted in acceleration of tumor growth observable nine days after administration to established tumors (also FIG. 7A-C). These results were somewhat surprising given the well-characterized importance of both M2 macrophages and MDSC to tumorigenesis in the 4T-1 model system. (Hamilton, Bosiljcic et al., 2014, Simpson, Templeton et al., 2012, Sinha, Clements et al., 2007, Sinha, Clements et al., 2005a, Sinha, Clements et al., 2005b) A different approach using combinations of immune agonists agents yielded marginally better results (designated as regimens 5-7 in FIGS. 8A-C). Though single agent administration of any individual PRR agonist did not significantly slow tumor growth, a combination of agonists that stimulated each of the three major intracellular PRR signaling pathways (STING, TLR, and RLR) (Krieg, 2007, Zhang, Wang et al., 2019, Zhao, Du et al., 2019) reduced tumor size by 50% nine days after intratumoral administration to established tumors (also FIGS. 8A-C). Nonetheless, though these results were encouraging, the antitumor effect observed on day 21 was not maintained at later time points, and long-term benefit was not observed from these treatment regimens.

Figures 1C, 1D:
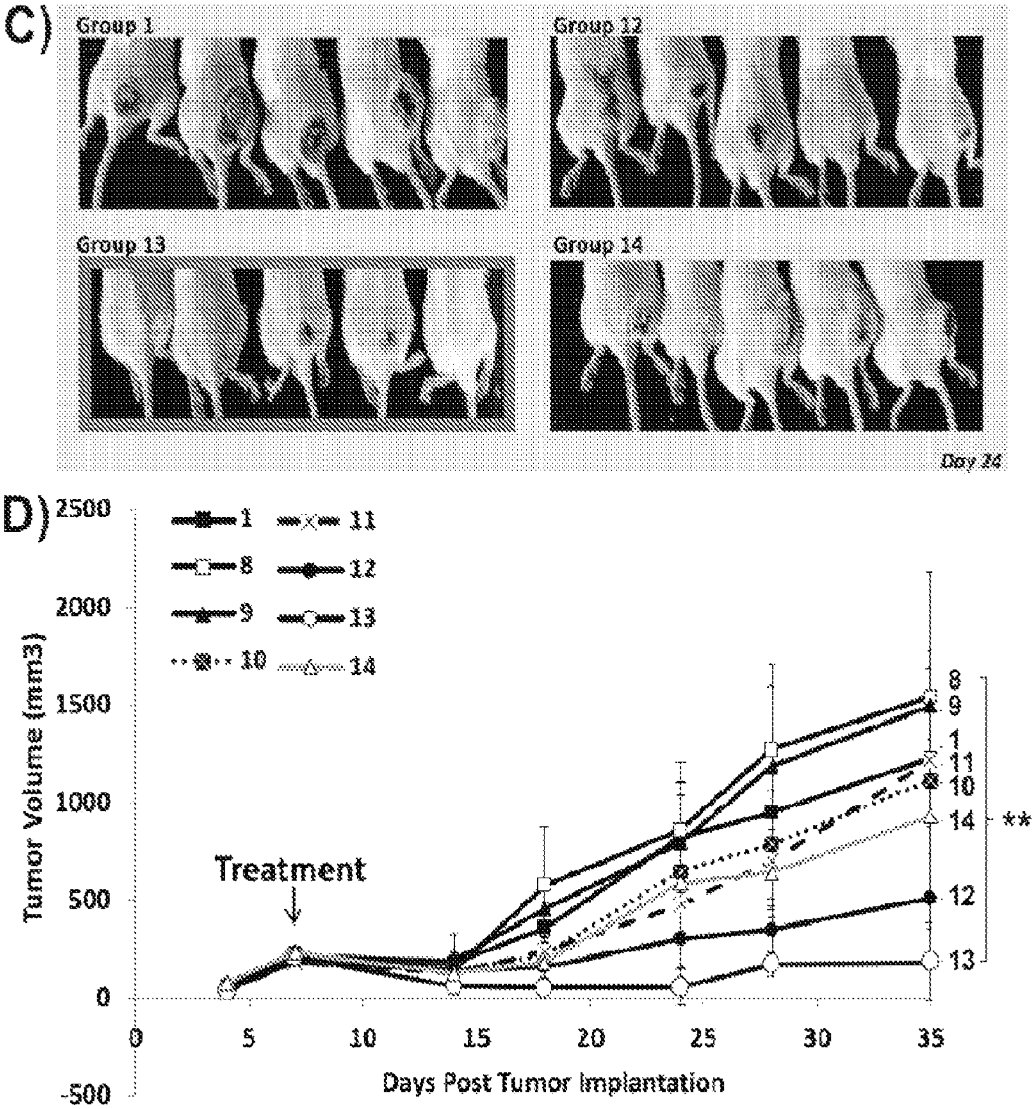
Figure 1E:
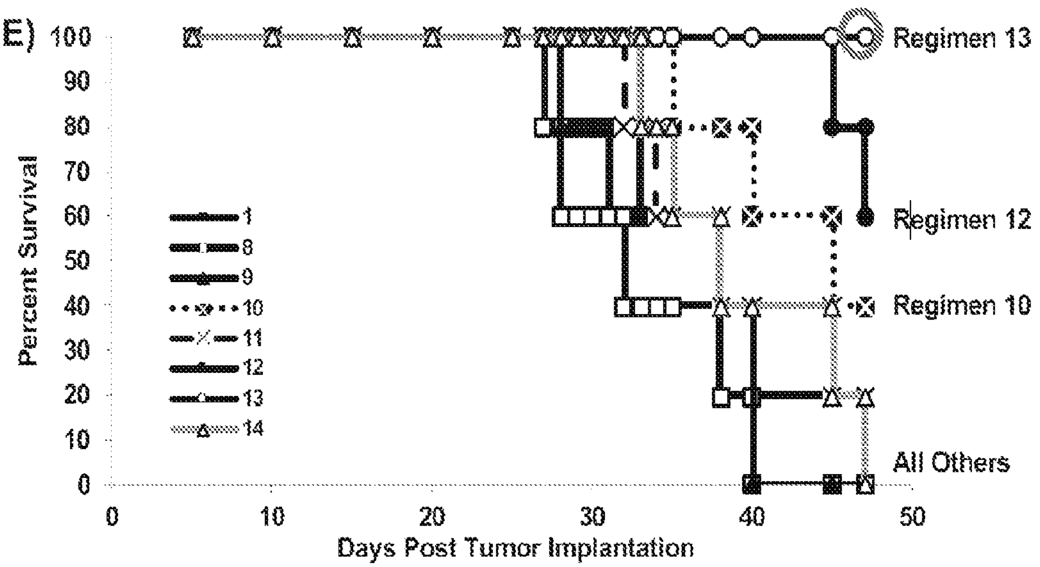

Tumors are thought to avoid immune recognition via a variety of different mechanisms related to a lack of important danger signals as well as active immune suppression through the recruitment of MDSC, macrophage polarization, and expression of immunosuppressive ligands and cytokines. (Beatty & Gladney, 2015, Vinay, Ryan et al., 2015) Therefore, it was reasoned that a viable tumor therapy should address a majority of these mechanisms and further, should also employ some type of cytotoxic agent to induce cell death, thereby generating the required antigens against which subsequent adaptive immune responses might be primed. (Galluzzi, Buque et al., 2017, Yatim, Cullen et al., 2017) To this end, three cocktails of different reagents were created, each of which addressed the three broad categories of MoA (provision of danger, inhibition of immune suppression, cytostasis/cytotoxicity) and these cocktails were combined in a variety of different ways (Table 1) prior to treatment of established 4T-1 tumors (designated as regimens 8-14 in Table 1). This both rational and empiric process identified four different combinations of agents (regimens 10, 12, 13, and 14) that significantly reduced 4T-1 tumor cell luciferase expression two weeks after administration (FIGS. 1A-B) but only two treatment combinations (regimens 12 and 13) in which tumor size still remained significantly reduced at four weeks post-administration when using the parent 4T-1 luc2$^{neg}$ cell line (FIGS. 1C-D). Use of the luc2$^{neg}$ parent was important in order to validate that immune responses might be generated against native 4T-1 antigens and not just against the xenogeneic luciferase antigen. Of these two preparations, in only one (regimen 13) were 100% of cohort members still alive at six weeks post-treatment (FIG. 1E). Consistent with the earlier data, this combination of reagents possessed no inhibitors of immunosuppression, consisting of only the three PRR agonists identified in FIG. 8 plus a 4-1BB agonist (Chester, Sanmamed et al., 2018), an adenosine A3 receptor agonist (Jafari, Panjehpour et al., 2017), and a proteasome inhibitor (Mitchell, 2003, Skrott & Cvek, 2012).

Figures 2B, 2C:
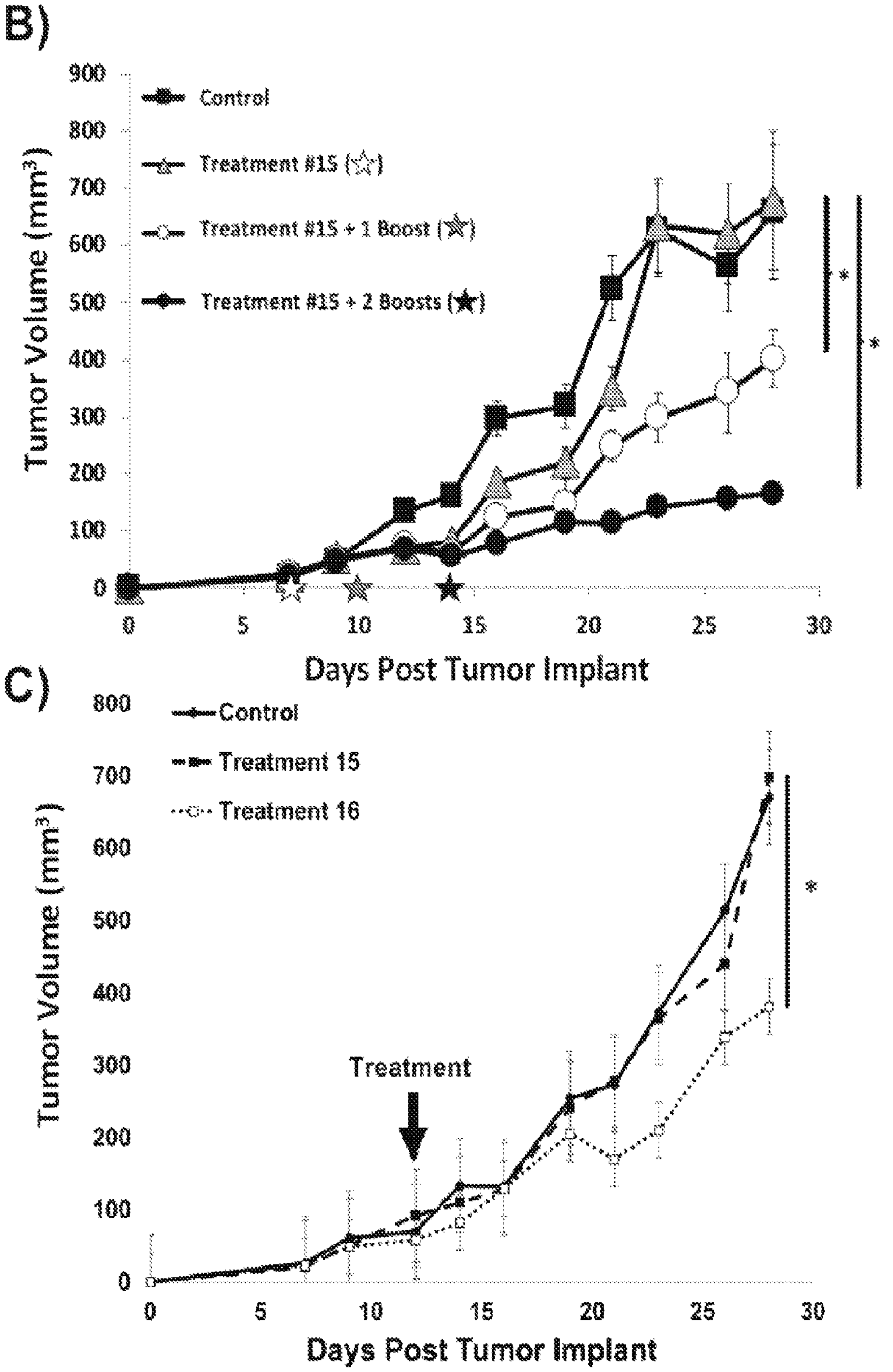

That the most efficacious regimen contained 4-1BBL was unexpected given the data in FIG. 8 indicating that the presence of 4-1BBL antagonized the anti-tumor effects of the TLR, STRING, and RLH agents. Further, 4-1BB agonism has been shown to be toxic at therapeutic doses in preclinical and early stage human clinical trials (Lee, Salek-Ardakani et al., 2009, Segal, Logan et al., 2017). Therefore the 4-1BB agonist was removed from regimen 13 (subsequently designated as regimen 15, i.e. 15=13 without the addition of 4-1BBL) and sought to reproduce equivalent efficacy through alternative rational modifications. A regimen of repeated dosing was tried, demonstrating that three doses imparted greater efficacy than two, and two better than one (FIGS. 2A-B); however, even three doses of regimen 15 did not recapitulate the efficacy of the original regimen 13 preparation possessing 4-1BBL. TGF-β is known to be one of the most important immunosuppressive cytokines in the tumor microenvironment that can mediate tumor escape from immune surveillance (Batlle & Massague, 2019), and inhibition of TGF-β signaling has previously been shown to be active against TNBC in mouse xenograft models (Bhola, Balko et al., 2013) and has also shown clinical benefit in early stage human trials (Rodon, Carducci et al., 2015). Given these observations, a single dose of the preparation lacking 4-1BB agonism (regimen 15) was next compared with a single dose of a regimen containing the TGF-β kinase signaling inhibitor galunisertib (regimen 16). This modification resulted in a substantial increase in efficacy (FIG. 2C).

Figures 2D, 2E:
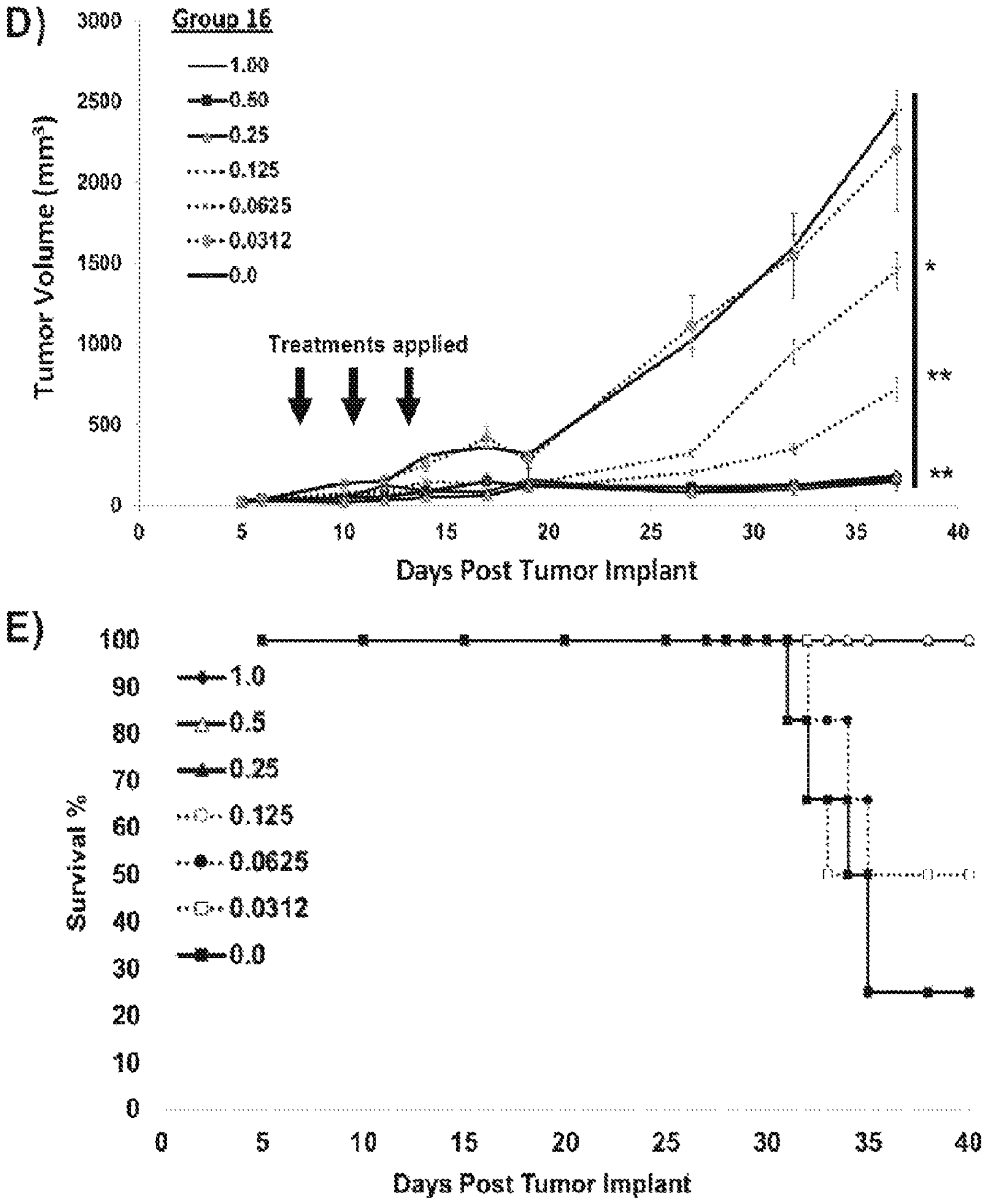
Figure 2F:
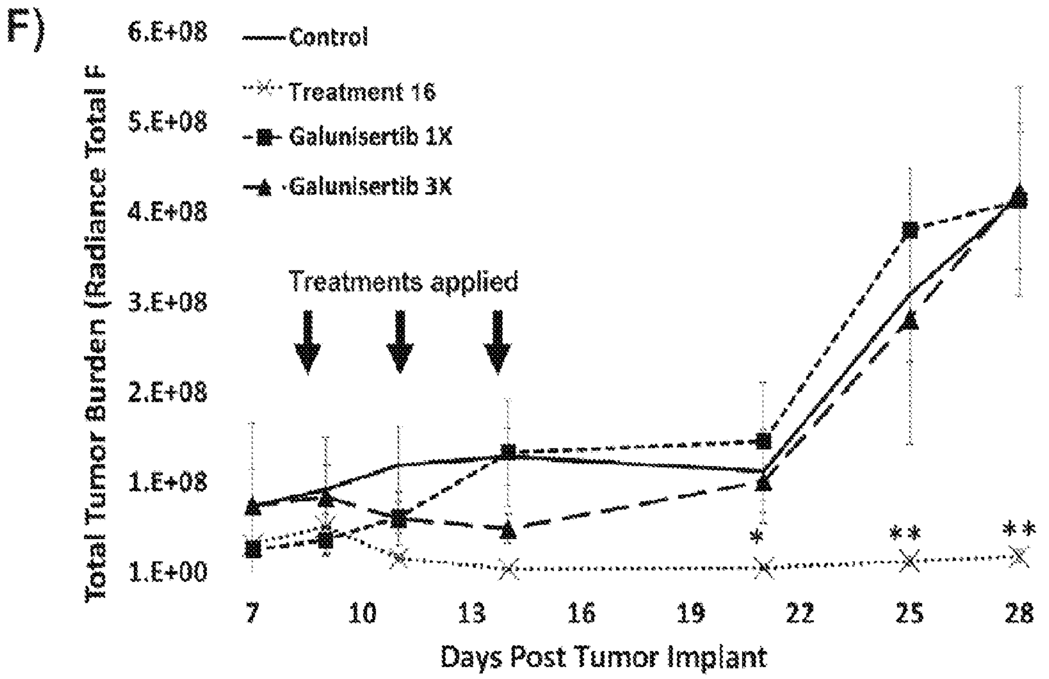
Figure 9:
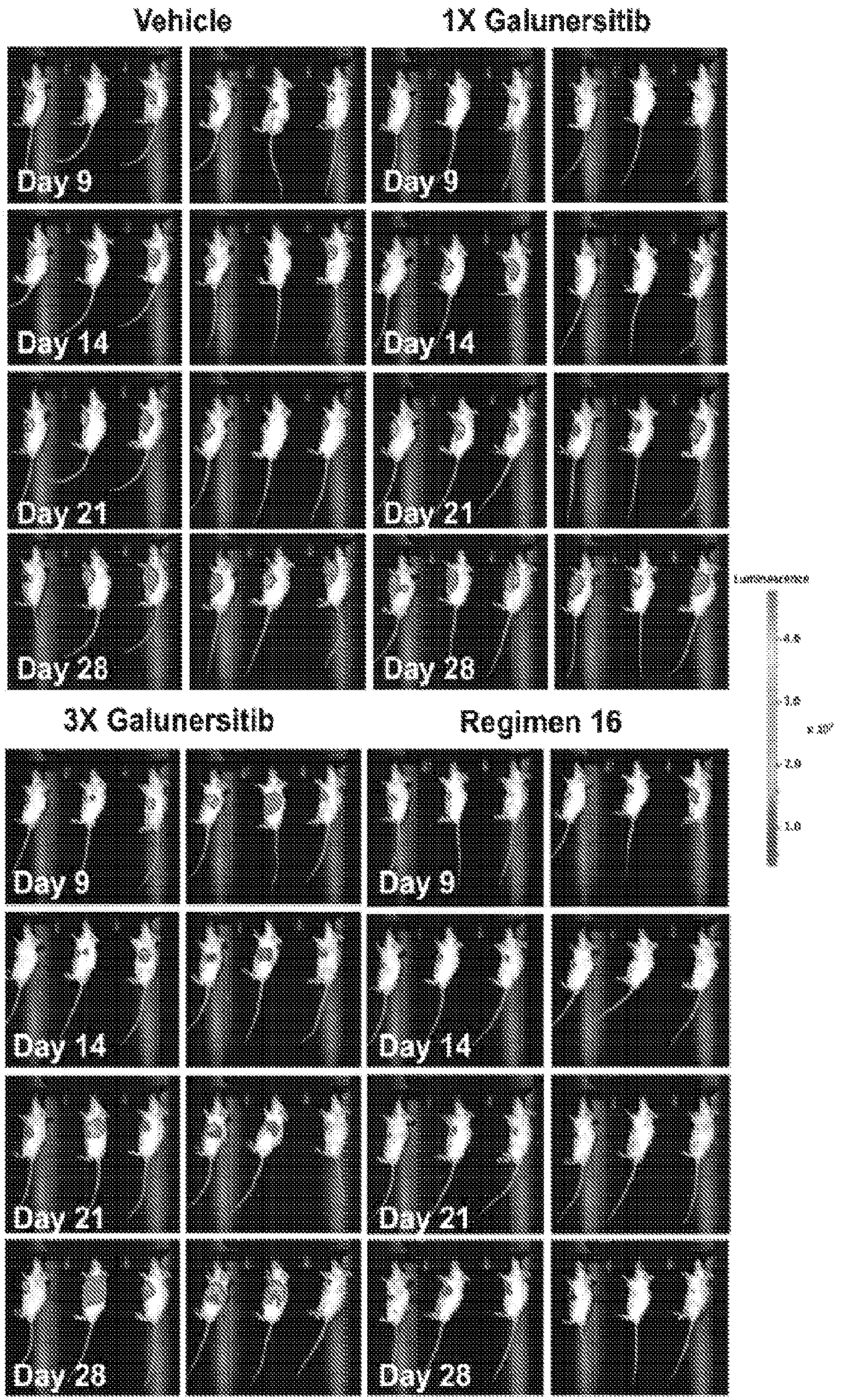
FIG. 9: Optimized regimen 16 resolves orthotopic TNBC. 500,000 4T-1 luc-2+ cells were implanted orthotopically under the fourth nipple of the mammary fat pad. Animals were treated intratumorally with vehicle control, a concentration of galunersitib equal to that used in the optimized regimen, a concentration of galunersitib three times that used in the optimized regimen, or the full optimized regimen 16 24 itself. Shown: IVIS imaging of individual animals comprising the data shown in FIG. 2F. N=6 animals per group.

Lastly, the boosting regimen was combined together with regimen 16 and performed a dose response analysis at 1×, 0.5×, 0.125×, 0.0625×, and 0.03125× concentrations. As indicated in FIGS. 2D-E, both the 1× and 0.5× doses of regimen 16 imparted significant inhibition of tumor growth, resulting in durable cure of 50% of mice at the 1× and 25% of mice at the 0.5× dose levels. The 0.125× and 0.0625× doses imparted intermediate levels of tumor control, whereas the 0.03125× dose produced an effect indistinguishable from that of vehicle control. Similar to the experiment outlined in FIGS. 1C-D, this experiment was performed with the 4T-1 luc2$^{neg}$ parent cell line to validate that protective immune responses were not dependent upon the presence of xenogeneic luciferase. The treatment model was next validated in the orthotopic setting (Zhang et al., 2019). In this series of experiments, 500,000 4T-1 luc-2$^{+}$ cells were implanted under the fourth nipple of the mammary fat pad. Animals were randomized on post-implantation day 7 and treated intratumorally with vehicle control, a concentration of galunersitib equal to that used in the optimized regimen, a concentration of galunersitib three times that used in the optimized regimen, or the full optimized regimen 16 itself. As shown in FIG. 9 and FIG. 2F, treatment regimen 16 imparted results in the orthotopic setting identical to those observed ectopically. In addition, galunersitib alone was shown to have no impact on tumor growth. Treatment regimen 16 (components listed in FIG. 2C) given intratumorally as a three-dose regimen was henceforth considered to be the final optimized regimen for subsequent characterization in multiple model systems.

Figure 3A:
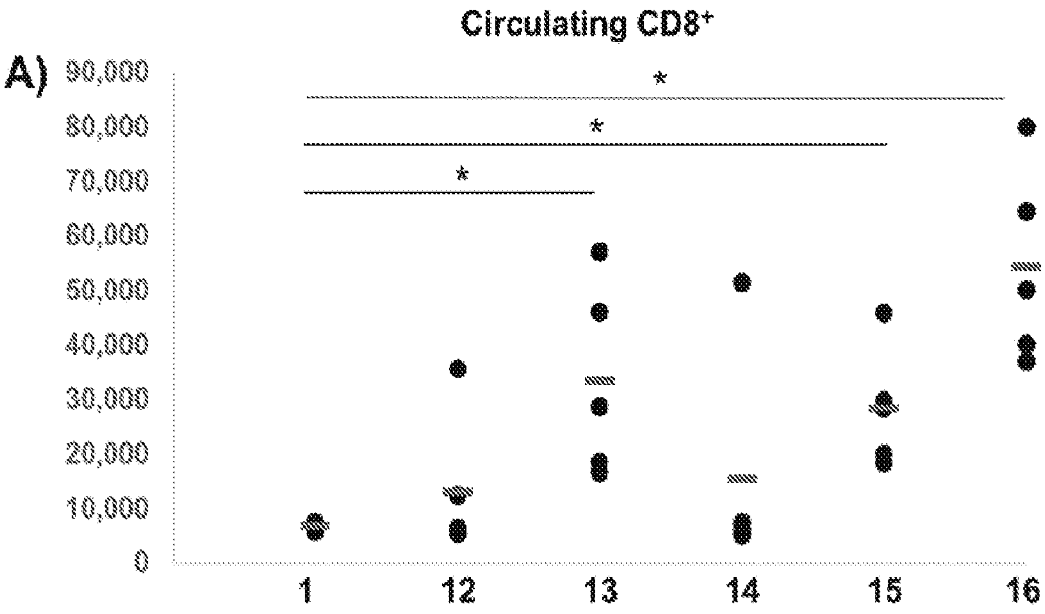
FIGS. 3A-3J: Tumor treatment with regimen #16 generates elevated levels of circulating $CD8^+$IFN-$\gamma^+$ T-cells and memory T-cells with significant reduction of exhausted and regulatory $CD4^+$ T-cells. Cohorts of Female Balb/c mice were implanted s.c. with 500,000 4T-1 cells and each group was treated intratumorally with treatments 12-16 (all at dose level 1.00) on days 9 and 12, and circulating PBMC were analyzed on day 15 via retroorbital bleed and flow cytometry.
Figure 3B:
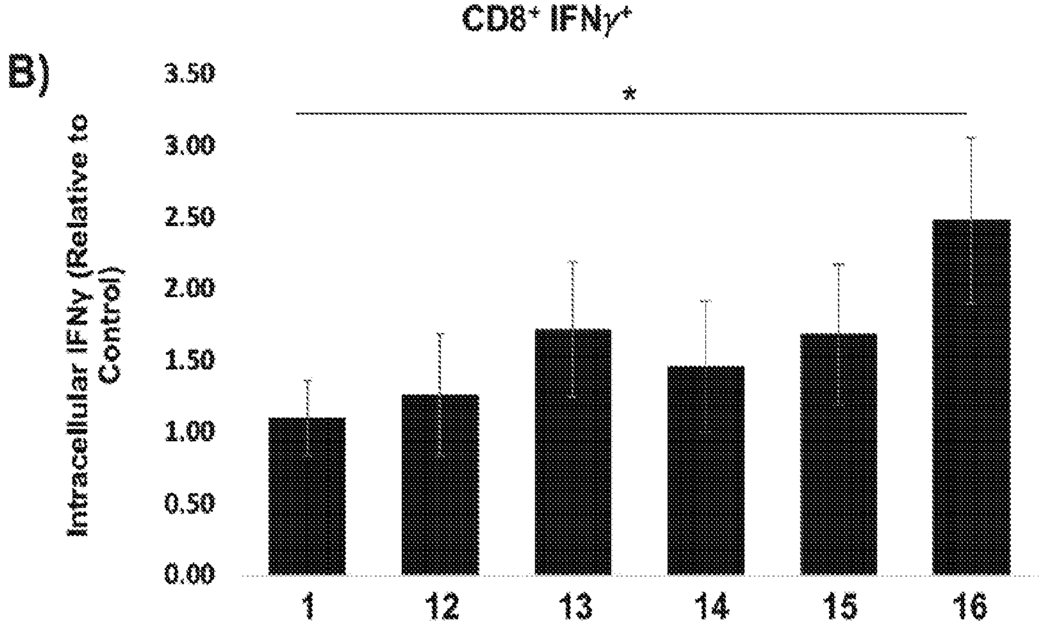
Figure 3C:
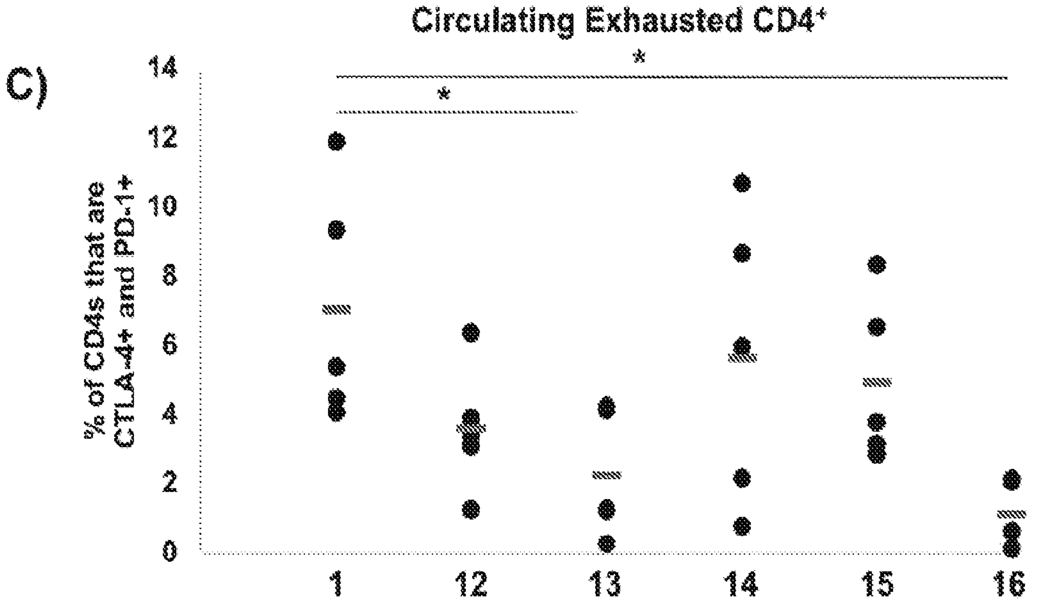
Figure 3D:
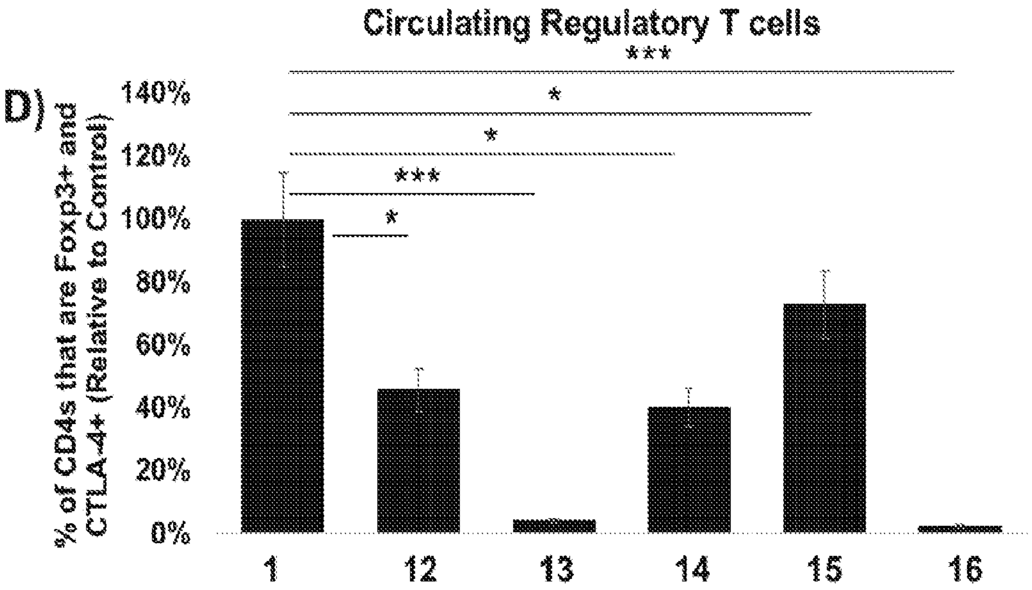
Figures 3E, 3F, 3G, 3H:
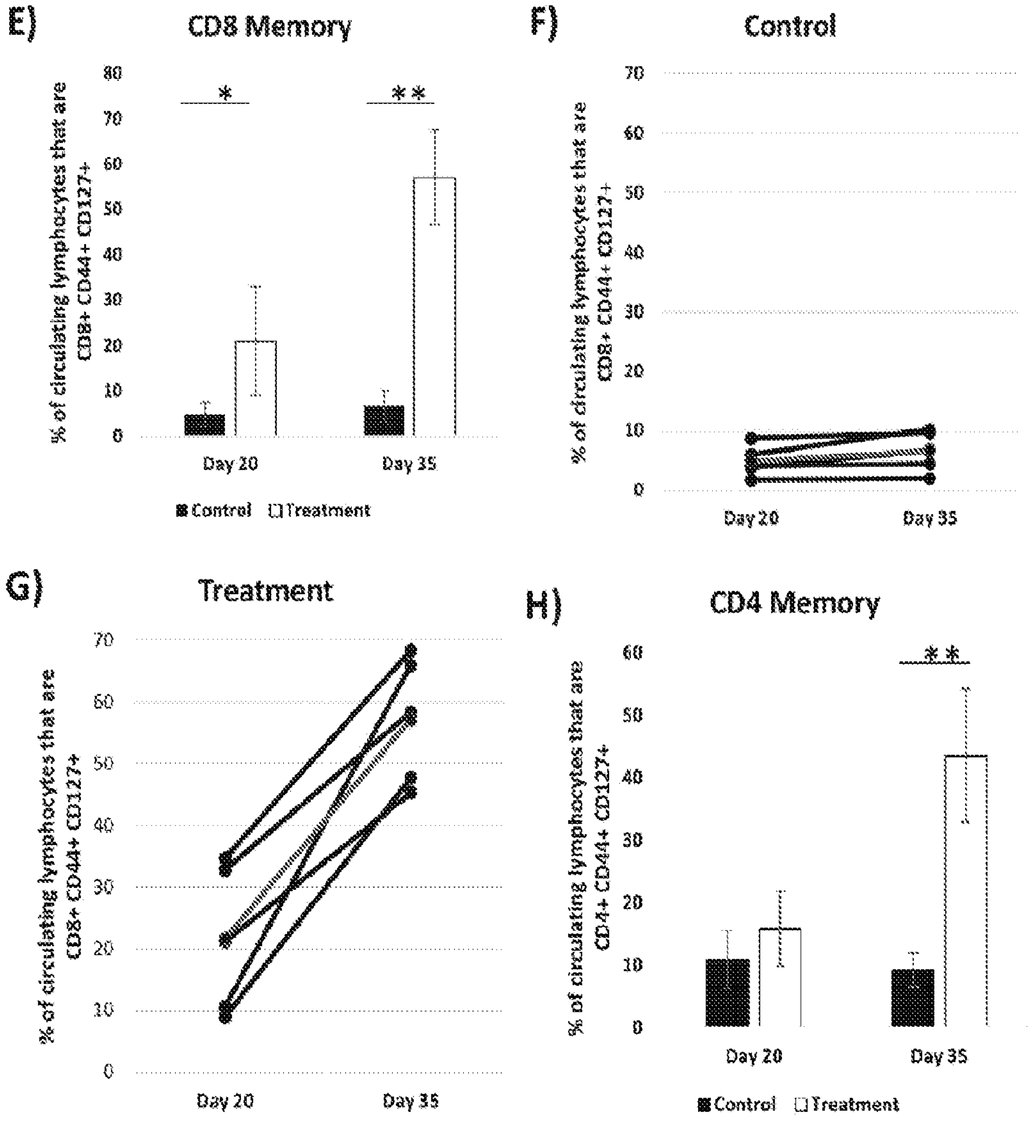
Figures 3I, 3J:
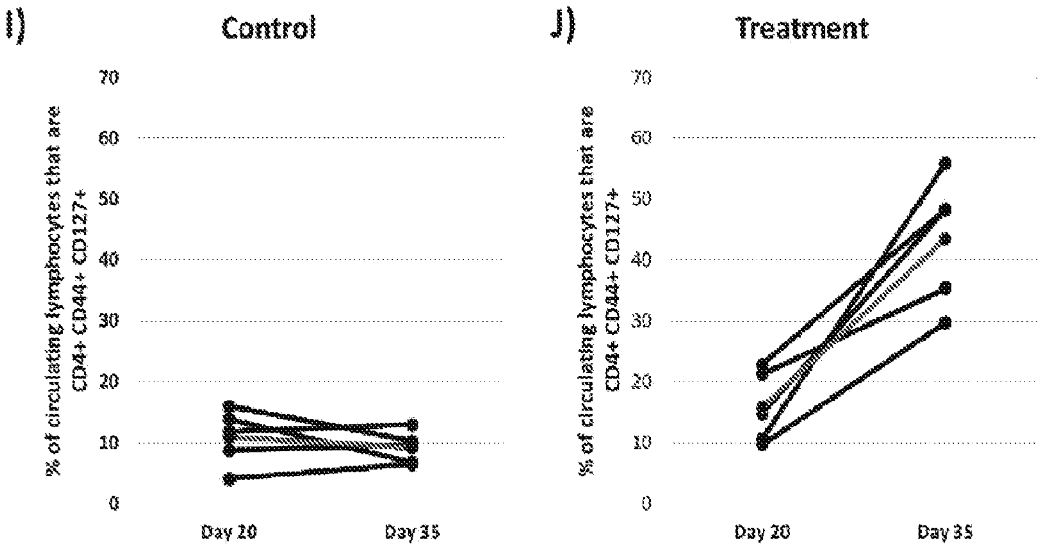
Figures 10A, 10B, 10C:
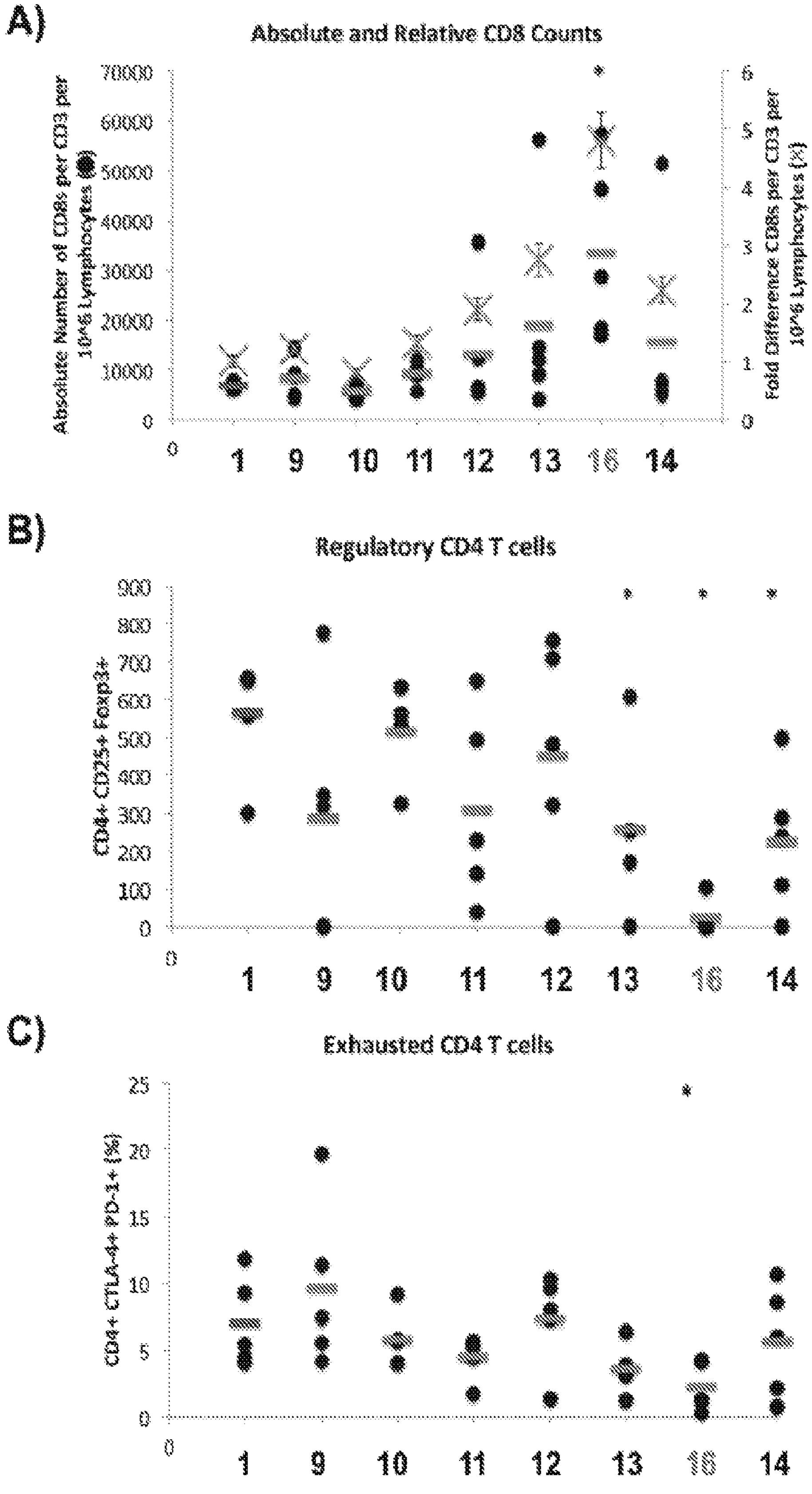
FIGS. 10A-10C: Tumor treatment with preparation #16 generates elevated levels of tumor resident CD8+IFN-g+ T-cells with significant reduction of exhausted and regulatory CD4+ T-cells. Cohorts of Female Balb/c mice were implanted s.c. with 500,000 4T-1 cells and each group was treated intratumorally with treatments 9-16 (all at dose level 1.00) on days 9 and 12, and circulating PBMC were analyzed on day 15 via retro-orbital blood draw and flow cytometry. On day 15, the tumors were excised, and the tumor microenvironment was analyzed.
Figures 11A, 11B, 11C:
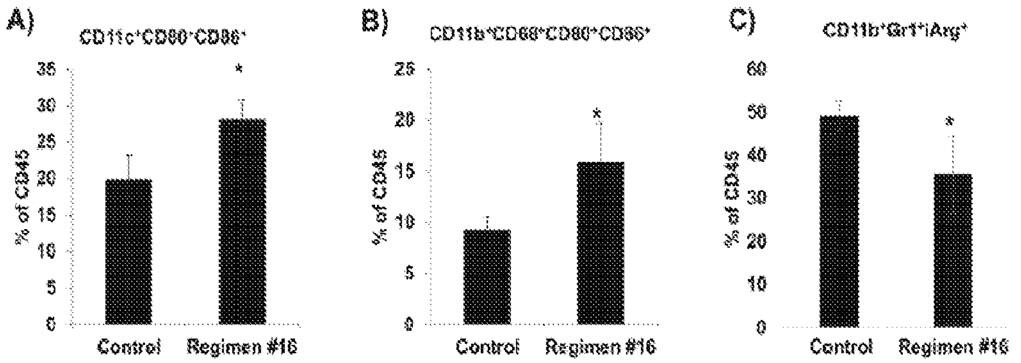
FIGS. 11A-11C: Intratumoral injection of optimized regimen 16 skews the tumor microenvironment towards a proinflammatory phenotype in TNBC. Cohorts of female Balb/c mice were inoculated s.c with 500,000 4T-1 cells, and each group was injected intratumorally with #16 on days 9 and 12. On day 15, the tumor was excised and the microenvironment analyzed as described.
Figure 12:
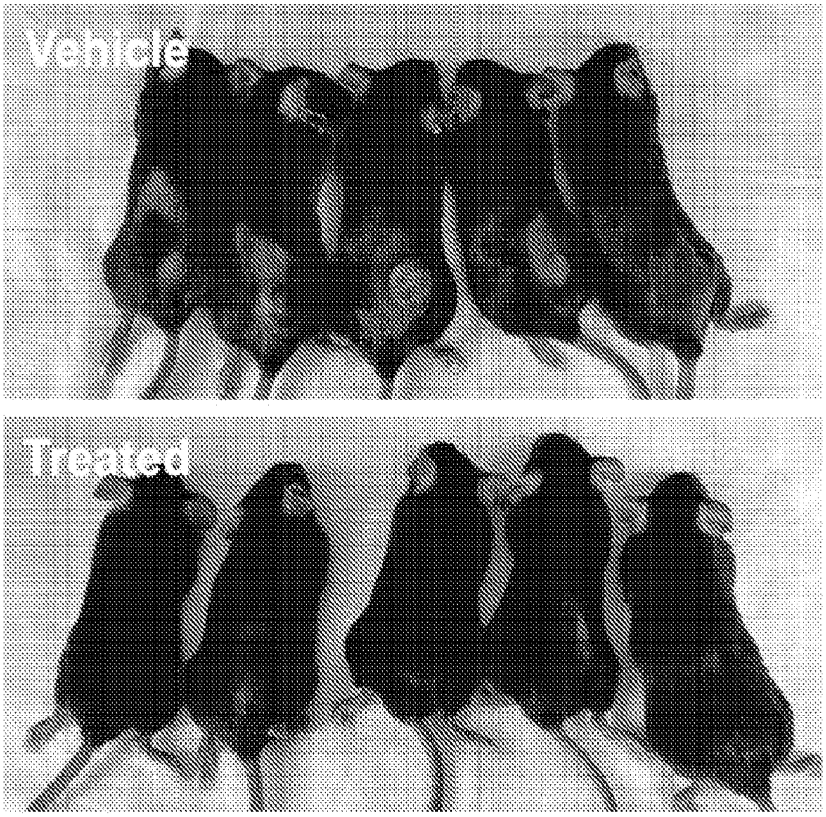
FIG. 12: Optimized regimen 16 resolves aggressive MOC-2 HNSC. Cohorts of C57BL/6J mice were implanted subcutaneously with 100,000 MOC-2 HNSCC cells. Animals were treated intratumorally with vehicle control or optimized regimen 16, and tumor volume was determined by caliper measurement. Shown: individual animals comprising the data shown in FIG. 5A.

Impact of the optimized treatment regimen on the 4T-1 TNBC tumor microenvironment. It was next sought to characterize the impact of the optimized treatment regimen on the immune system and tumor microenvironment. Established 4T-1 tumors were treated with optimized regimen 16, retreated three days later, and analyzed three additional days after the second treatment. Animals were bled retroorbitally and optimized regimen 16 was compared not only to vehicle control but also to suboptimal regimens 12-15. In comparison to vehicle control, the optimized regimen induced a seven-fold increase of circulating $CD8^+$ T-cells whereas the next best regimens (13 and 15) induced only a 3-4 fold elevation (FIG. 3A) and the others, practically no effect at all. Elevation of circulating $CD8^+$ numbers induced by regimen 16 was accompanied by a significant 2.5-fold increase in $CD8^+IFN\text{-}\gamma^+$ cells whereas no other treatment group statistically differed from vehicle control (FIG. 3B). In addition, both regimens 13 and 16 virtually eliminated circulating exhausted CD4+ and regulatory T-cells (FIGS. 3C-D). Results were similar within the tumor microenvironment in which regimen 16 induced the highest numbers of tumor-infiltrating $CD8^+$ cells with a substantial reduction in tumor-infiltrating exhausted $CD4^+$ cells and a virtual elimination of Tregs (FIGS. 10A-C). Circulating PBMC in mice given optimized regimen 16 also exhibited a significant, prolonged expansion of $CD44^+CD127^+$ T-cells in both the CD8+(FIGS. 3E-G) and CD4+(FIGS. 3H-J) compartments, indicating development of a durable T-cell memory response (Boettler, Panther et al., 2006, Huster, Busch et al., 2004). The development of this memory phenotype was anticipated by the reduction of $CD4^+CD25^+Foxp3^+$ regulatory T-cells and $PD\text{-}1^+CD4^+$ exhausted T-cells in both the tumor microenvironment and in peripheral circulation (Boettler et al., 2006, Liu, Putnam et al., 2006). A comparison of the myeloid cell compartments among optimized treatment and vehicle control also yielded significant results in resolving 4T-1 tumors. In this analysis there was a significant increase of $CD11c^+CD80^+CD86^+$ tumor infiltrating dendritic cells and $CD11b^+CD68^+CD80^+CD86^+$ M1 macrophages along with a significant decrease of an MDSC population defined as $CD11b^+Gr\text{-}1^+$ $Arginase^+$ among animals treated with optimized regimen 16 (FIGS. 11A-C).

Figures 4A, 4B:
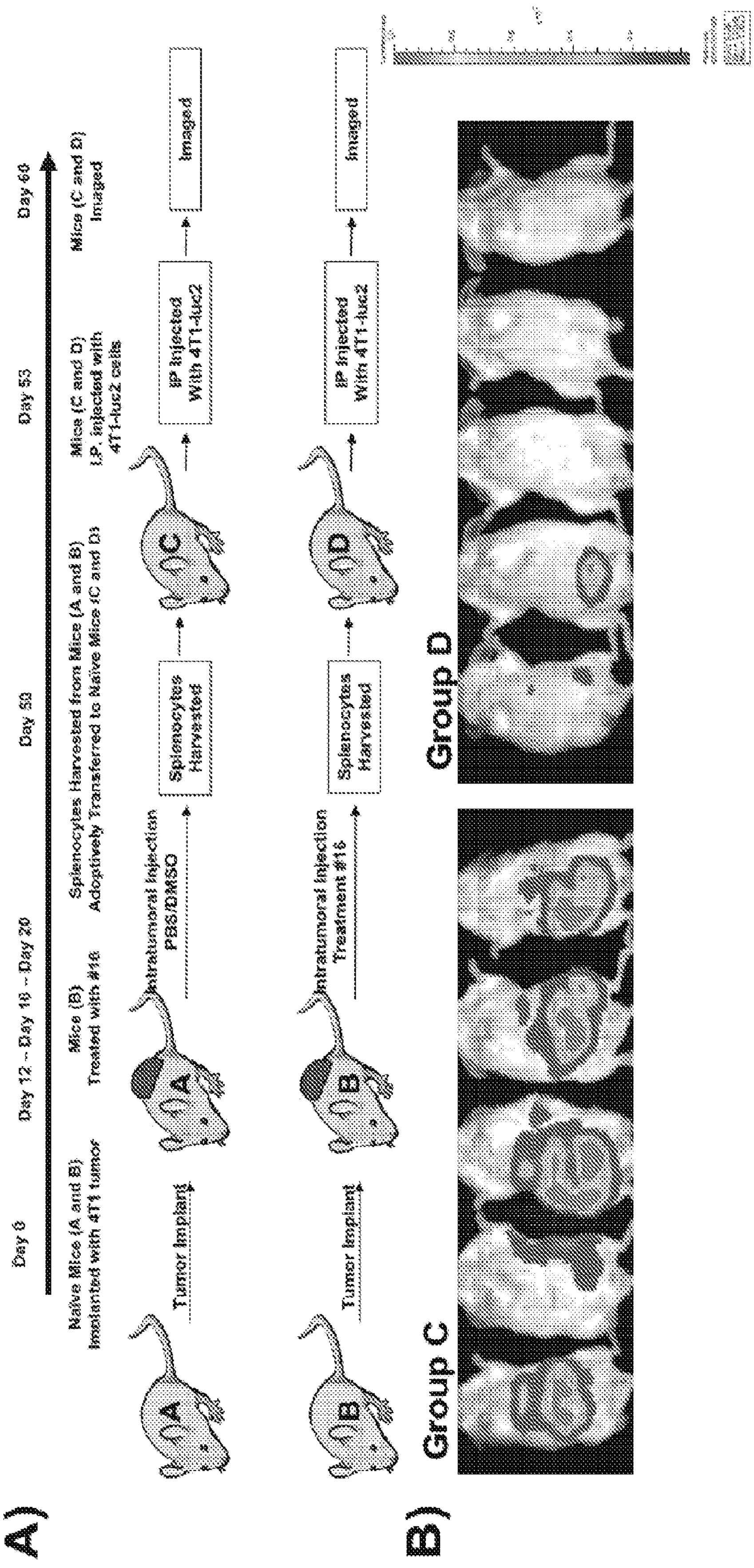
FIGS. 4A-4E: TNBC intratumoral injection with regimen #16 generates transferable memory and propagates the abscopal effect.
Figures 4C, 4D:
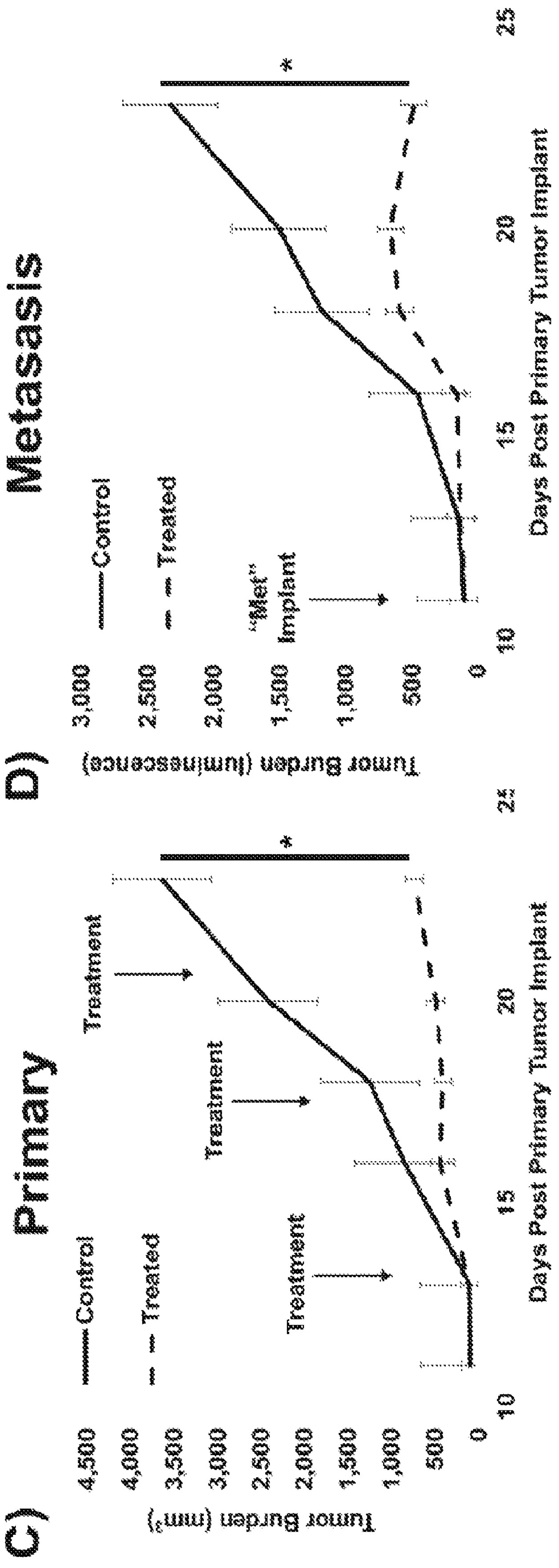
Figure 4E:
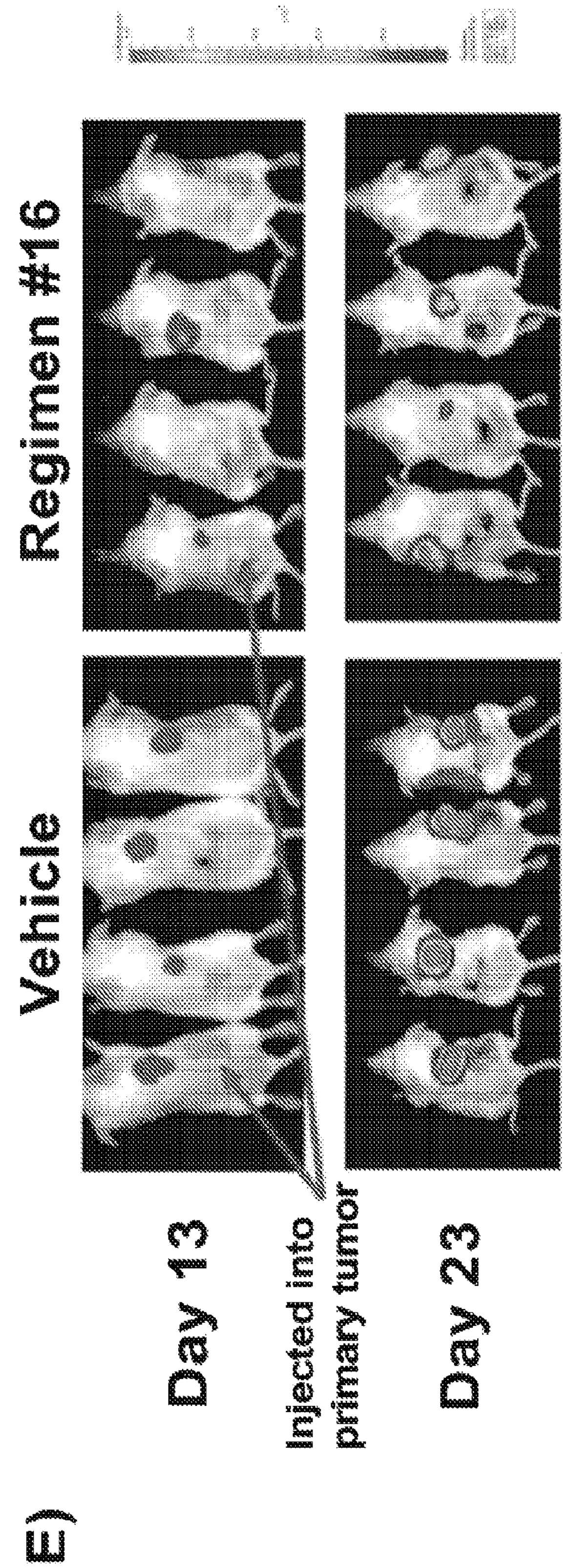

Impact of the optimized treatment regimen on the development of memory. To validate the existence of durable memory, mice were implanted with 4T-1 tumors and treated with optimized regimen 16 on post-implantation days 12, 16, and 20. Thirty days later (post-implantation day 50), splenocytes were harvested from the treated mice and adoptively transferred to a naïve cohort. A control group was adoptively transferred with splenocytes harvested from tumor-inoculated mice injected intratumorally with only vehicle control. Three days later, mice were injected intraperitoneally with 500,000 4T-1-luc2 cells, and seven days later both cohorts were imaged. As shown in FIG. 4A-B, the mice adoptively transferred with cells derived from treated animals were able to clear the large i.p. bolus of tumor, whereas mice adoptively transferred with naïve splenocytes grew large abdominal masses. The ability of antitumor immunity to be adoptively transferred from T-cell splenocyte populations suggested the potential for an abscopal effect within treated animals. To determine if treatment with the optimized tumor preparation was able to impart an abscopal effect, mice were implanted with a "primary" $luc2^{neg}$ 4T-1 tumor and a "secondary" $luc2^+$ "metastasis". This experimental design was important to demonstrate that any immune responses controlling the growth of non-treated "metastases" were derived from native 4T-1 antigens and not against the xenogeneic luciferase antigen. Additionally, implantation of $luc2^{neg}$ tumors to serve as metastatic lesions allowed experimental kinetics to proceed with even temporal kinetics in all mice without relying upon the randomness of spontaneous metastatic spread. The "primary" $luc2^{neg}$ tumor was then treated with the optimized treatment regimen on post-implantation days 13, 17, and 20. The $luc2^+$ "metastasis" was imaged at baseline on day 13 and again on day 23. As shown in FIG. 4C-E, among mice in which the primary $luc2^{neg}$ tumor was treated, the untreated $luc2^+$ lesion exhibited a six-fold reduction in size in comparison to $luc2^+$ lesions in mice on which the primary tumor was treated with vehicle control, indicating generation of a demonstrable abscopal effect.

Figures 5A, 5B:
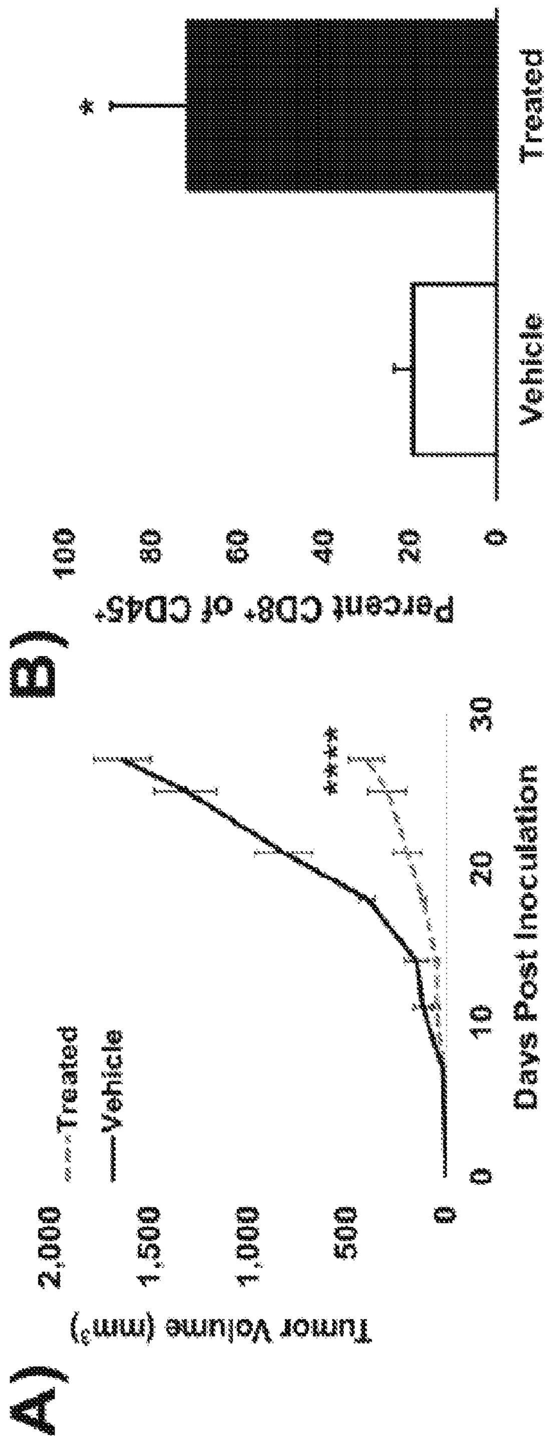
FIGS. 5A-5K: Optimized treatment regimen 16 remodels the tumor microenvironment and ameliorates aggressive MOC-2 HNSCC.
Figures 5C, 5D:
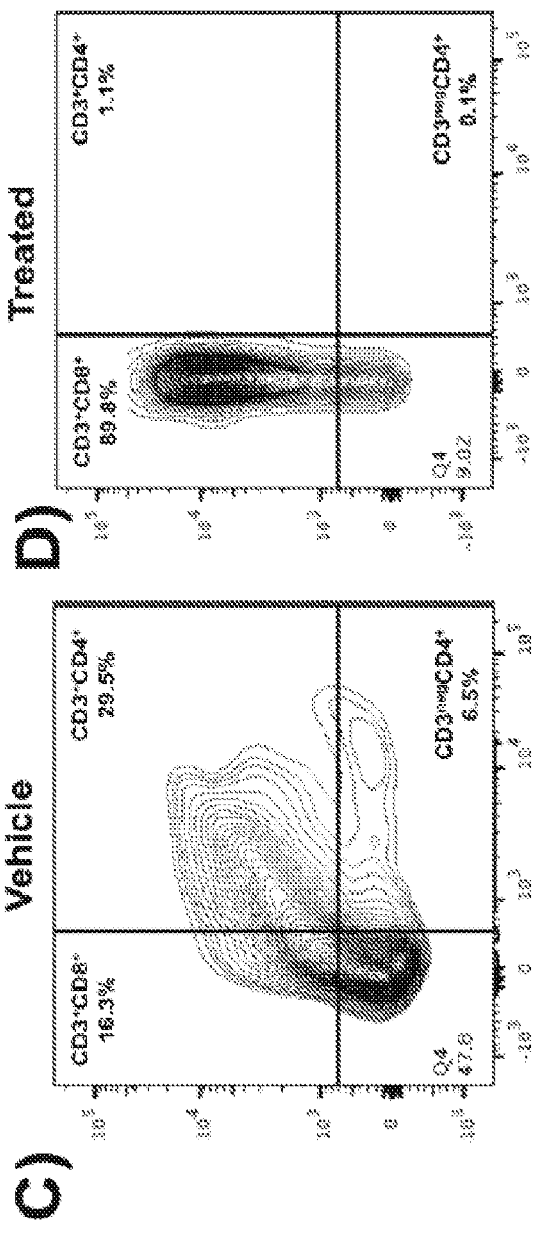
Figures 5E, 5F, 5G:
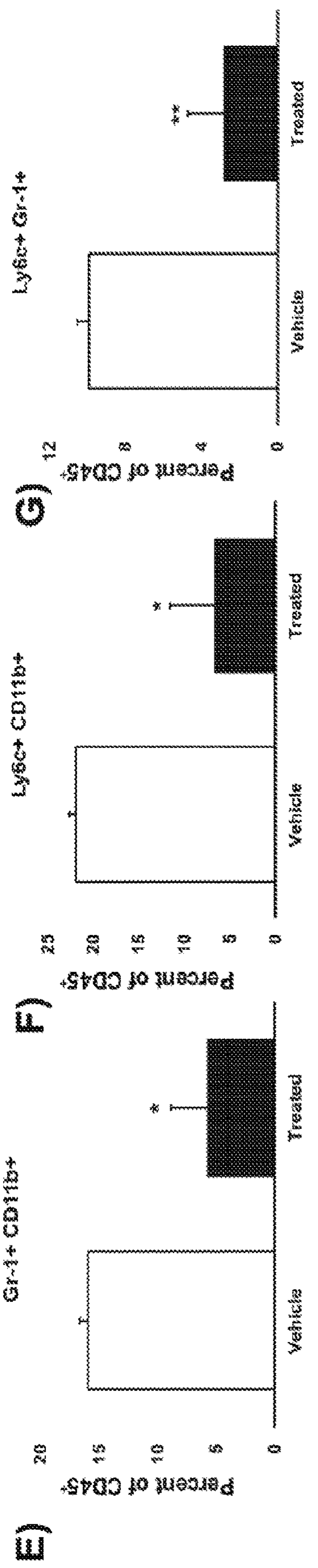
Figures 5H, 5I, 5J:
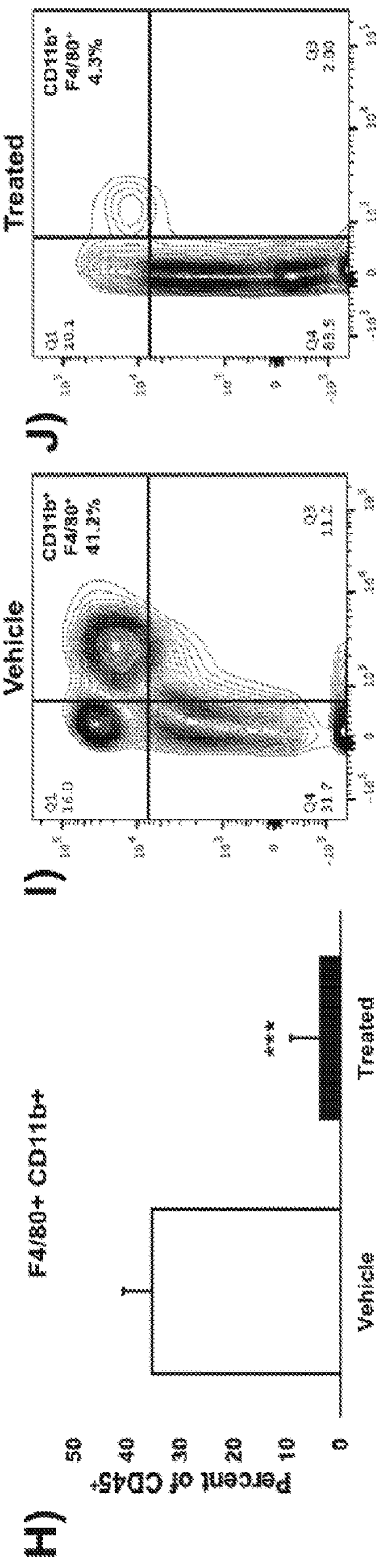
Figure 5K:
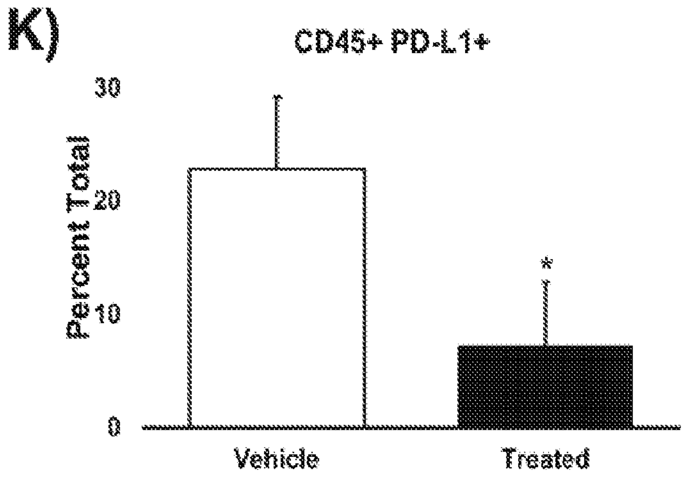

Impact of the optimized regimen in other hard-to-treat model systems. To determine if the optimized treatment regimen might be applicable in hard-to-treat or non-immunogenic model systems other than TNBC, series of experiments were repeated in a cohort of animals implanted subcutaneously with the aggressive HNSCC MOC-2 cell line. As shown in FIG. 5A and FIG. 11, treatment of MOC-2 HNSCC with optimized regimen 16 led to dramatic reduction in volume or full resolution of these tumors. In subsequent experiments, animals were treated twice with either vehicle or regimen 16, following which tumors were excised, digested, and analyzed by flow cytometry to determine the impact of regimen 16 on the tumor microenvironment. In these experiments, a massive influx of $CD8^+$ T-cells was observed among tumors treated with regimen 16 (FIGS. 5B-D). In addition, all major populations of MDSC were substantially diminished (FIGS. 5E-G) as were tumor associated macrophages which were practically eliminated (FIGS. 5H-J) among tumors treated with regimen 16. The optimized anti-tumor regimen also induced a three-fold reduction in the number of all $CD45^+$ cells co-expressing PD-L1 (FIG. 5K).

Figure 6A:
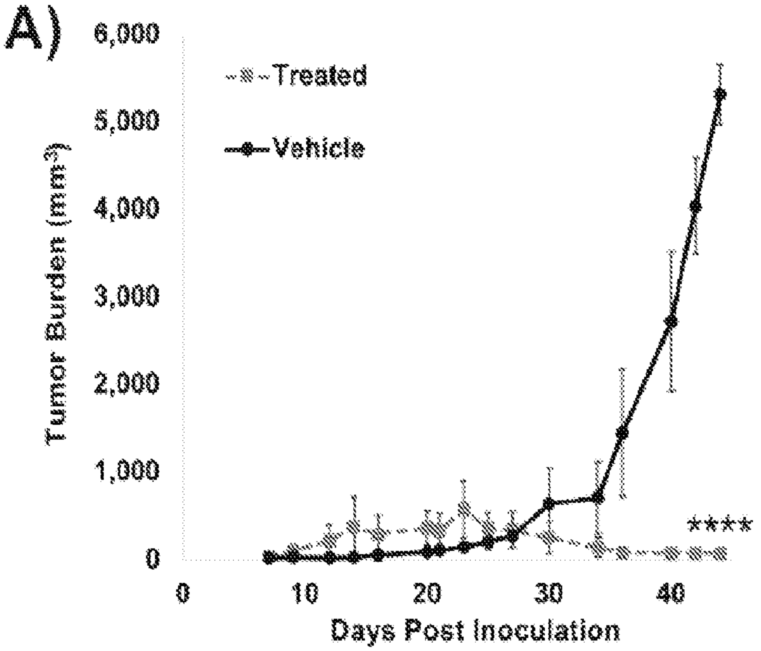
FIGS. 6A-6K: Optimized treatment regimen 16 resolves MYCN-amplified neuroblastoma and induces de-differentiation of tolerogenic myeloid cells.
Figures 6B, 6C, 6D, 6E, 6F, 6G:
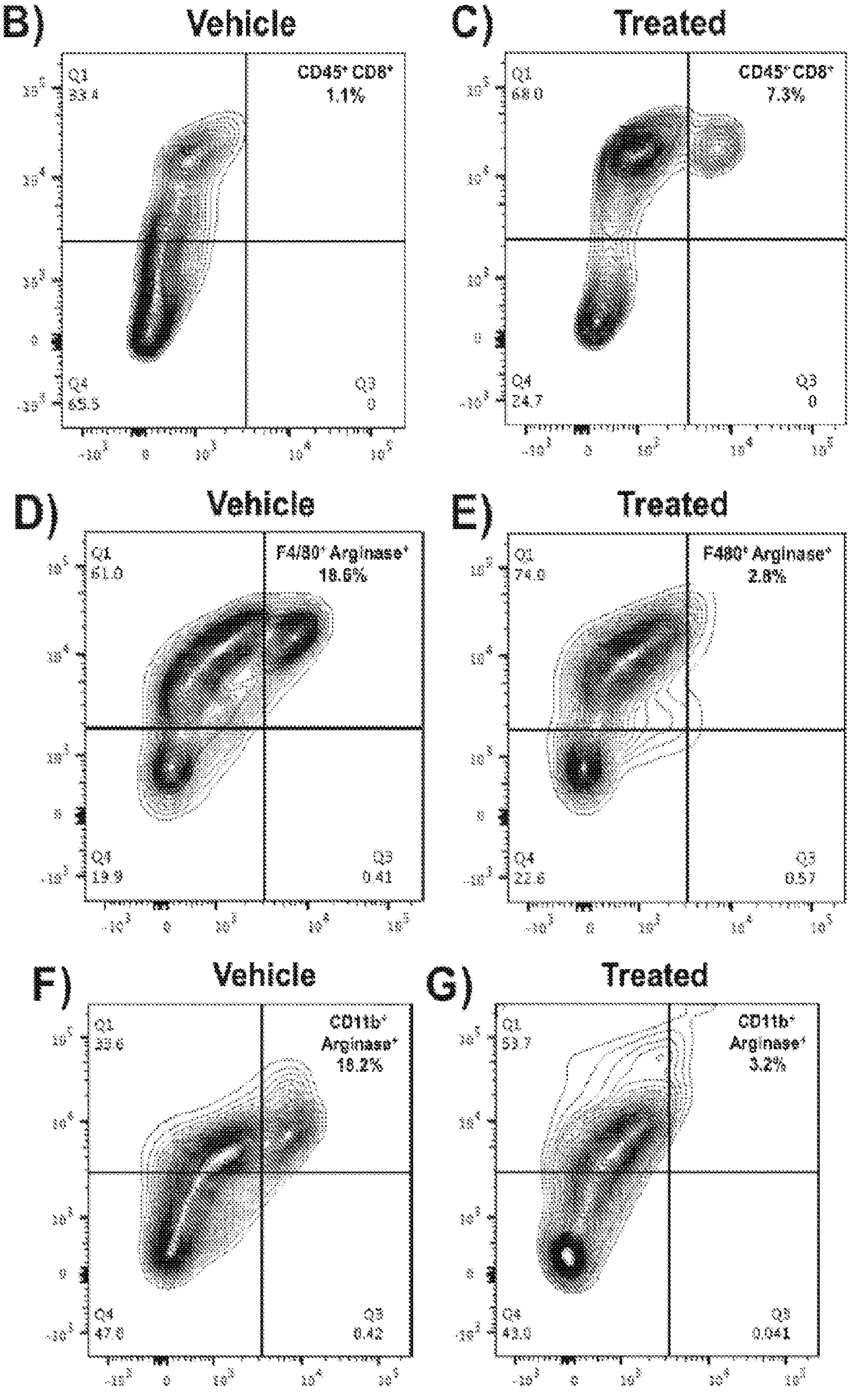
Figures 6H, 6I, 6J, 6K:
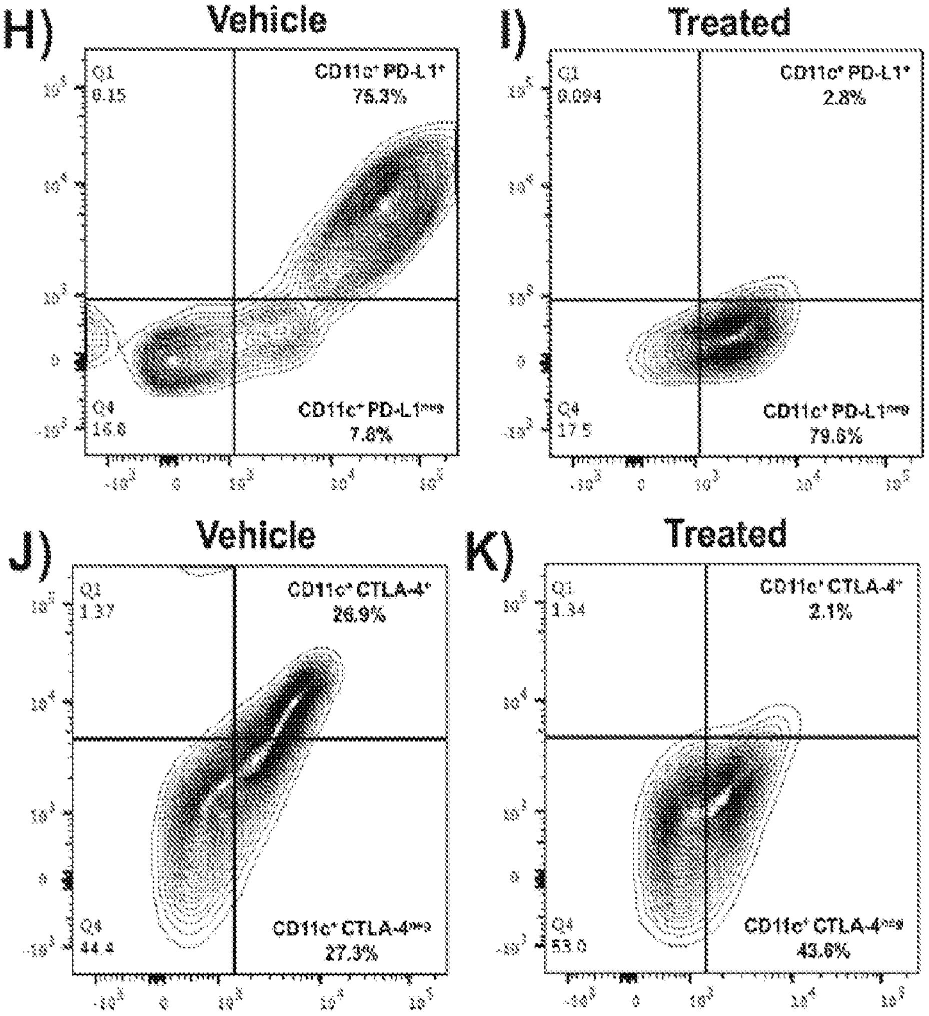

The studies were next moved into second difficult to treat model system, high-risk, MYCN-amplified neuroblastoma. Single cell suspensions were generated from seven week-old Th-MYCN homozygote tumors and grafted ectopically onto the flank of syngeneic wild type mice. Tumors were then treated with either three successive injections of regimen 16 or vehicle control, and growth was monitored by caliper measurement. As shown in FIG. 6A, treatment with regimen 16 was sufficient to fully eliminate MYCN-amplified neuroblastoma, with extensive systemic proliferation of total $CD8^+$ peripheral blood splenocytes observed weeks after tumor resolution (i.e. FIGS. 6B-C). As with the HNSCC MOC-2 model, subsequent experiments were performed in which tumors were treated with two regimen 16 administrations or vehicle after which the microenvironments of the resolving tumors were analyzed. In contrast to the MOC-2 model in which the myeloid cell compartment was substantially resolved following two treatments, resolution of the myeloid compartment in the Th-MYCN model was temporally slower, providing an opportunity to view and characterize the process of myeloid cell resolution in response to treatment with regimen 16. Significantly, characterization of this intermediate step indicated that myeloid cells first de-differentiate from a pro-tumorigenic and immunosuppressive phenotype prior to resolving. While significant differences in the numbers of $CD11c^+$, $CD11b^+$, $F4/80^+$, $Gr\text{-}1^+$, or $Ly6C^+$ cells was not observed between treated and mock-treated tumor cell populations (not shown), both the F4/80 (FIGS. 6D-E) and $CD11b^+$ (FIGS. 6F-G) macrophage populations ceased expression of arginase, indicative of a shift away from an immunosuppressive $T_H2$ phenotype. Further, $CD11c^+$ APC populations ceased both expression of PD-L1 (FIGS. 6H-I) and of CTLA-4 (FIGS. 6J-K), again indicative of a shift from a tolerogenic to an inflammatory phenotype.

In the present work, it was demonstrated that a preparation comprised of innate intracellular signaling ligands, cytotoxic/cytostatic agents, and a TGF-β signaling inhibitor generated highly effective antitumor responses in a TNBC model system generally considered to be non-immunogenic as well as in other difficult to treat model system that included MYCN-amplified neuroblastoma and MOC-2 HNSCC. In the aggressive 4T-1 TNBC model, treatment effectively prevented metastasis, cured primary tumor in 50% of animals that received the highest doses, and clearly involved the generation of cellular memory as determined by adoptive transfer experiments. The components of the preparation were derived from a development process simultaneously both rational and empiric that sought to optimize synergy between a variety of different agents that function through three broad mechanisms thought to be important to the generation of anti-tumor immunity. These three mechanisms were 1) provision of danger signals through ligation of intracellular pattern recognition receptors that upregulate interferon signaling and promulgate $T_H1$ immune responses (Carroll, Jin et al., 2016, Kawai & Akira, 2009, Shi, Vistica et al., 2013, Spranger, Javorovic et al., 2010, Stetson & Medzhitov, 2006, Sun, Wu et al., 2013, Xagorari & Chlichlia, 2008), 2) inhibition of perhaps the most important mediator of tumor-associated immune suppression (i.e. TGF-β)(Beatty & Gladney, 2015, Sinha et al., 2005a, Sinha et al., 2005b, Vinay et al., 2015), and 3) introduction of cytotoxic agents to generate endogenous DAMP signals (Galluzzi et al., 2017, Yatim et al., 2017) and through cell damage to provide antigenic materials against which downstream adaptive immune responses may be primed. While the literature suggests a very wide variety of different agents that might be used to accomplish these broad goals, the manner by which any group of individual agents might interact was not predictable in advance of the significant empiric experimentation documented here. Indeed, certain combinations of promising agents imparted no antitumor effects whatsoever. This appeared especially true of preparations that combined agents intended to inhibit multiple mechanisms of tumor-associated immune suppression, at least in the non-immunogenic 4T-1 TNBC model system in which optimization was performed. These observations were perhaps not entirely unpredictable given the recent high profile failure of the IDO inhibitor epacadostat in randomized phase III studies in combination with pembrolizumab (Garber, 2018). Broad applicability of the TNBC-optimized regimen was subsequently validated in Th-MYCN and MOC-2 HNSCC model systems.

Successful clinical response to anti-PD-1 checkpoint inhibition is known to be significantly correlated with tumor mutational burden (Cristecu et al., 2018; Mandal et al., 2019). Greater numbers of coding mutations are thought to raise the likelihood of generating enough high affinity T-cell epitopes against which productive T-cell responses might be spontaneously generated; however, in cancer patients this process occurs under steady state homeostatic conditions or in the context of cell damage and release of DAMPs following cytotoxic chemo and radiotherapies. In contrast, the multiple PRR signaling ligands combined with inhibition of immunoinhibitory TGF-β signaling alters homeostasis during treatment with the optimized regimen through the initiation of interferon signaling that subsequently mediates increased expression of MHC, upregulation of the immunoproteasome, maturation of myeloid DC, activation of plasmacytoid DC, and a host of other immune potentiating effects not normally induced by standard of care chemo- and radiotherapies (Hervas-Stubbs et al., 2011). These effects alter the balance between tolerance and immunity and may permit not only the generation of T-cell responses against high affinity neoepitopes but also the perpetuation of responses against medium and low affinity T-cells clones. These may be reactive not only against neoepitopes but against upregulated developmental or differentiation antigens as well as against posttranslational modifications relatively unique to the tumor (Ilyas et al., 2015).

Microenvironment characterization of resolving tumors in all three model systems provided an intriguing window into at least one of the mechanisms through which the optimized treatment regimen generated its substantial antitumor effects. In all model systems, mid-treatment analyses of MDSC indicated either a substantial reduction of myeloid cell burden or a snapshot in time that captured de-differentiation of MDSC as they downregulated immunosuppressive markers such as PD-L1. The same was true of M2 macrophages which were either reduced or lost expression of arginase, indicating conversion to an M1 inflammatory phenotype. $CD11c^+$ cells were impacted as well, downregulating expression levels of both CDLA-4 and PD-L1; and observed alterations in various myeloid compartments were accompanied by an influx of $CD8^+$ cells into the tumor bed as well as systemic upregulation of circulating $CD8^+$ cells.

In summary, the present studies showed a unique combination of immuno-modulatory and cytostatic agents, designed and optimized through both rational and empiric approaches, that reconditions the tumor microenvironment and ameliorates poor-prognosis tumor types including the 4T-1 TNBC model generally considered to be non-immunogenic (Brockstedt et al., 2002, Feola et al., 2018, Liu et al., 2018) as well as difficult to treat HNSCC and high-risk neuroblastoma models. A course of therapy optimized for 4T-1 TNBC generated a complete response rate of 50% and eliminated metastatic spread in all animals tested at the highest doses. Results were similar in the HNSCC model but were more robust in high-risk neuroblastoma in which all tumors resolved following treatment. Immune responses were transferable between therapeutic recipient and naïve donor through adoptive transfer, and a sizeable abscopal effect was also demonstrated. The results indicate that the targeting of multiple immunostimulatory and immunoinhibitory pathways can result in dramatic synergistic effects.

Example 2—Materials and Methods

Mice. 6-10 week old female Balb/c mice or C57BL/6 animals of both sexes were procured from Baylor College of Medicine or Jackson Laboratories (Bar Harbor, ME). Th-MYCN mice in the 129X1/SvJ background were a kind gift from Dr. William Weiss (UCSF, San Francisco, CA) and were bred in house. All mice were maintained in accordance with the specific IACUC requirements of Baylor College of Medicine and in accordance with animal protocol AN-8375.

Tumor Implantation and Measurements. 500,000 4T-1 TNBC cells (+/−luc2 transduction) were subcutaneously injected onto the hind quarters/back of each mouse and allowed time to reach palpation (approximately 50-100 $mm^3$) before treatment. For orthotopic 4T-1 experiments, 500,000 4T-1 cells were implanted in the mammary fat pad according to the method of Zhang et al.[34] Following establishment of tumors, experimental cohorts were assembled by means of stratified randomization. Attempts were made to minimize confounding variables such as order of cohort treatment, order of tumor measurement, and cage location by means of simple randomization. Tumors were treated with either the indicated antitumor regimen or vehicle control and measured by IVIS imaging (if applicable) or calculated by caliper measurement. 100,000 MOC-2 HNSCC cells were subcutaneously injected onto the hind quarters/back of each mouse and allowed to become palpable (approximately 50-100 $mm^3$) before treatment. Tumor size and progression were determined by caliper measurement. Single cell suspensions were generated from Th-MYCN tumors according to the method of Kroesen et al.[12] Suspensions were subcutaneously injected onto the hind quarters/back of each mouse and allowed time to reach palpation (approximately 50-100 $mm^3$) before treatment. Tumor size and progression were determined by caliper measurement. Tumor volumes were calculated by measuring in two dimensions according to the formula (longest $length^2$)×shortest length.

IVIS Imaging. Post tumor implantation, mice were injected with 100 d of 10 mg/ml D-Luciferin (Regis Technologies, Morton Grove, IL), incubated for 7 min and bio-luminescence was measured with the IVIS imaging system (Caliper Life Sciences, Waltham, MA) following a 60 second exposure. Imaging was performed at 2-4 day intervals.

Analysis of Tumor Microenvironment. Tumor microenvironment white blood cells were analyzed using the Mouse Tumor Dissociation Kits and Dissociator from Miltenyi Biotec (Gaithersburg, MD) following the manufacturer's instructions. In brief, tumors were excised, sectioned into smaller 2-4 mm pieces, and then placed in individual gentleMACS C tubes with 2.5 ml enzyme mix (2.35 ml RPMI-1640, 100 μl of Enzyme D, 50 μl of Enzyme R, and 12.5 μl of Enzyme A). The tubes were then inverted and locked into the gentleMACS Octodissociater with heaters, and the appropriate programs were run to break down the tumor into a single cell suspension. After program completion, the suspension was filtered through a 70 nm cell strainer to remove any remaining debris, and the cells were pelleted, washed 2× with PBS, and subsequently stained for analysis by flow cytometry. Myeloid cell markers analyzed included Gr-1, Ly6C, CTLA-4, PD-L1, CD11b, CD11c, F4/80, CD45, CD68, CD80, CD86, intracellular arginase, intracellular TGF-β, and/or intracellular IL-12.

Analysis of Circulating PBMC. Mice were bled retroorbitally at specified intervals with samples appropriately mixed with EDTA to prevent clotting. Red blood cells were lysed by treatment with ammonium chloride (Sigma-Aldrich) as recommended by the manufacturer's instructions. The white blood cell pellet was washed once with PBS and resuspended in 1% PBS, 0.01% normal goat serum+sodium azide and kept at 4° C. for staining. The cells were then stained for surface CD45, CD3, CD8, CD4, CD25, CTLA-4, PD-1, CD44, CD127, intracellular Foxp3, and/or IFN-γ.

Antitumor reagents. For optimization in the TNBC model, all reagents were dissolved in either DMSO or sterile water based on solubility requirements and included Copper(II) diethyldithiocarbamate at 85 μg/50 μl (VWR, Radnor, PA), 2-Cl-IB-MECA at 20 μg/50 μl (Millipore, Burlington, MA), DMXAA at 75 g/50 μl (R&D Systems, Minneapolis, MN), 5'ppp-dsRNA/Lyovec at 375 ng/50 μl (Invivogen, San Diego, CA), R848 at 15 μg/50 μl (Invivogen), galunisertib at 30 g/50 μl (Selleckchem, Houston, TX), epcadostat at 5 g/50 μl (Selleckchem), $N^w$-Hydroxy-nor-L-arginine at 6 μg/50 μl (Sigma-Aldrich, St. Louis, MO), L-NMMA at 100 ng/50 μl (Abcam, Boston, MA), clodronate at 80 g/50 μl (Abcam), and 4-1BB ligand at 1 μg/50 μl (NovusBio). Combinatorial treatments were reconstituted as a 10× stock, combined as necessary, and diluted to a 1× concentration with the appropriate diluent. Treatments were intratumorally injected with a 28 gauge needle as a 50 μl bolus. In the HNSCC and neuroblastoma models, the mouse-specific STING agonist DMXAA was replaced by the more broadly species reactive STING agonist 2'3'-c-di-AM(PS)2 (Rp,Rp) at 715 ng/50 μl. Other reagent concentrations in the HNSCC and neuroblastoma models included Copper(II) diethyldithiocarbamate at 172 μg/50 μl, 2-Cl-IB-MECA at 40 μg/50 μl, 5'ppp-dsRNA/Lyovec at 755 ng/50 41, R848 at 30 μg/50 μl, and galunisertib at 60 μg/50 μl.

Adoptive Transfer. Spleens were harvested, physically dissociated, and reduced to a single cell suspension by passing through a 70 μM cell strainer (Corning, Glendale, AZ). Following red blood cells lysis with ammonium chloride (ThermoFisher Scientific, Waltham, MA), white blood cells were washed, pelleted, and resuspended in PBS before subsequent intraperitoneal injection into naïve recipient mice. Forty-eight hours later, adoptively-transferred animals were injected intraperitoneally with 500,000 4T1-luc2 tumor cells and followed by IVIS imaging.

Flow Cytometry Analysis. All flow cytometry analyses were performed using an LSR II flow cytometer (BD Biosciences) and analyzed with FlowJo version 10.0.00003 for the MacIntosh (Tree Star, Inc., Ashland, OR).

Statistical Analysis. Significance of differences, unless stated otherwise, was determined by one-way analysis of variance (ANOVA) using Tukey's honestly significant difference (HSD) post hoc test. Pairwise comparisons were performed by Student's two-tailed t-test. Kaplan-Meier survival significance was determined by the log rank (Mantel-Cox) test. All data are displayed as the mean±SEM or SD as stated. All analyses were performed using Prism software version 8.3 for iOS (GraphPad Software) or Microsoft Excel for Mac version 16.30. Statistical significance was defined as $p \leq 0.05$. Power analysis indicated that experimental differences as small as +/−36% of $\mu$ are statistically significant in a sample size of n=5 assuming $\sigma$=20% of $\mu$, $\alpha$=0.05, and a power of 0.8. Therefore five mice per cohort was typically used unless stated otherwise. Normality and variance of the data were assessed graphically.

TABLE 1

Combinatorial treatment regimens addressing three major mechanisms of action for stimulation of anti-tumor immunity.

| Treatment Number | Ingredients | Fundamental Mechanism | General Goal |
|---|---|---|---|
| 1 | DMSO and PBS | Vehicle Controls | Control |
| 8 | Epacadostat<br>$N^{\omega}$-Hydroxy-nor-L-arginine, Diacetate Salt<br>L-NMMA<br>Clodronate (Liposomes) | IDO1 inhibitor<br>Arginase inhibitor<br>iNOS inhibitor<br>Phagocyte (M2) depletion | To antagonize and/or deplete immunosuppressive cells (e.g. MDSC, M2 Macrophages) |
| 9 | 2-Cl-IB-MECA<br>Copper(II) Diethyldithiocarbamate | Adenosine A3 Receptor agonist<br>Proteosome inhibitor | To delay and/or inhibit tumor cell replication |
| 10 | 4-1bb ligand<br>RIG-I agonist<br>TLR7/8 Agonist (Resiquimod; R848)<br>DMXAA | Stimulates 4-1bb on activated cells<br>Stimulates RIG-I with dsRNA<br>Stimulates TLR7/8 with ssRNA<br>STING agonist | To activate local T cells and Innate cells |
| 11 | Epacadostat<br>$N^{\omega}$-Hydroxy-nor-L-arginine, Diacetate Salt<br>L-NMMA<br>Clodronate (Liposomes)<br>2-Cl-IB-MECA<br>Copper(II) Diethyldithiocarbamate | IDO1 inhibitor<br>Arginase inhibitor<br>iNOS inhibitor<br>Phagocyte (M2) depletion<br>Adenosine A3 Receptor agonist<br>Proteosome inhibitor | To antagonize and/or depelete immunosuppressive cells (e.g. MDSC, M2's) AND delay and/or inhibit tumor cell replication |
| 12 | Epacadostat<br>$N^{\omega}$-Hydroxy-nor-L-arginine, Diacetate Salt<br>L-NMMA<br>Clodronate (Liposomes)<br>4-1bb ligand<br>RIG-I agonist<br>TLR7/8 Agonist (Resiquimod; R848)<br>DMXAA | IDO1 inhibitor<br>Arginase inhibitor<br>iNOS inhibitor<br>Phagocyte (M2) depletion<br>Stimulates 4-1bb on activated cells<br>Stimulates RIG-I with dsRNA<br>Stimulates TLR7/8 with ssRNA<br>STING agonist | To antagonize and/or depelete immunosuppressive cells (e.g. MDSC, M2's) AND activate local immune cells |
| 13 | 2-Cl-IB-MECA<br>Copper(II) Diethyldithiocarbamate<br>4-1bb ligand<br>RIG-I agonist<br>TLR7/8 Agonist (Resiquimod; R848)<br>DMXAA | Adenosine A3 Receptor agonist<br>Proteosome inhibitor<br>Stimulates 4-1bb on activated cells<br>Stimulates RIG-I with dsRNA<br>Stimulates TLR7/8 with ssRNA<br>STING agonist | To delay and/or inhibit tumor cell replication AND activate immune cells |
| 14 | Epacadostat<br>$N^{\omega}$-Hydroxy-nor-L-arginine, Diacetate Salt<br>L-NMMA<br>Clodronate (Liposomes)<br>4-1bb ligand<br>RIG-I agonist<br>TLR7/8 Agonist (Resiquimod; R848)<br>DMXAA<br>2-Cl-IB-MECA<br>Copper(II) Diethyldithiocarbamate | IDO1 inhibitor<br>Arginase inhibitor<br>iNOS inhibitor<br>Phagocyte (M2) depletion<br>Stimulates 4-1bb on activated cells<br>Stimulates RIG-I with dsRNA<br>Stimulates TLR7/8 with ssRNA<br>STING agonist<br>Adenosine A3 Receptor agonist<br>Proteosome inhibitor | To antagonize and/or depelete immunosuppressive cells (e.g. MDSC, M2's) AND delay and/or inhibit tumor cell replication AND to activate local T cells and Innate cells |

TABLE 2

Canine Immunotherapy composition dosage.

| 1.41-fold Amount | | 1x Cohort 1 (ug) | 10x Cohort 2 (ug) | 100x Cohort 3 (mg) |
|---|---|---|---|---|
| Copper(II) Diethyldithiocarbamate | Proteosome Inhibitor | 120 ug | 1,200 ug | 12 mg |
| 2-Cl-IB-MECA | Adenosine A3 Receptor agonist | 28 ug | 280 ug | 2.8 mg |
| 2'3'-c-di-AM(PS)2 (Rp,Rp) | STING agonist | 0.50 ug | 5 ug | 0.05 mg |
| RIG-I agonist (lyovec) | Stimulates RIG-I with dsRNA | 0.53 ug | 5.3 ug | 0.053 mg |

TABLE 2-continued

| Canine Immunotherapy composition dosage. | | | | |
|---|---|---|---|---|
| 1.41-fold Amount | | 1x Cohort 1 (ug) | 10x Cohort 2 (ug) | 100x Cohort 3 (mg) |
| TLR7/8 Agonist (resiquimod; R848) | Stimulates TLR7/8 with ssRNA | 21 ug | 210 ug | 2.1 mg |
| TGFβ Inhibitor (galunisertib) | Inhibits TGFβ-mediated SMAD2 phosphorylation | 42 ug | 420 ug | 4.2 mg |

For the canine clinical protocol, canines were injected with 3 aliquots in 3.5 mL normal saline/DMSO intratumorally on Days 0, 7, and 14. CBC/Chem/and UA were performed. Tumor caliper measurements were taken in two dimensions and on Day 21 the tumor was surgically removed for analysis. Radiographic imaging was performed at 6 months.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Batlle E, Massague J (2019) Transforming Growth Factor-beta Signaling in Immunity and Cancer. Immunity 50: 924-940

Beatty G L, Gladney W L (2015) Immune escape mechanisms as a guide for cancer immunotherapy. Clin Cancer Res 21: 687-92

Bhola N E, Balko J M, Dugger T C, Kuba M G, Sanchez V, Sanders M, Stanford J, Cook R S, Arteaga C L (2013) TGF-beta inhibition enhances chemotherapy action against triple-negative breast cancer. J Clin Invest 123: 1348-58

Boettler T, Panther E, Bengsch B. Nazarova N, Spangenberg H C, Blum H E, Thimme R (2006) Expression of the interleukin-7 receptor alpha chain (CD127) on virus-specific CD8+ T cells identifies functionally and phenotypically defined memory T cells during acute resolving hepatitis B virus infection. J Virol 80: 3532-40

Brahmer J R, Tykodi S S, Chow L Q, Hwu W J, Topalian S L, Hwu P, Drake C G, Camacho L H, Kauh J, Odunsi K, Pitot H C, Hamid O, Bhatia S, Martins R, Eaton K, Chen S, Salay T M, Alaparthy S, Grosso J F, Korman A J et al. (2012) Safety and activity of anti-PD-L1 antibody in patients with advanced cancer. N Engl J Med 366: 2455-65

Brockstedt D G, Diagana M, Zhang Y, Tran K, Belmar N, Meier M, Yang A, Boissiere F, Lin A, Chiang Y (2002) Development of anti-tumor immunity against a non-immunogenic mammary carcinoma through in vivo somatic GM-CSF, IL-2, and HSVtk combination gene therapy. Mol Ther 6: 627-36

Brunet J F, Denizot F, Luciani M F, Roux-Dosseto M, Suzan M, Mattei M G, Golstein P (1987) A new member of the immunoglobulin superfamily—CTLA-4. Nature 328: 267-70

Carroll E C, Jin L, Mori A, Munoz-Wolf N, Oleszycka E, Moran HBT, Mansouri S, McEntee C P, Lambe E, Agger E M, Andersen P, Cunningham C, Hertzog P, Fitzgerald K A, Bowie A G, Lavelle E C (2016) The Vaccine Adjuvant Chitosan Promotes Cellular Immunity via DNA Sensor cGAS-STING-Dependent Induction of Type I Interferons. Immunity 44: 597-608

Chester C, Sanmamed M F, Wang J, Melero I (2018) Immunotherapy targeting 4-1BB: mechanistic rationale, clinical results, and future strategies. Blood 131: 49-57

Clowes G H A, Baeslack F W (1905) Further Evidence of Immunity Against Cancer in Mice after Sontaneous Recovery. Med News 87: 968-71

Cristescu R, Mogg R, Ayers M, Albright A, Murphy E, Yearley J, Sher X, Liu X Q, Lu H, Nebozhyn M, Zhang C, Lunceford J K, Joe A, Cheng J, Webber A L, Ibrahim N, Plimack E R, Ott P A, Seiwert T Y, Ribas A et al. (2018) Pan-tumor genomic biomarkers for PD-1 checkpoint blockade-based immunotherapy. Science 362

Decker W K, Safdar A (2009) Bioimmunoadjuvants for the treatment of neoplastic and infectious disease: Coley's legacy revisited. Cytokine Growth Factor Rev 20: 271-81

Decker W K, Safdar A (2011) Cytokine adjuvants for vaccine therapy of neoplastic and infectious disease. Cytokine Growth Factor Rev 22: 177-87

Feola S, Capasso C, Fusciello M, Martins B, Tahtinen S, Medeot M, Carpi S, Frascaro F, Ylosmaki E, Peltonen K, Pastore L, Cerullo V (2018) Oncolytic vaccines increase the response to P D-L1 blockade in immunogenic and poorly immunogenic tumors. Oncoimmunology 7: e1457596

Galluzzi L, Buque A, Kepp O, Zitvogel L, Kroemer G (2017) Immunogenic cell death in cancer and infectious disease. Nat Rev Immunol 17: 97-111

Garber K (2018) A new cancer immunotherapy suffers a setback. Science 360: 588 Graham J B, Graham R M (1959) The effect of vaccine on cancer patients. Surg Gynecol Obstet 109: 131-8

Gross L (1943) Intradermal Immunization of C3H Mice against a Sarcoma That Originated in an Animal of the Same Line. Cancer Res 3: 326-33

Hamilton M J, Bosiljcic M, Lepard N E, Halvorsen E C, Ho V W, Banath J P, Krystal G, Bennewith K L (2014) Macrophages are more potent immune suppressors ex vivo than immature myeloid-derived suppressor cells induced by metastatic murine mammary carcinomas. J Immunol 192: 512-22

Hellmann M D, Ciuleanu T E, Pluzanski A, Lee J S, Otterson G A, Audigier-Valette C, Minenza E, Linardou H, Burgers S, Salman P, Borghaei H, Ramalingam S S, Brahmer J, Reck M, O'Byrne K J, Geese W J, Green G, Chang H, Szustakowski J, Bhagavatheeswaran P et al. (2018) Nivolumab plus Ipilimumab in Lung Cancer with a High Tumor Mutational Burden. N Engl J Med 378: 2093-2104

Hervas-Stubbs S, Perez-Gracia J L, Rouzaut A, Sanmamed M F, Le Bon A, Melero I (2011) Direct effects of type I interferons on cells of the immune system. Clin Cancer Res 17: 2619-27

Hodi F S, O'Day S J, McDermott D F, Weber R W, Sosman J A, Haanen J B, Gonzalez R, Robert C, Schadendorf D, Hassel J C. Akerley W, van den Eertwegh A J, Lutzky J, Lorigan P, Vaubel J M, Linette G P, Hogg D, Ottensmeier C H, Lebbe C, Peschel C et al. (2010) Improved survival with ipilimumab in patients with metastatic melanoma. N Engl J Med 363: 711-23

Hubalek M, Czech T, Muller H (2017) Biological Subtypes of Triple-Negative Breast Cancer. Breast Care (Basel) 12: 8-14

Huster K M, Busch V, Schiemann M, Linkemann K, Kerksiek K M, Wagner H, Busch D H (2004) Selective expression of IL-7 receptor on memory T cells identifies early CD40L-dependent generation of distinct CD8+ memory T cell subsets. Proc Natl Acad Sci USA 101: 5610-5

Ilyas S, Yang J C (2015) Landscape of Tumor Antigens in T Cell Immunotherapy. J Immunol 195: 5117-22

Jacobson et al., Front. Cell. Neurosci., 2019

Jafari S M, Panjehpour M, Aghaei M, Joshaghani H R, Enderami S E (2017) A3 Adenosine Receptor Agonist Inhibited Survival of Breast Cancer Stem Cells via GLI-1 and ERK1/2 Pathway. J Cell Biochem 118: 2909-2920

Kawai T, Akira S (2009) The roles of TLRs, RLRs and NLRs in pathogen recognition. Int Immunol 21: 317-37

Krieg A M (2007) Development of TLR9 agonists for cancer therapy. J Clin Invest 117: 1184-94

Leach D R, Krummel M F, Allison J P (1996) Enhancement of antitumor immunity by CTLA-4 blockade. Science 271: 1734-6

Lee S W, Salek-Ardakani S, Mittler R S, Croft M (2009) Hypercostimulation through 4-1BB distorts homeostasis of immune cells. J Immunol 182: 6753-62

Liu L, Wang Y, Miao L, Liu Q, Musetti S, Li J, Huang L (2018) Combination Immunotherapy of MUC1 mRNA Nano-vaccine and CTLA-4 Blockade Effectively Inhibits Growth of Triple Negative Breast Cancer. Mol Ther 26: 45-55

Liu W, Putnam A L, Xu-Yu Z, Szot G L, Lee M R, Zhu S, Gottlieb P A, Kapranov P, Gingeras T R, Fazekas de St Groth B, Clayberger C, Soper D M, Ziegler S F, Bluestone J A (2006) CD127 expression inversely correlates with FoxP3 and suppressive function of human CD4+ T reg cells. J Exp Med 203: 1701-11

Mandal R, Samstein R M, Lee K W, Havel J J, Wang H, Krishna C, Sabio E Y, Makarov V, Kuo F, Blecua P, Ramaswamy A T, Durham J N, Bartlett B, Ma X, Srivastava R, Middha S, Zehir A, Hechtman J F. Morris L G, Weinhold N et al. (2019) Genetic diversity of tumors with mismatch repair deficiency influences anti-PD-1 immunotherapy response. Science 364: 485-491

Marcus L, Lemery S J, Keegan P, Pazdur R (2019) FDA Approval Summary: Pembrolizumab for the Treatment of Microsatellite Instability-High Solid Tumors. Clin Cancer Res 25: 3753-3758

Marra A, Viale G, Curigliano G (2019) Recent advances in triple negative breast cancer: the immunotherapy era. BMC Med 17: 90

Miller J F, Mitchell G F, Weiss N S (1967) Cellular basis of the immunological defects in thymectomized mice. Nature 214: 992-7

Mitchell B S (2003) The proteasome—an emerging therapeutic target in cancer. N Engl J Med 348: 2597-8

Overman M J, Lonardi S, Wong KYM, Lenz H J, Gelsomino F, Aglietta M, Morse M A, Van Cutsem E, McDermott R, Hill A, Sawyer M B, Hendlisz A, Neyns B, Svrcek M, Moss R A, Ledeine J M, Cao Z A, Kamble S, Kopetz S, Andre T (2018) Durable Clinical Benefit With Nivolumab Plus Ipilimumab in DNA Mismatch Repair-Deficient/Microsatellite Instability-High Metastatic Colorectal Cancer. J Clin Oncol 36: 773-779

Park B H, Biggar W D, Good R A (1974) Minnesota experience in bone-marrow transplantation in man, 1968 to June 1973. Transplant Proc 6: 379-83

Rizvi N A, Hellmann M D, Snyder A, Kvistborg P, Makarov V, Havel J J, Lee W, Yuan J, Wong P, Ho T S, Miller M L, Rekhtman N, Moreira A L, Ibrahim F. Bruggeman C, Gasmi B, Zappasodi R, Maeda Y, Sander C, Garon E B et al. (2015) Cancer immunology. Mutational landscape determines sensitivity to PD-1 blockade in non-small cell lung cancer. Science 348: 124-8

Rodon J, Carducci M A, Sepulveda-Sanchez J M, Azaro A, Calvo E. Seoane J, Brana I, Sicart E, Gueorguieva I, Cleverly A L, Pillay N S, Desaiah D, Estrem S T, Paz-Ares L, Holdhoff M, Blakeley J, Lahn M M, Baselga J (2015) First-in-human dose study of the novel transforming growth factor-beta receptor I kinase inhibitor LY2157299 monohydrate in patients with advanced cancer and glioma. Clin Cancer Res 21: 553-60

Segal N H, Logan T F, Hodi F S, McDermott D, Melero I, Hamid O, Schmidt H, Robert C, Chiarion-Sileni V, Ascierto P A, Maio M, Urba W J, Gangadhar T C, Suryawanshi S, Neely J, Jure-Kunkel M, Krishnan S, Kohrt H, Sznol M, Levy R (2017) Results from an Integrated Safety Analysis of Urelumab, an Agonist Anti-CD137 Monoclonal Antibody. Clin Cancer Res 23: 1929-1936

Shi G, Vistica B P, Nugent L F, Tan C, Wawrousek E F, Klinman D M, Gery I (2013) Differential involvement of Th1 and Th17 in pathogenic autoimmune processes triggered by different TLR ligands. J Immunol 191: 415-23

Simpson K D, Templeton D J, Cross J V (2012) Macrophage migration inhibitory factor promotes tumor growth and metastasis by inducing myeloid-derived suppressor cells in the tumor microenvironment. J Immunol 189: 5533-40

Sinha P, Clements V K, Bunt S K, Albelda S M, Ostrand-Rosenberg S (2007) Cross-talk between myeloid-derived suppressor cells and macrophages subverts tumor immunity toward a type 2 response. J Immunol 179: 977-83

Sinha P, Clements V K, Ostrand-Rosenberg S (2005a) Interleukin-13-regulated M2 macrophages in combination with myeloid suppressor cells block immune surveillance against metastasis. Cancer Res 65: 11743-51

Sinha P, Clements V K, Ostrand-Rosenberg S (2005b) Reduction of myeloid-derived suppressor cells and induction of M1 macrophages facilitate the rejection of established metastatic disease. J Immunol 174: 636-45

Skrott Z, Cvek B (2012) Diethyldithiocarbamate complex with copper: the mechanism of action in cancer cells. Mini Rev Med Chem 12: 1184-92

Smith H O, Wilcox K W (1970) A restriction enzyme from *Hemophilus influenzae*. I. Purification and general properties. J Mol Biol 51: 379-91

Spranger S, Javorovic M, Burdek M, Wilde S, Mosetter B, Tippmer S, Bigalke I, Geiger C, Schendel D J, Frankenberger B (2010) Generation of Th1-polarizing dendritic cells using the TLR7/8 agonist CL075. J Immunol 185: 738-47

Steinman R M, Cohn Z A (1973) Identification of a novel cell type in peripheral lymphoid organs of mice. I. Morphology, quantitation, tissue distribution. J Exp Med 137: 1142-62

Stetson D B, Medzhitov R (2006) Recognition of cytosolic DNA activates an IRF3-dependent innate immune response. Immunity 24: 93-103

Sun L, Wu J, Du F, Chen X, Chen Z J (2013) Cyclic GMP-AMP synthase is a cytosolic DNA sensor that activates the type I interferon pathway. Science 339: 786-91

Topalian S L, Hodi F S, Brahmer J R, Gettinger S N, Smith D C, McDermott D F, Powderly J D, Carvajal R D, Sosman J A, Atkins M B, Leming P D, Spigel D R, Antonia S J, Horn L, Drake C G, Pardoll D M, Chen L, Sharfman W H, Anders R A, Taube J M et al. (2012) Safety, activity, and immune correlates of anti-PD-1 antibody in cancer. N Engl J Med 366: 2443-54

Vinay D S, Ryan E P, Pawelec G, Talib W H, Stagg J, Elkord E, Lichtor T, Decker W K, Whelan R L, Kumara H, Signori E, Honoki K, Georgakilas A G, Amin A, Helferich W G, Boosani C S, Guha G, Ciriolo M R, Chen S, Mohammed S I et al. (2015) Immune evasion in cancer: Mechanistic basis and therapeutic strategies. Semin Cancer Biol 35 Suppl: S185-S198

Waks A G, Winer E P (2019) Breast Cancer Treatment: A Review. JAMA 321: 288-300

Wolchok J D, Chiarion-Sileni V, Gonzalez R, Rutkowski P, Grob J J, Cowey C L, Lao C D, Wagstaff J, Schadendorf D, Ferrucci P F, Smylie M, Dummer R, Hill A, Hogg D, Haanen J, Carlino M S, Bechter 0, Maio M, Marquez-Rodas I, Guidoboni M et al. (2017) Overall Survival with Combined Nivolumab and Ipilimumab in Advanced Melanoma. N Engl J Med 377: 1345-1356

Xagorari A, Chlichlia K (2008) Toll-like receptors and viruses: induction of innate antiviral immune responses. Open Microbiol J 2: 49-59

Yatim N, Cullen S, Albert M L (2017) Dying cells actively regulate adaptive immune responses. Nat Rev Immunol 17: 262-275

Zhang W, Wang G, Xu Z G, Tu H, Hu F, Dai J, Chang Y, Chen Y, Lu Y, Zeng H, Cai Z, Han F, Xu C, Jin G, Sun L, Pan B S, Lai S W, Hsu C C, Xu J, Chen Z Z et al. (2019) Lactate Is a Natural Suppressor of RLR Signaling by Targeting MAVS. Cell 178: 176-189 e15

Zhao B, Du F, Xu P, Shu C, Sankaran B, Bell S L, Liu M, Lei Y, Gao X, Fu X, Zhu F, Liu Y, Laganowsky A, Zheng X, Ji J Y, West A P, Watson R O, Li P (2019) A conserved PLPLRT/S D motif of STING mediates the recruitment and activation of TBK1. Nature 569: 718-722

Zinkemagel R M, Doherty P C (1974) Restriction of in vitro T cell-mediated cytotoxicity in lymphocytic choriomeningitis within a syngeneic or semiallogeneic system. Nature 248: 701-2

U.S. Pat. No. 6,747,014

U.S. Pat. No. 6,753,423

U.S. Patent Publication No. 2014/0005255

What is claimed is:

1. An immunogenic composition comprising at least 4 of the following: a transforming growth factor beta (TGFβ) antagonist, a stimulator of interferon genes (STING) agonist, a Toll-like receptor 7/8 (TLR7/8) agonist, a RIG-I agonist, a proteasome inhibitor, an adenosine A3 receptor agonist, and a 4-1BB agonist.

2. The composition of claim 1, wherein the composition comprises:

(a) a transforming growth factor beta (TGFβ) antagonist, a stimulator of interferon genes (STING) agonist, a Toll-like receptor 7/8 (TLR7/8) agonist, a RIG-I agonist, and a proteasome inhibitor; or (b) a transforming growth factor beta (TGFβ) antagonist, a stimulator of interferon genes (STING) agonist, a Toll-like receptor 7/8 (TLR7/8) agonist, a RIG-I agonist, and an adenosine A3 receptor agonist; or (c) a 4-1BB agonist, a stimulator of interferon genes (STING) agonist, a Toll-like receptor 7/8 (TLR7/8) agonist, a RIG-I agonist, and a proteasome inhibitor; or (d) a 4-1BB agonist, a stimulator of interferon genes (STING) agonist, a Toll-like receptor 7/8 (TLR7/8) agonist, a RIG-I agonist, and an adenosine A3 receptor agonist.

3. The composition of claim 1, wherein the TGFβ antagonist is galunisertib (LY2157299), trabedersen, fresolimumab, LY2382770, lucanix, or PF-03446962.

4. The composition of claim 1, wherein the STING agonist is:

(a) a cyclic dinucleotide or xanthenone analog, optionally wherein the xanthenone analog is 5,6-dimethylxanthenone-4-acetic acid (DMXAA);

(b) 2'3'-c-di-AM (PS) 2 (Rp,Rp); or (c) a cyclic dinucleotide selected from the group consisting of 3'3'-cGAMP, 2'3'-cGAMP, 2'2'-cGAMP, c-di-APM, c-di-GMP, c-di-IMP, and c-di-UMP.

5. The composition of claim 1, wherein the TLR7/8 agonist is resiquimod (R848), CL075, CL097, CL264, CL307, GS-9620, Poly(dT), imiquimod, gardiquimod, loxoribine or a ssRNA oligonucleotide.

6. The composition of claim 1, wherein the RIG-I agonist is 5'ppp-dsRNA, MDA5 ligand, a LGP2 ligand, a ssRNA, a dsRNA, Poly(dA: dT), or Poly(I: C).

7. The composition of claim 1, wherein the proteasome inhibitor is Copper (II) Diethyldithiocarbamate, bortezomib, delanzomib, ixazomib, MG132, MG115, IPSI 001, fellutamide B, ALLN, leupeptin, epoxomicin, oprozomib, PR-957, carfilzomib, lactacystin, omuralide, salinosporamide A, salinosporamide B, a belactosine, a cinnabaramide, a polyphenol, TMC-95, or PS-519.

8. The composition of claim 1, wherein the adenosine A3 receptor agonist is 2-Chloro-N(6)-(3-iodobenzyl) adenosine-5'-N-methylcarboxamide (2-CI-IB-MECA), IB-MECA (CF101), CP-608,039, CP-532,903, MRS5698, MRS5980, LJ-529 33, or MRS4322.

9. The composition of claim 1, wherein the 4-1BB agonist is a 4-1BB agonist antibody, recombinant 4-1BB ligand (4-1BBL), or 4-1BB apatamer, optionally wherein the 4-1BB agonist antibody is utomilumab or urelumab.

10. The composition of claim 1, wherein the composition does not comprise hydrogel, an immune checkpoint inhibitor, a cytokine, and/or an antigen.

11. A method of stimulating an anti-tumor immune response in a subject comprising administering to the subject an effective amount of at least 4 of the following:

a transforming growth factor beta (TGFβ) antagonist, a 4-1BB agonist, a stimulator of interferon genes (STING) agonist, a Toll-like receptor 7/8 (TLR7/8) agonist, a RIG-I agonist, a proteasome inhibitor, and an adenosine A3 receptor agonist.

12. The method of claim 11, wherein the subject is administered:

(a) a 4-1BB agonist, a stimulator of interferon genes (STING) agonist, a Toll-like receptor 7/8 (TLR7/8) agonist, a RIG-I agonist, and a proteasome inhibitor; or (b) a transforming growth factor beta (TGFβ) antagonist, a stimulator of interferon genes (STING) agonist, a Toll-like receptor 7/8 (TLR7/8) agonist, a RIG-I agonist, and a proteasome inhibitor;

(c) a 4-1BB agonist, a stimulator of interferon genes (STING) agonist, a Toll-like receptor 7/8 (TLR7/8) agonist, a RIG-I agonist, and an adenosine A3 receptor agonist; or (d) a transforming growth factor beta (TGFβ) antagonist, a stimulator of interferon genes (STING) agonist, a Toll-like receptor 7/8 (TLR7/8) agonist, a RIG-I agonist, and an adenosine A3 receptor agonist.

13. The method of claim 11, wherein the TGFβ antagonist is galunisertib (LY2157299), trabedersen, fresolimumab, LY2382770, lucanix, or PF-03446962.

14. The method of claim 11, wherein the STING agonist is:

(a) a cyclic dinucleotide or xanthenone analog; wherein the xanthenone analog is 5,6-dimethylxanthenone-4-acetic acid (DMXAA);

(b) 2'3'-c-di-AM (PS) 2 (Rp,Rp); or (c) a cyclic dinucleotide selected from the group consisting of 3'3'-cGAMP, 2'3'-cGAMP, 2'2'-cGAMP, c-di-APM, c-di-GMP, c-di-IMP, and c-di-UMP.

15. The method of claim 11, wherein the TLR7/8 agonist is resiquimod (R848), CL075, CL097, CL264, CL307, GS-9620, Poly(dT), imiquimod, gardiquimod, loxoribine or a ssRNA oligonucleotide.

16. The method of claim 11, wherein the RIG-I agonist is 5'ppp-dsRNA, MDA5 ligand, a LGP2 ligand, a ssRNA, a dsRNA, Poly(dA: dT), or Poly(I: C).

17. The method of claim 11, wherein the proteasome inhibitor is Copper (II) Diethyldithiocarbamate, bortezomib, delanzomib, ixazomib, MG132, MG115, IPSI 001, fellutamide B, ALLN, leupeptin, epoxomicin, oprozomib, PR-957, carfilzomib, lactacystin, omuralide, salinosporamide A, salinosporamide B, a belactosine, a cinnabaramide, a polyphenol, TMC-95, or PS-519.

18. The method of claim 11, wherein the adenosine A3 receptor agonist is 2-Chloro-N(6)-(3-iodobenzyl) adenosine-5'-N-methylcarboxamide (2-CI-IB-MECA), IB-MECA (CF101), CP-608,039, CP-532,903, MRS5698, MRS5980, LJ-529 33, or MRS4322.

19. The method of claim 11, wherein the 4-1BB agonist is a 4-1BB agonist antibody, recombinant 4-1BB ligand (4-1BBL), or 4-1BB apatamer, optionally wherein the 4-1BB agonist antibody is utomilumab or urelumab.

20. The method of claim 11, wherein the subject:

(a) is human; and/or (b) has cancer, optionally wherein the cancer is triple negative breast cancer (TNBC), pancreatic ductal adenocarcinoma (PDAC), melanoma, or head and neck cancer.

21. The method of claim 20, wherein the administering:

(a) is performed prior to surgical intervention or the subject has not undergone surgical resection of a tumor; and/or (b) comprises intratumoral injection, optionally wherein the intratumoral injection does not comprise hydrogel.

22. The method of claim 11, wherein the immunogenic composition is administered more than once, optionally wherein the immunogenic composition is administered two or more times.

23. The method of claim 20, wherein administering the immunogenic composition results in an increase in circulating CD8+ T cells, M1 macrophages and/or tumor infiltrating dendritic cells, optionally wherein the CD8+ T cells are CD8+IFN-γ+cells, or in a durable T cell memory response as measured by an increase in CD44+CD127+ T cells as compared to CD44+CD127+ T cells prior to administration.

24. The method of claim 11, wherein the method does not comprise administering a cell therapy to said subject at the time the immunogenic composition is administered, and/or administering an immune checkpoint inhibitor, cytokine, and/or antigen to said subject at the time the immunogenic composition is administered.

25. The method of claim 11, further comprising administering an additional anti-cancer therapy, optionally wherein the additional anti-cancer therapy comprises chemotherapy, gene therapy, surgery, hormonal therapy, anti-angiogenic therapy or immunotherapy.

* * * * *